(12) United States Patent
Lauc et al.

(10) Patent No.: US 9,910,046 B2
(45) Date of Patent: Mar. 6, 2018

(54) METHOD FOR THE ANALYSIS OF N-GLYCANS ATTACHED TO IMMUNOGLOBULIN G FROM HUMAN BLOOD PLASMA AND ITS USE

(71) Applicant: GENOS d.o.o., Osijek (HR)

(72) Inventors: Gordan Lauc, Zagreb (HR); Maja Pucic Bakovic, Zagreb (HR); Frano Vuckovic, Zagreb (HR)

(73) Assignee: GENOS D.O.O., Osijek (HR)

( * ) Notice: Subject to any disclaimer, the term of this patent is extended or adjusted under 35 U.S.C. 154(b) by 238 days.

(21) Appl. No.: 14/892,299

(22) PCT Filed: Jun. 11, 2014

(86) PCT No.: PCT/HR2014/000022
§ 371 (c)(1),
(2) Date: Nov. 19, 2015

(87) PCT Pub. No.: WO2014/203010
PCT Pub. Date: Dec. 24, 2014

(65) Prior Publication Data
US 2016/0103137 A1 Apr. 14, 2016

(30) Foreign Application Priority Data
Jun. 20, 2013 (HR) .............................. P 20130568 A

(51) Int. Cl.
*G01N 33/68* (2006.01)
*G01N 33/53* (2006.01)
*G01N 30/72* (2006.01)
*G01N 30/02* (2006.01)

(52) U.S. Cl.
CPC ......... *G01N 33/6854* (2013.01); *G01N 30/72* (2013.01); *G01N 33/5308* (2013.01); *G01N 33/6851* (2013.01); *G01N 2030/027* (2013.01); *G01N 2333/976* (2013.01); *G01N 2400/10* (2013.01); *G01N 2440/38* (2013.01); *G01N 2800/52* (2013.01); *G01N 2800/7042* (2013.01)

(58) Field of Classification Search
None
See application file for complete search history.

(56) References Cited

U.S. PATENT DOCUMENTS

| 7,335,512 | B2 | 2/2008 | Callewaert et al. |
| 2008/0003180 | A1* | 1/2008 | Chen ...................... G01N 33/50 424/9.2 |
| 2009/0181461 | A1 | 7/2009 | Miyoshi et al. |
| 2010/0003699 | A1* | 1/2010 | Satomaa .............. G01N 33/574 435/7.2 |
| 2011/0143351 | A1 | 6/2011 | Rudd et al. |

FOREIGN PATENT DOCUMENTS

JP H 9-257790 10/1997

OTHER PUBLICATIONS

Maja Pucic Bakovic et al., "High-Throughput IgG Fc N-Glycosylation Profiling by Mass Spectrometry of Glycopeptides," J. Proteome Res. 2013, 12, 821-831.

Lauc et al., "Loci Associated with N-Glycosylation of Human Immunoglobulin G Show Pleiotropy with Autoimmune Diseases and Haematological Cancers," PLOS Genetics, Jan. 2013, vol. 9, Issue 1.

Kristic et al., "Glycans Are a Novel Biomaker of Chronological and Biological Ages," J. Gerontology A Biol Sci Med Sci Jul. 2014; 69(7):779-789.

Parekh et al., "Age-Related Galactosylation of the N-Linked Oligosaccharides of Human Serum IgG," J. Exp. Med. vol. 167, May 1988, 1731-1736.

Ruhaak et al., "Decreased Levels of Bisecting GlcNAc Glycoforms of IgG are Associated with Human Longevity," PLoS One, Sep. 2010, vol. 5, Issue 9.

Shikata et al., "Structural changes in the oligosaccharide moiety of human IgG with aging," Glycoconjugate Journal 15, 683-689 (1998).

(Continued)

*Primary Examiner* — Thane Underdahl
(74) *Attorney, Agent, or Firm* — RatnerPrestia

(57) ABSTRACT

The invention discloses a method for the analysis of N-glycans attached to immunoglobulin G (IgG) or IgG N-glycopeptides from human blood plasma in which relative abundance of two or more glycans is determined, out of total six, and for these glycans it is determined that they strongly correlate with age. The glycans have the following structures:

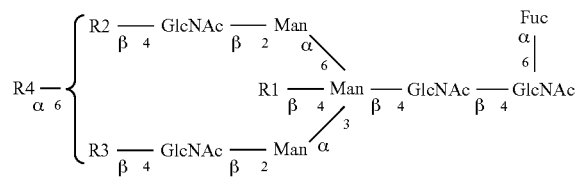

F(6)A2 (GP4): R1, R2, R3, R4=H
F(6)A2B (GP6): R1=GlcNAc; R2, R3, R4=H
F(6)A2[6]G1 (GP8): R1, R3, R4=H; R2=Gal
F(6)A2G2 (GP14): R1=H; R2, R3=Gal; R4=H
F(6)A2BG2 (GP15): R1=GlcNAc; R2, R3=Gal; R4=H
F(6)A2G2S1 (GP18): R1=H; R2, R3=Gal; R4=NeuAc
GlcNAc=N-acetylglucosamine
Fuc=fucose
Man=mannose
NeuAc=N-acetylneuraminic acid
Gal=galactose From the results of the analysis, Glycan Age Index (GAI) is calculated, and it is useful for: prediction of biological age of a tested individual; monitoring efficacy of methods that slow down the ageing process; monitoring progression of diseases that are developed as a result of the ageing process advancement, like: inflammatory diseases (including atherosclerosis), autoimmune diseases, tumours, diabetes, arthritis, osteoporosis, and Alzheimer disease; and evaluation of overall condition/health of a body.

5 Claims, 50 Drawing Sheets

(56) References Cited

OTHER PUBLICATIONS

Yamada et al., "Structural changes of immunoglobulin G oligosaccharides with age in healthy human serum," Glycoconjugate Journal (1997) 14:401-405.

Pucic et al., "High Throughout Isolation and Glycosylation Analysis of IgG-Variability and Heritability of the IgG Glycome in Three Isolated Human Populations," Technological Innovations and Resources, The American Society for Biochemistry and Molecular Biology, Inc. http://www.mcponline.org.

Ruhaak et al., "Plasma protein N-glycan profiles are associated with calendar age, familial longevity and health," J. Proteome Res. 2011, 10, 1667-1674.

Ceroni et al., "GlycoWorkbench: A Tool for the Computer-Assisted Annotation of Mass Spectra of Glycans," J. Proteome Res. 2008, 7, 1650-1659.

Saldova et al., "Ovarian cancer is associated with changes in glycosylation in both acute-phase proteins and IgG," Glycobiology (2007) vol. 17, No. 12, 1344-1356.

Thanabalasingham et al., "Mutations in HNF1A Result in Marked Alterations of Plasma Glycan Profile," Dec. 28, 2012 www.diabetes.diabetesjournals.org.

Gornik et al., "Glycosylation of serum proteins in inflammatory diseases," Disease Markers 25 (2008) 267-278.

Selman et al., "Fc specific IgG glycosylation profiling by robust nano-reverse phase HPLC-MS using a sheath-flow ESI sprayer interface," J. Proteomics 75 (2012) 1318-1329.

Ruhaak et al., "Optimized Workflow for Preparation of APTS-Labeled N-Glycans Allowing High-Throughput Analysis of Human Plasma Glycomes using 48-Channel Multiplexed CGE-LIF," J. Proteome Research 9 (2010) 6655-6664.

International Search Report issued in PCT/HR2014/000022 dated Sep. 22, 2014.

\* cited by examiner

| No | Glycan | Mark | Structure |
|---|---|---|---|
| 1. | A2G2S2 | GP21 | 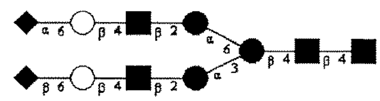 |
| 2. | A2G2S2 | GP21 | 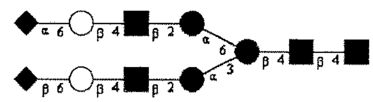 |
| 3. | A2BG2S2 | GP22 | 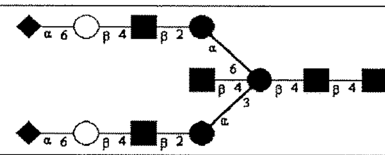 |
| 4. | FA2G2S2 | GP23 | 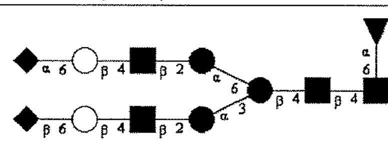 |
| 5. | FA2BG2S2 | GP24 | 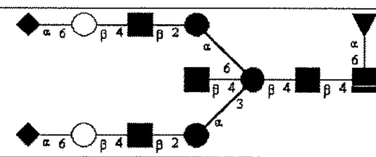 |
| 6. | A2G1S1 | GP15 | 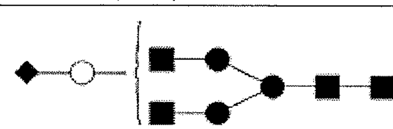 |
| 7. | FA2G2S1[3] | GP16b | 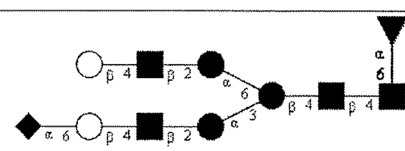 |
| 8. | A2G2S1[3] | GP17 | 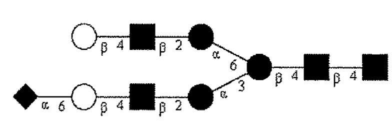 |
| 9. | A2BG2S1 | GP18a | 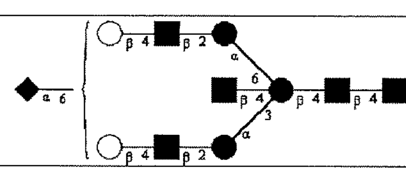 |

| 10. | A2BG2S1 | GP18a | |
|---|---|---|---|
| 11 | FA2G2S1 | GP18b | |
| | Man5 | GP5 | |
| 12. | FA2BG2S1 | GP19 | |
| | A2 | GP2 | |
| 13. | A2B | GP3 | |
| 14. | FA2G0 | GP4/5 | |
| 15. | A2G1[6] | GP6/7 | |
| 16. | A2G1[3] | GP6/7 | |
| 17. | FA2BG0 | GP6/7 | |
| 18. | A2BG1 | GP8a | |
| 19. | FA2G1[6] | GP$_{8a/b}$ | |

Figure 24B

| 20. | FA2G1[3] | GP9 |  |
|---|---|---|---|
| 21. | FA2BG1[6] | GP10 |  |
| | A2G2 | GP12 |  |
| 22. | FA2BG1[3] | GP$_{11/12}$ |  |
| 23. | A2BG2 | GP13 |  |
| 24. | FA2G2 | GP$_{13/14/15}$ |  |
| 25. | FA2BG2 | GP15 |  |

METHOD FOR THE ANALYSIS OF N-GLYCANS ATTACHED TO IMMUNOGLOBULIN G FROM HUMAN BLOOD PLASMA AND ITS USE

CROSS REFERENCE TO RELATED APPLICATIONS

This application is the U.S. National Phase Application of PCT/HR2014/000022, filed Jun. 11, 2014, which claims priority to Croatian Patent Application No. P20130568A, filed Jun. 20, 2013, the contents of such applications being incorporated by reference herein.

FIELD OF THE INVENTION

The Invention refers to the method for the analysis of N-glycans attached to immunoglobulin G from human blood plasma for the purpose of: more precise prediction of biological and/or chronological age of a person; possibility to monitor efficacy of methods that slow down the ageing process; possibility to monitor progression of diseases that are developed as a result of the ageing process advancement, like: inflammatory diseases (including atherosclerosis), autoimmune diseases, tumours, diabetes, arthritis, osteoporosis, and Alzheimer disease; as well as evaluation of the overall condition/health of a body.

TECHNICAL PROBLEM

The Invention solves technical problem of precise prediction of a human's biological age by means of quantitative analysis of two or more N-glycans attached to immunoglobulin G (IgG), out of the total of six of them that are most strongly correlated to age.

Moreover, the Invention solves the technical problem of possibility to efficiently monitor efficacy of methods that slow down the ageing process; possibility to monitor progression of diseases that are developed as a result of the ageing process advancement, like: inflammatory diseases (including atherosclerosis), autoimmune diseases, tumours, diabetes, arthritis, osteoporosis, and Alzheimer disease; as well as evaluation of the overall condition/health of a body.

PREVIOUS STATE OF ART

Glycans are complex carbohydrates that are frequently attached to proteins and are involved in numerous physiological and pathological processes. Due to their involvement in a great number of biological processes, their diagnostic potential as biomarkers of overall health and the process of ageing is pronounced.

Immunoglobulin G (IgG) is the most abundant antibody in human blood plasma and has an important role in a body's defence against various antigens. Immunoglobulin G (IgG) is a glycoprotein and glycans attached to heavy chains of IgG molecules are crucial for its stability and function. IgG glycosylation depends on different physiological (age, sex, pregnancy) and pathological conditions (tumours, infections, autoimmune diseases).

Ageing is a biological process accompanied by numerous changes on molecular level and its mechanism has still been largely unknown. Biological age is the result of various genetic and environmental factors and it does not necessarily coincide with chronological (calendar) age of an individual. Exactly due to these reasons, biological age is better indicator of health and overall condition of a body, as well as of life expectancy than chronological age. Because of complexity of the very process of ageing, there is no one parameter that could alone determine biological age of an individual.

Several earlier studies have shown that the composition of IgG N-glycans is changing with age and depends on sex. Therefore, analysis of IgG glycans may bring to conclusions about biological age of an individual. In this respect, Parekh and associates were the first to describe lowered level of galactosylation of IgG glycans with advancement of age, see reference:

(1) R. Parekh, I. Roitt, D. Isenberg, R. Dwek, T. Rademacher: Age-related galactosylation of the N-linked oligosaccharides of human serum IgG, *J. Exp. Med.* 167 (1988) 1731-1736.

Subsequently, it has been noticed that the change of galactosylation with advancement of age is also sex specific, as well as that the level of bisecting N-acetylglucosamine (GlcNAc) also changes with age:

(2) L. Ruhaak, H.-W. Uh, M. Beekman, C. A. M. Koeleman, C. H. Hokke, R. G. J. Westendorp, M. Wuhrer, J. J. Houwing-Duistermaat, P. E. Slagboom, A. M. Deelder: Decreased Levels of Bisecting GlcNAc Glycoforms of IgG Are Associated with Human Longevity, *PLOS One* 5 (2010) e12566;

(3) K. Shikata, T. Yasuda, F. Takeuchi, T. Konishi, M. Nakada, T. Mizuochi: Structural changes in the oligosaccharide moiety of human IgG with ageing, *Glycoconjugate J.* 15 (1998) 683-689; and (4) E. Yamada, Y. Tsukamoto, R. Sasaki, K. Yagyu, N. Takahashi: Structural changes of immunoglobulin G oligosaccharides with age in healthy human serum, *Glycoconjugate J.* 14 (1997) 401-405.

Moreover, in an extensive study on IgG glycans it has been shown that reduced level of non-galactosylated glycans without bisecting N-acetylglucosamine represents an early marker for longevity, see reference 2.

Inventors of the said Invention published results of the analysis of variability of IgG N-glycans in isolated human populations earlier. At that time, previously reported relation (reference 1) between decreased IgG galactosylation in ageing was confirmed, and relation between IgG glycans analysis and prediction of ageing was indicated, see reference:

(5) M. Pučić, A. Knežević, J. Vidič, B. Adamczyk, M. Novokmet, O. Polašek, O. Gornik, S. Šupraha-Goreta, M. R. Wormald, I. Redžić, H. Campbell, A. Wright, N. D. Hastie, J. F. Wilson, I. Rudan, M. Wuhrer, P. M. Rudd, D. Josić, G. Lauc: High Throughput Isolation and Glycosylation Analysis of IgG-Variability and Heritability of the IgG Glycome in Three Isolated Human Populations, *Molecular & Cellular Proteomics* 10.1074/mcp.M111.010090.

As the closest prior art of the Invention one can identify:

(6) L. R. Ruhaak, H.-W. Uh, M. Beekman, C. H. Hokke, R. G. J. Westendorp, J. Honwing-Duistermaat, M. Wuhrer, A. M. Deelder, P. E. Slagboom: Plasma protein N-glycan profiles are associated with calendar age, familial longevity and health, *J. Proteome Res.* 10 (2011) 1667-1674;

which describes the method for the analysis of N-glycans attached to IgG from blood serum with purpose to predict longevity and healthy ageing, in other words prediction of diseases linked to ageing. Furthermore, the work confirms earlier statements that IgG galactosylation IgG decreases with age. With this, relation between ageing process and portion of galactosylated IgG has been indicated and there is an instruction that reduced level of non-galactosylated glycoforms that contain bisecting GlcNAc is an early sign of longevity.

Yamada and associates described the procedure of diagnosing nephropathy, rheumatism (arthritis), atopic dermatitis, diabetes and liver diseases via HPLC or a similar analysis of glycans attached to immunoglobulin G (IgG), see reference:

(7) JPH09257790A: E. Yamada, H. Nakagawa, R. Takahashi, Y. Tsukamoto, K. Kawamura, K. Oguri, A. Iwata: Diagnosis supporting method; Nakano Vinegar Co. Ltd. i A. Iwata (JP).

Also, Miyoshi and associates have discovered a diagnostic method for monitoring pancreatic cancer by means of analysing fucosylated N-glycans from haptoglobin from a biological sample that also included blood serum. This document also indicates possibility to diagnose cancer by means of analysing glycans, released from a glycoprotein, characteristic for that certain kind of tumour, see reference:

(8) US2009/181461A1: E. Miyoshi, N. Taniguchi, M. Nakano: Tumour marker for pancreatic cancer and method for testing the same; Wako Pure Chem. Ind. Ltd. (JP).

The Invention reveals a new method for analysis of N-glycans attached to immunoglobulin G (IgG) from human blood plasma, as well as usage of this method in: prediction of biological age of an individual; monitoring efficacy of methods that slow down the ageing process; monitoring progression of diseases that are developed as a result of the ageing process advancement, like: inflammatory diseases (including atherosclerosis), autoimmune diseases, tumours, diabetes, arthritis, osteoporosis, and Alzheimer disease; as well as evaluation of the overall condition/health of a body.

SUMMARY OF THE INVENTION

The Invention reveals a new method for the quantitative analysis of N-glycans attached to immunoglobulin G (IgG) from blood plasma of an individual, in which:

(a) relative abundance of two or three IgG N-glycans is determined, out of six characteristic ones: F(6)A2 (GP4), F(6)A2B (GP6), F(6)A2[6]G1 (GP8), F(6)A2G2 (GP14), F(6)A2BG2 (GP15), and F(6)A2G2S1 (GP18), that are most strongly correlated to age; or matching N-glycopeptides (glycoforms), obtained by digesting IgG with help of trypsine enzyme;

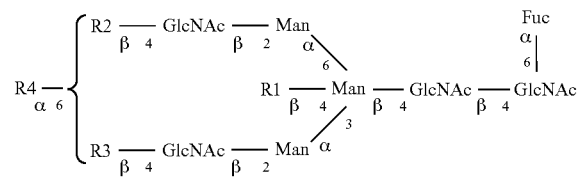

F(6)A2 (GP4): R1, R2, R3, R4=H
F(6)A2B (GP6): R1=GlcNAc; R2, R3, R4=H
F(6)A2[6]G1 (GP8): R1, R3, R4=H; R2=Gal
F(6)A2G2 (GP14): R1=H; R2, R3=Gal; R4=H
F(6)A2BG2 (GP15): R1=GlcNAc; R2, R3=Gal; R4=H
F(6)A2G2S1 (GP18): R1=H; R2, R3=Gal; R4=NeuAc
GlcNAc=N-acetylglucosamine
Fuc=fucose
Man=mannose
NeuAc=N-acetylneuraminic acid
Gal=galactose (b) results of a study on the relation of the mentioned six characteristic IgG glycans and chronologic (calendar) age and sex, previously carried out on large isolated human populations, are applied;

and comparing (a) and (b) the following informations are obtained:

I) precise prediction of biological age;
II) possibility to monitor efficacy of methods that slow down the ageing process;
III) possibility to monitor progression of diseases that are developed as a result of the ageing process advancement, like: inflammatory diseases (including atherosclerosis), autoimmune diseases, tumours, diabetes, arthritis, osteoporosis, and Alzheimer disease; and
IV) evaluation of the overall condition/health of a body, related to ageing.

BRIEF DESCRIPTION OF FIGURES

The Invention is described by the following figures:

FIGS. 24A-24C. Illustrate structures of IgG glycans that are visible by capillary electrophoresis (CE) technique, carried out under the conditions as described in Example 8.

DETAILED DESCRIPTION

Figure 1:
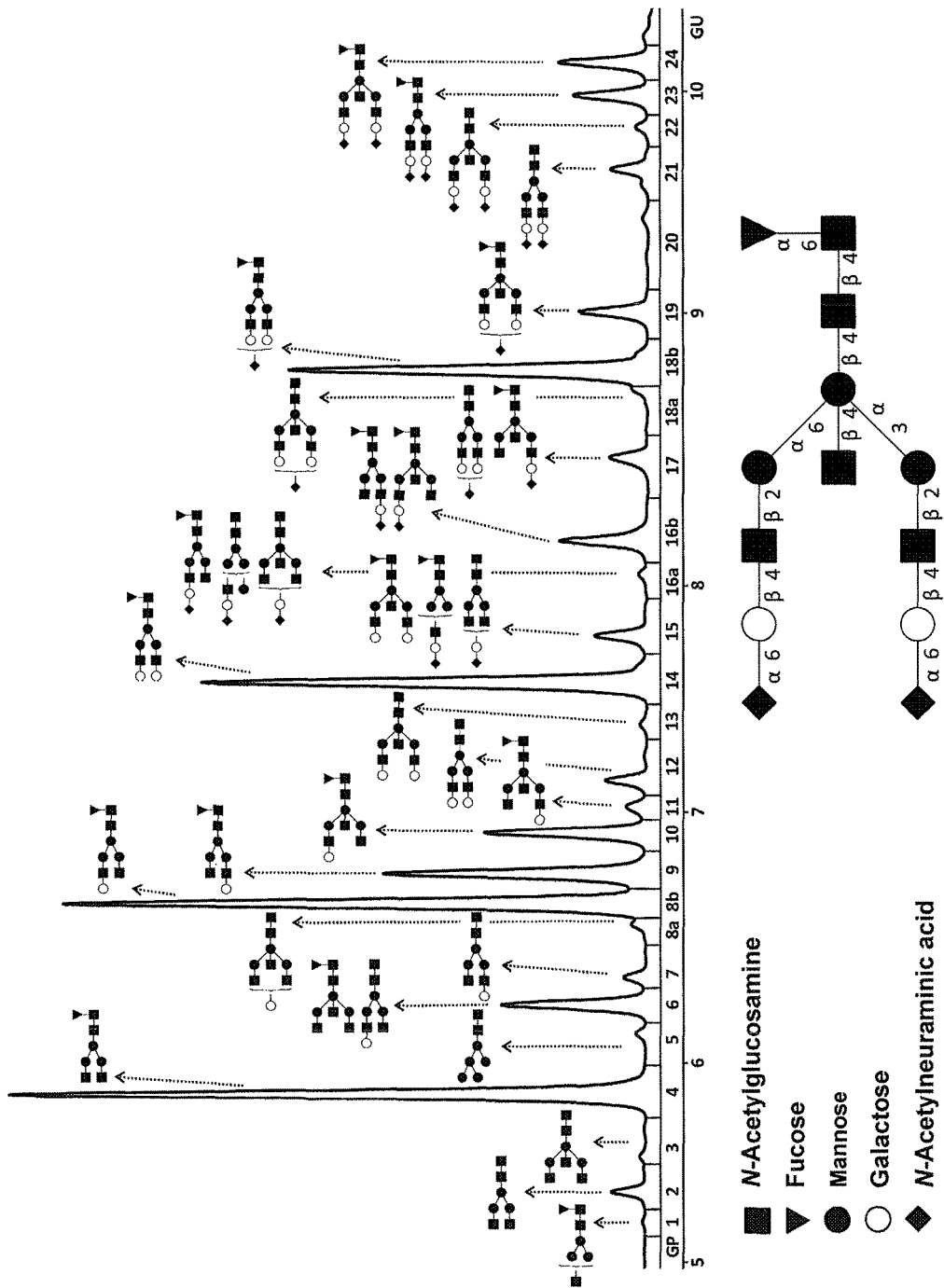
FIG. 1. Typical chromatogram obtained by the quantitative analysis of IgG N-glycans by ultra performance liquid chromatography (UPLC).
Figure 2A:
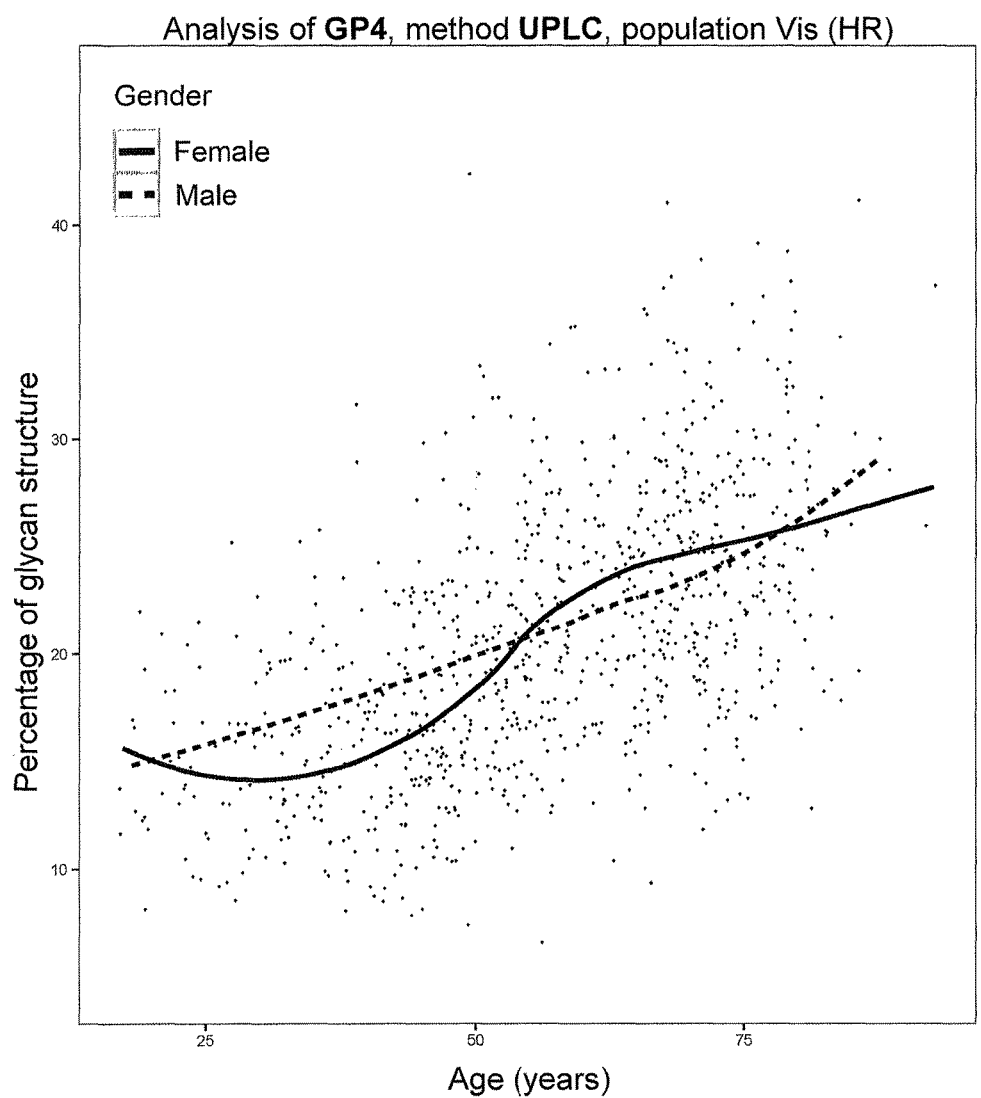
FIG. 2A. Change in the abundance of glycan F(6)A2 (GP4) with age among women (continuous line) and men (dashed line) in the population of Vis island (HR), determined by ultra performance liquid chromatography (UPLC).
Figure 2B:
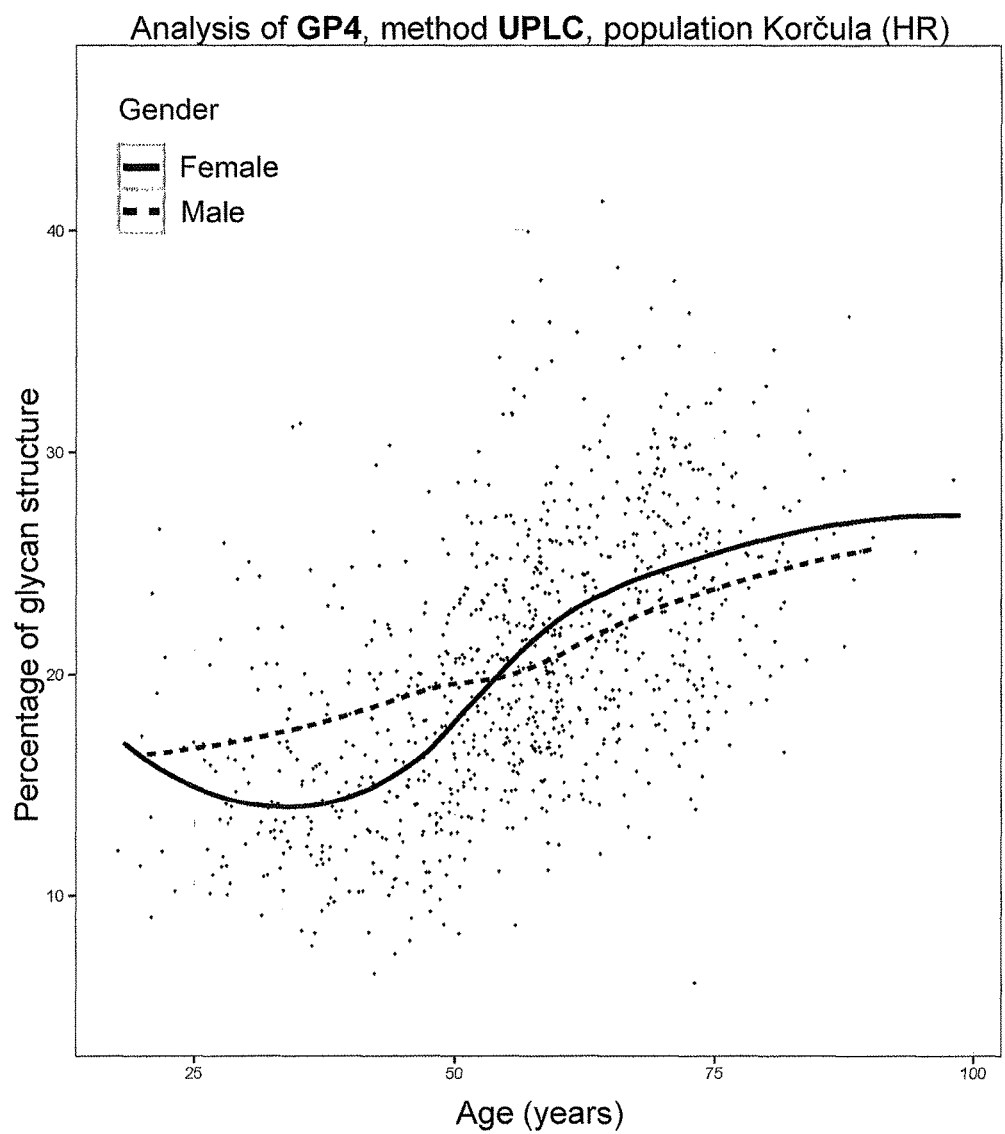
FIG. 2B. Change in the abundance of glycan F(6)A2 (GP4) with age among women (continuous line) and men (dashed line) in the population of Korčula island (HR), determined by ultra performance liquid chromatography (UPLC).
Figure 2C:
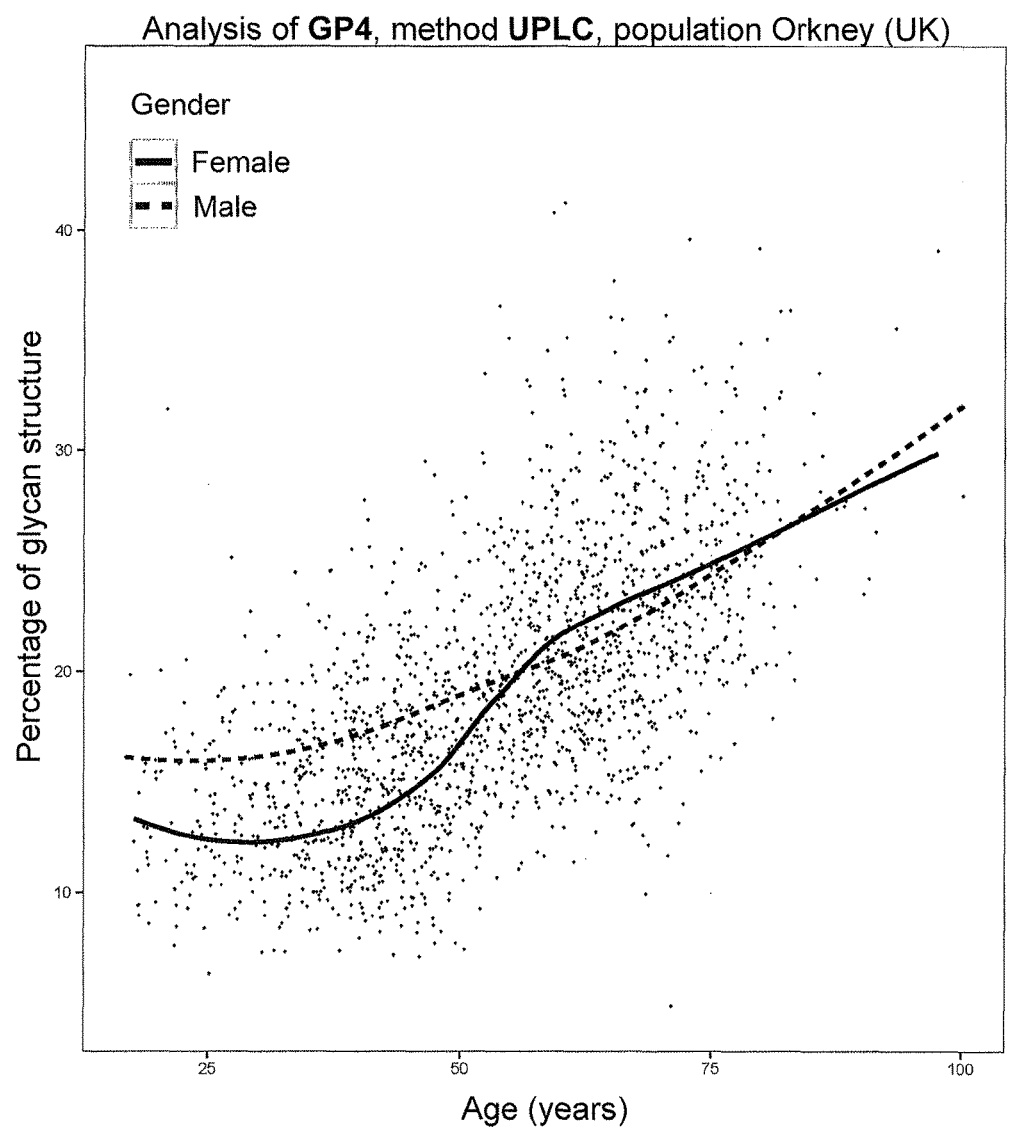
FIG. 2C. Change in the abundance of glycan F(6)A2 (GP4) with age among women (continuous line) and men (dashed line) in the population of Orkney Isles (UK), determined by ultra performance liquid chromatography (UPLC).
Figure 3A:
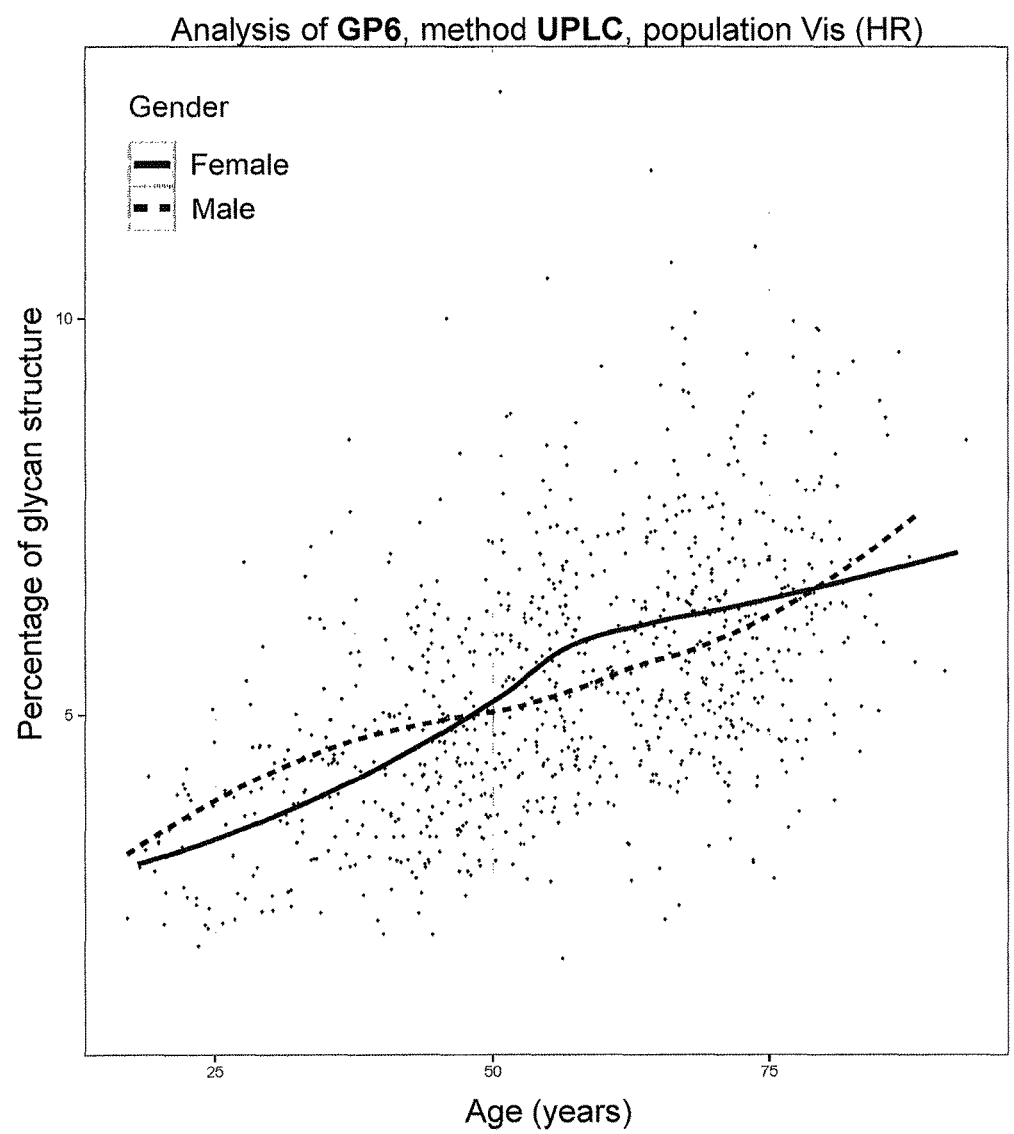
FIG. 3A. Change in the abundance of glycan F(6)A2B (GP6) with age among women (continuous line) and men (dashed line) in the population of Vis island (HR), determined by ultra performance liquid chromatography (UPLC).
Figure 3B:
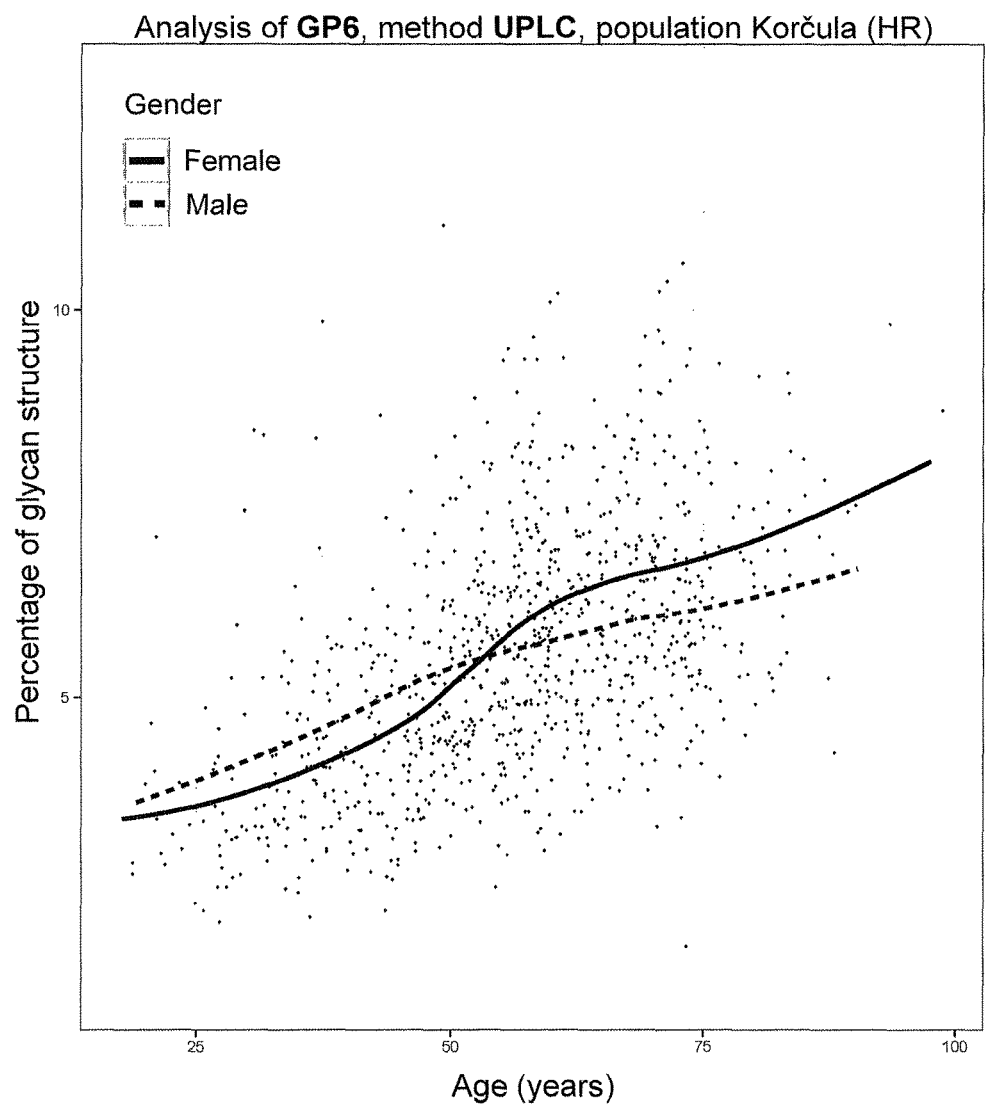
FIG. 3B. Change in the abundance of glycan F(6)A2B (GP6) with age among women (continuous line) and men (dashed line) in the population of Korčula island (HR), determined by ultra performance liquid chromatography (UPLC).
Figure 3C:
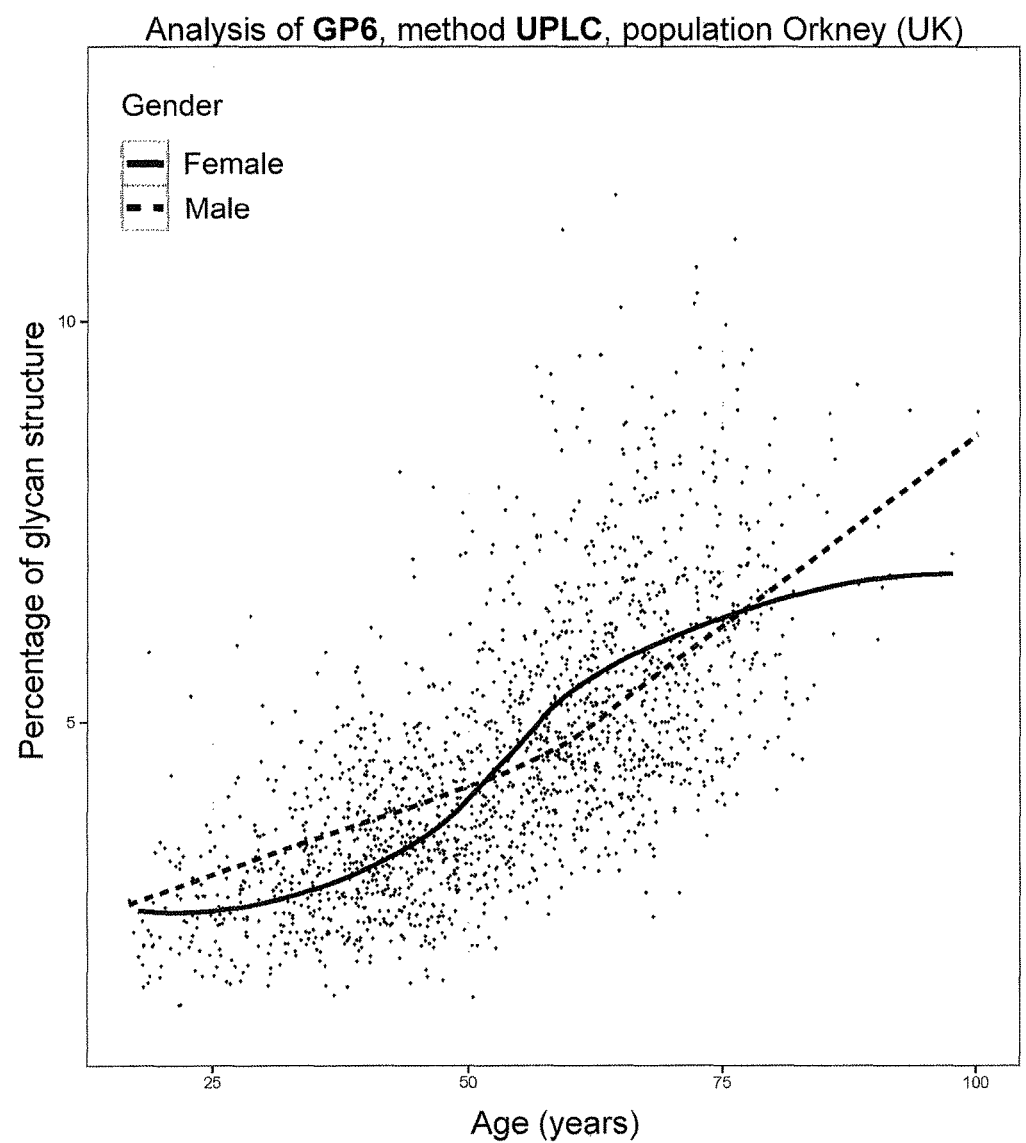
FIG. 3C. Change in the abundance of glycan F(6)A2B (GP6) with age among women (continuous line) and men (dashed line) in the population of Orkney Isles (UK), determined by ultra performance liquid chromatography (UPLC).
Figure 4A:
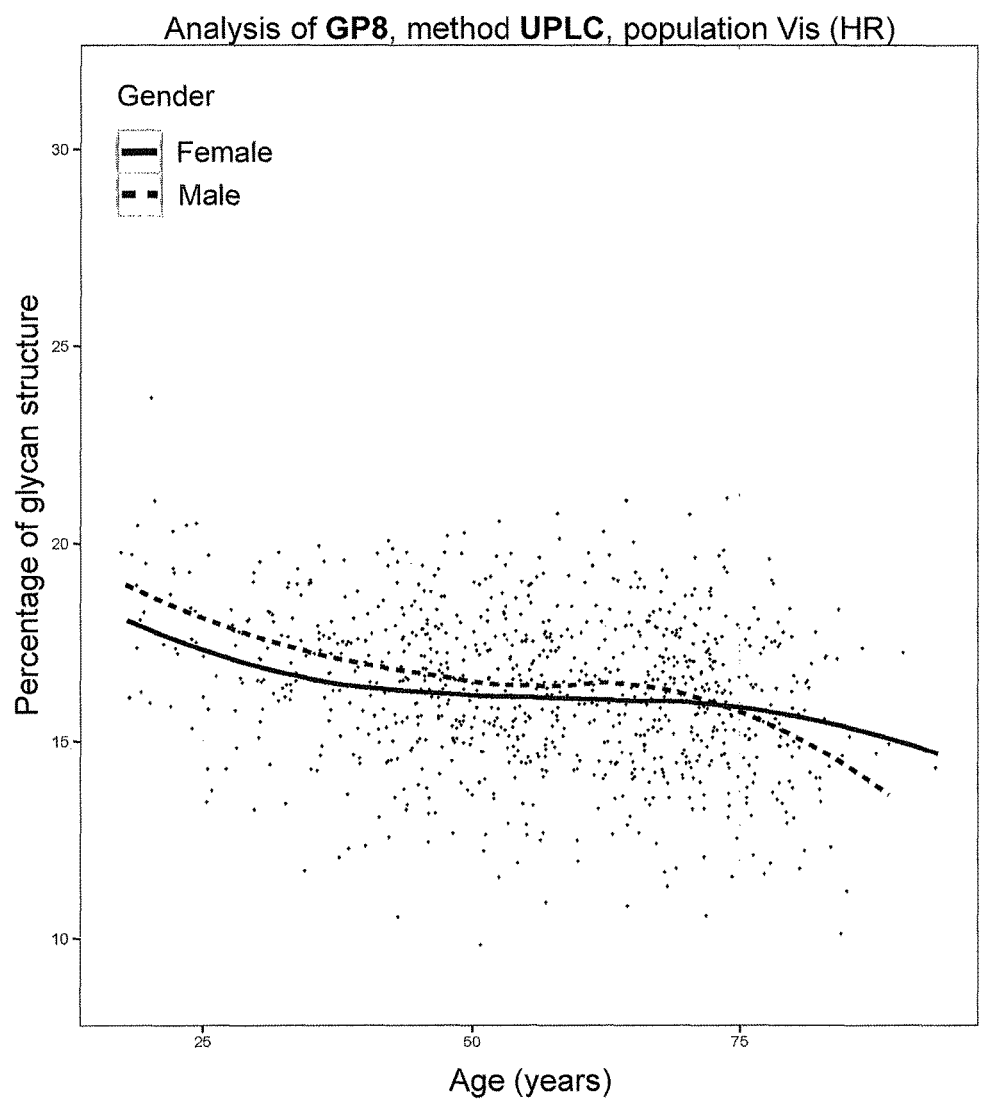
FIG. 4A. Change in the abundance of glycan F(6)A2[6]G1 (GP8) with age among women (continuous line) and men (dashed line) in the population of Vis island (HR), determined by ultra performance liquid chromatography (UPLC).
Figure 4B:
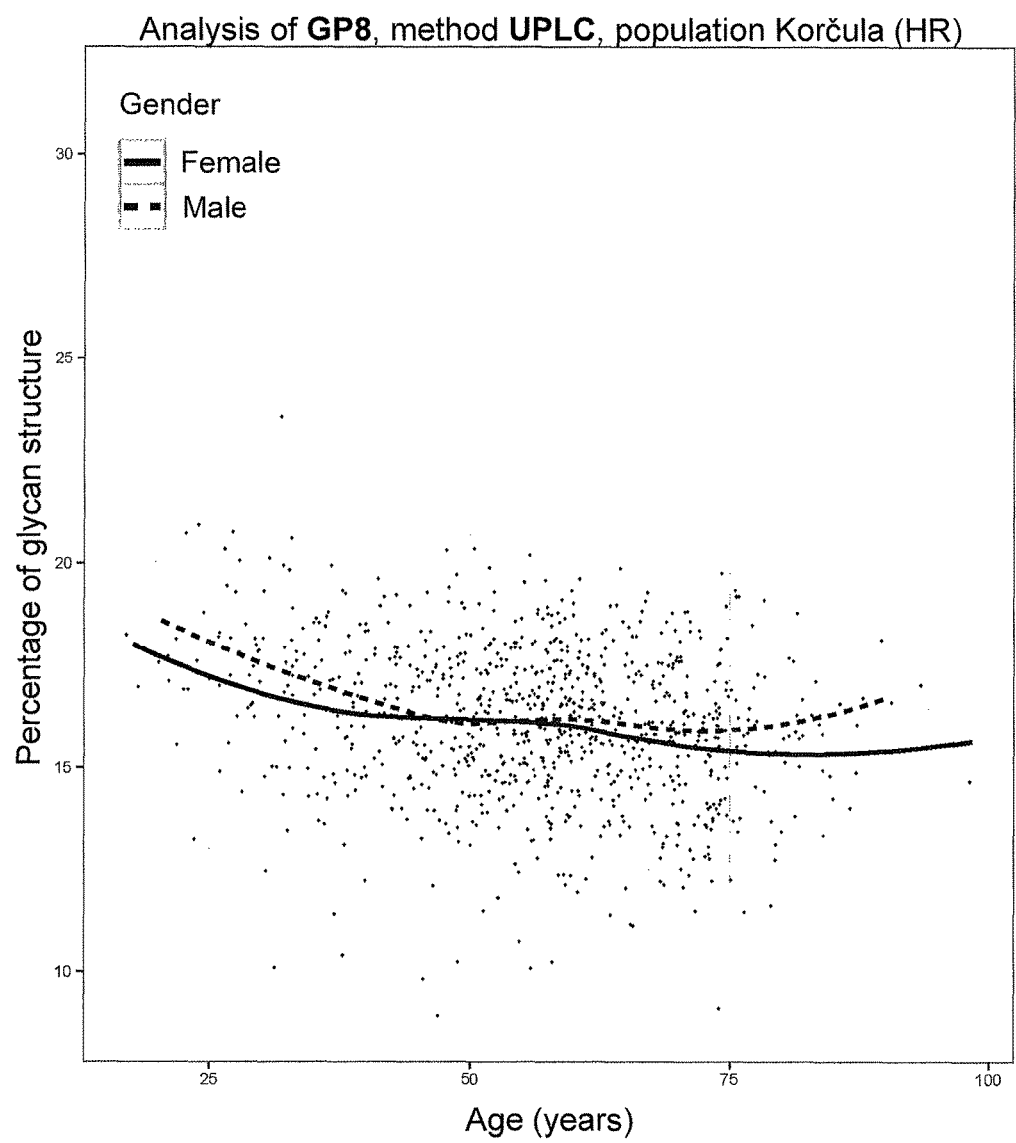
FIG. 4B. Change in the abundance of glycan F(6)A2[6]G1 (GP8) with age among women (continuous line) and men (dashed line) in the population of Korčula island (HR), determined by ultra performance liquid chromatography (UPLC).
Figure 4C:
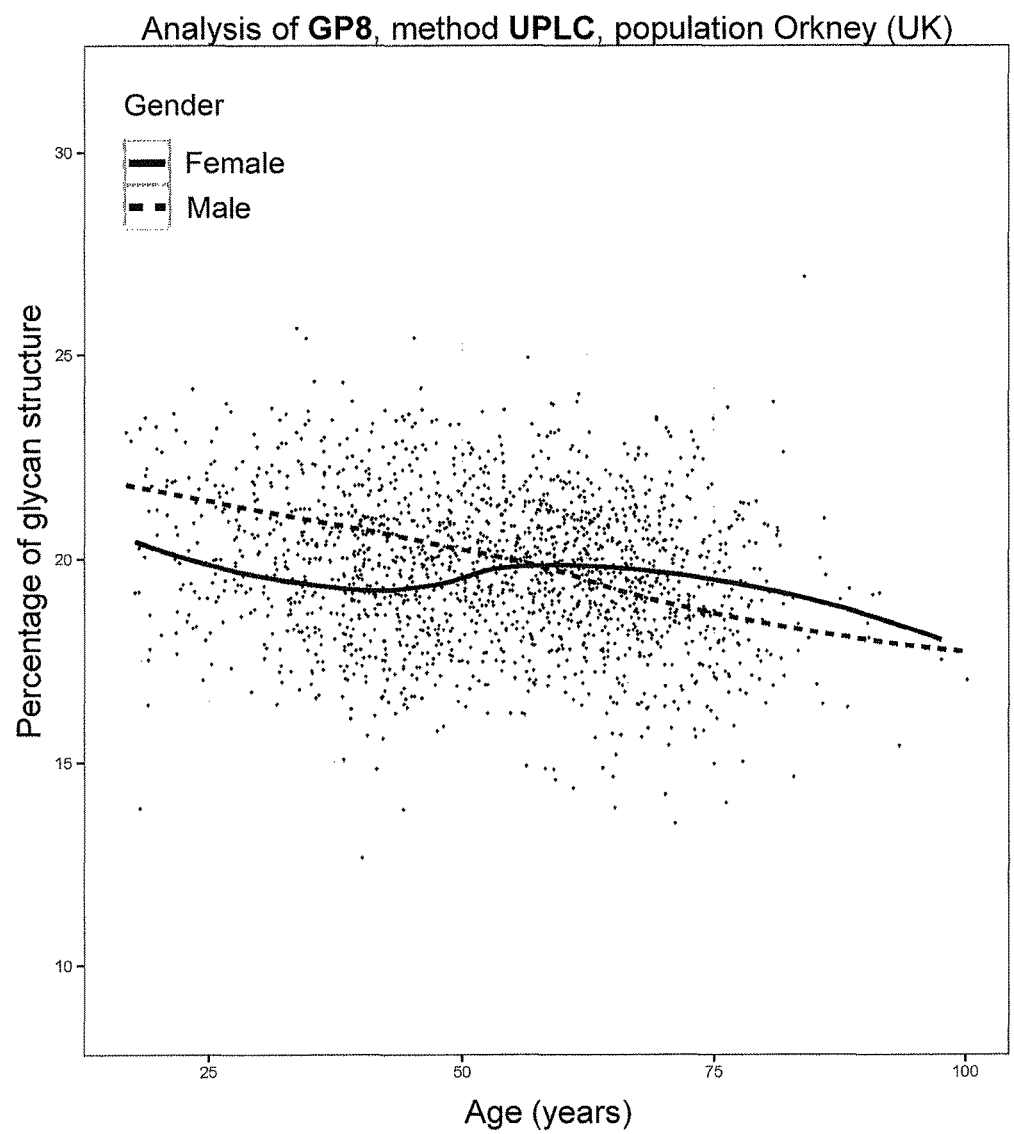
FIG. 4C. Change in the abundance of glycan F(6)A2[6]G1 (GP8) with age among women (continuous line) and men (dashed line) in the population of Orkney Isles (UK), determined by ultra performance liquid chromatography (UPLC).
Figure 5A:
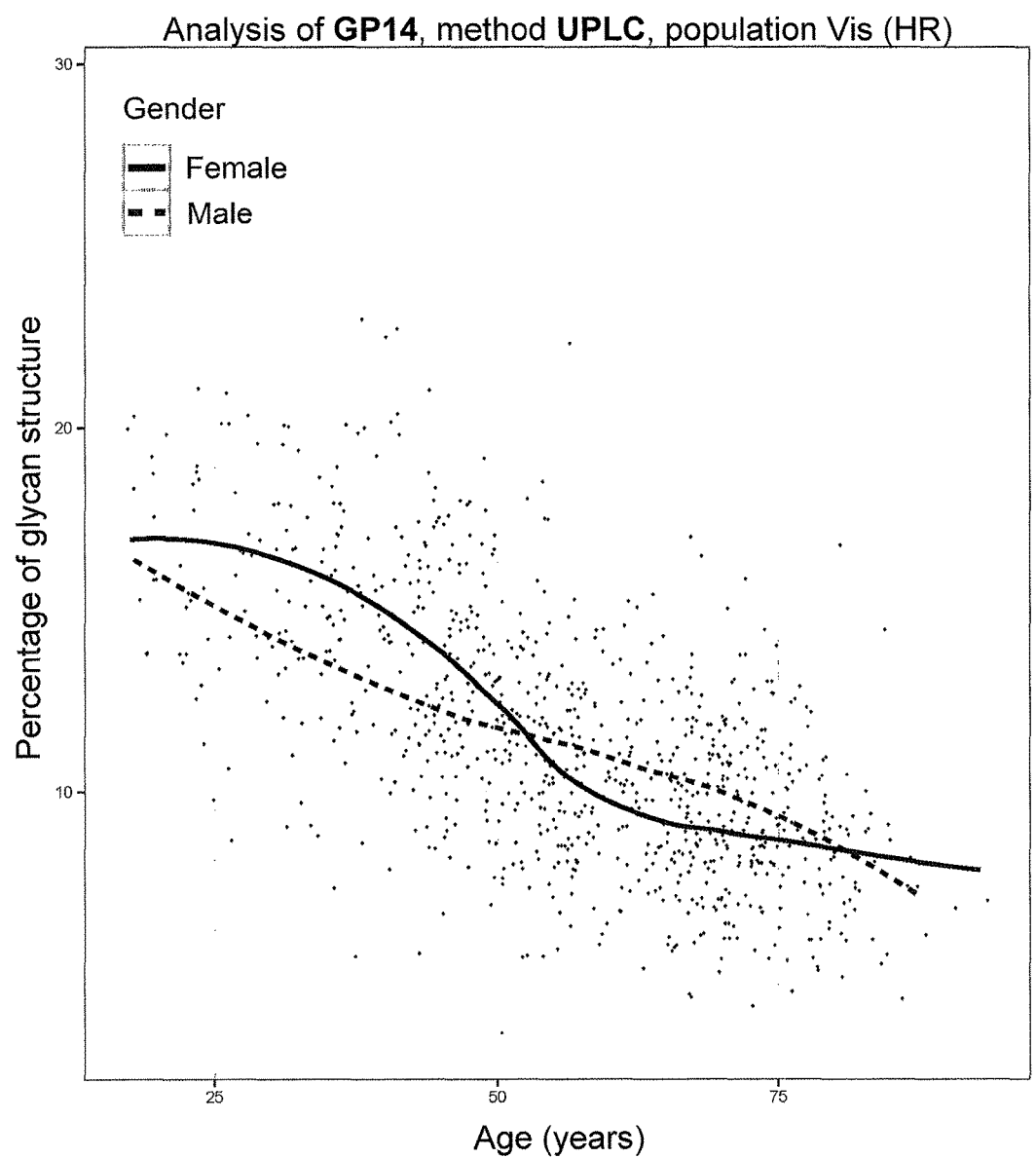
FIG. 5A. Change in the abundance of glycan F(6)A2G2 (GP14) with age among women (continuous line) and men (dashed line) in the population of Vis island (HR), determined by ultra performance liquid chromatography (UPLC).
Figure 5B:
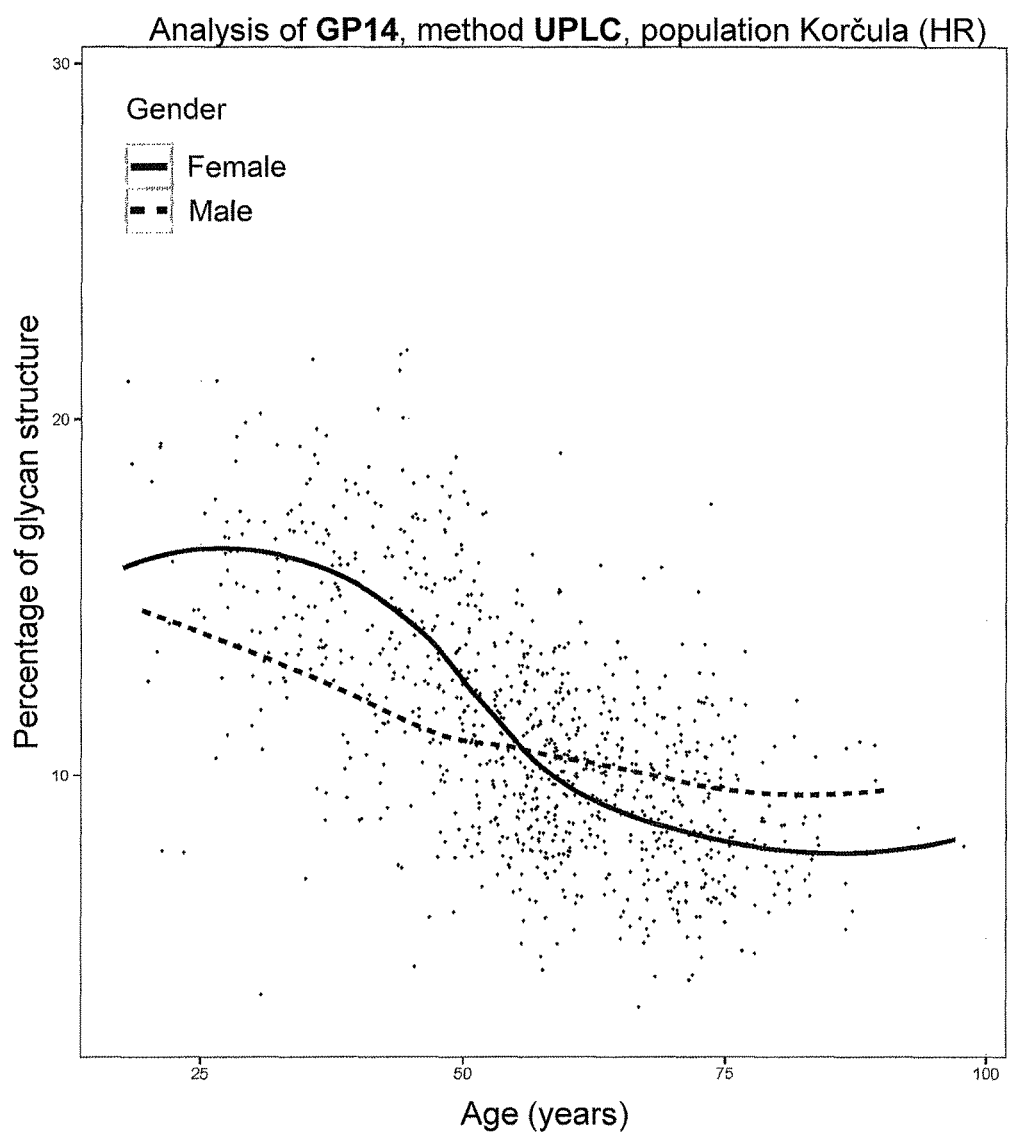
FIG. 5B. Change in the abundance of glycan F(6)A2G2 (GP14) with age among women (continuous line) and men (dashed line) in the population of Korčula island (HR), determined by ultra performance liquid chromatography (UPLC).
Figure 5C:
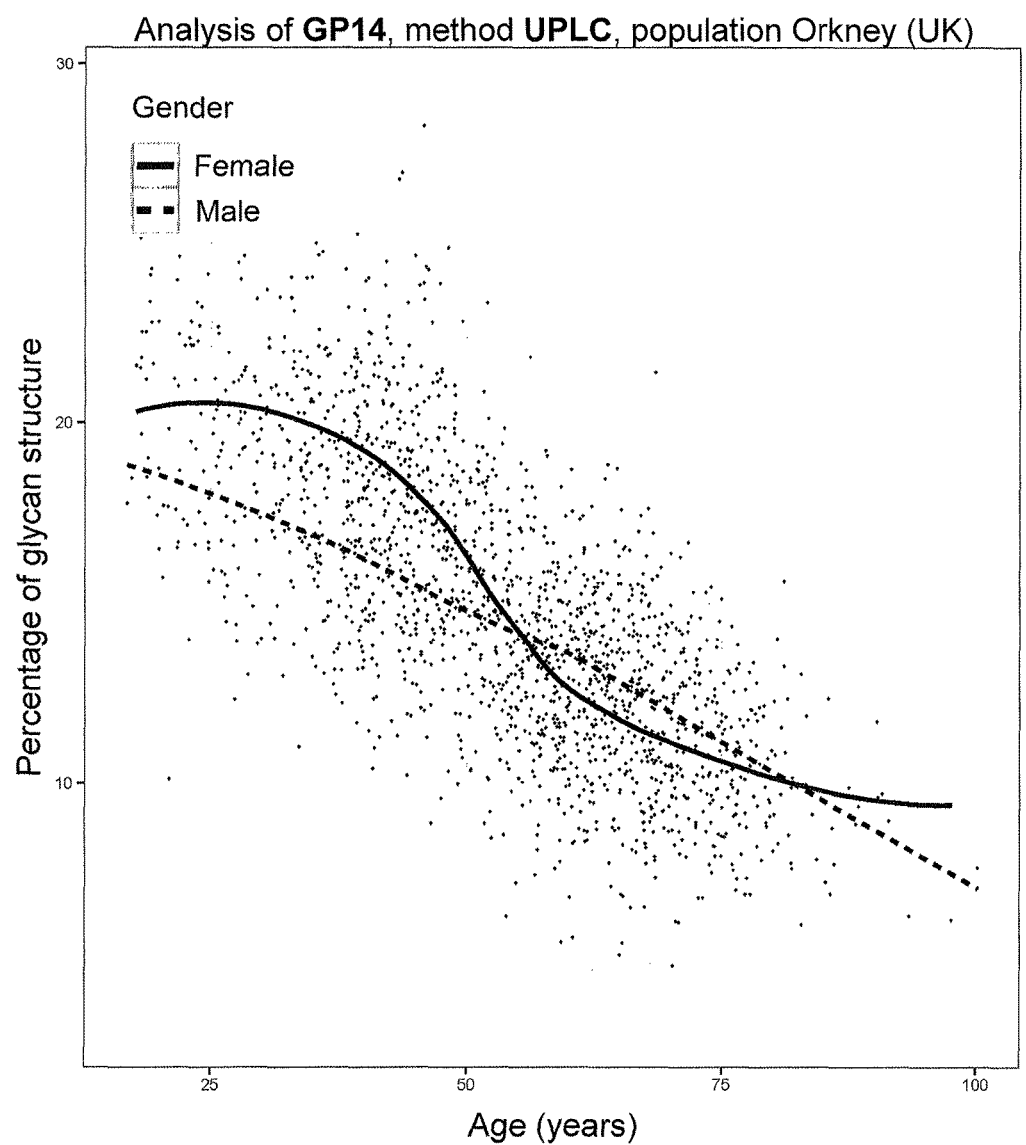
FIG. 5C. Change in the abundance of glycan F(6)A2G2 (GP14) with age among women (continuous line) and men (dashed line) in the population of Orkney Isles (UK), determined by ultra performance liquid chromatography (UPLC).
Figure 6A:
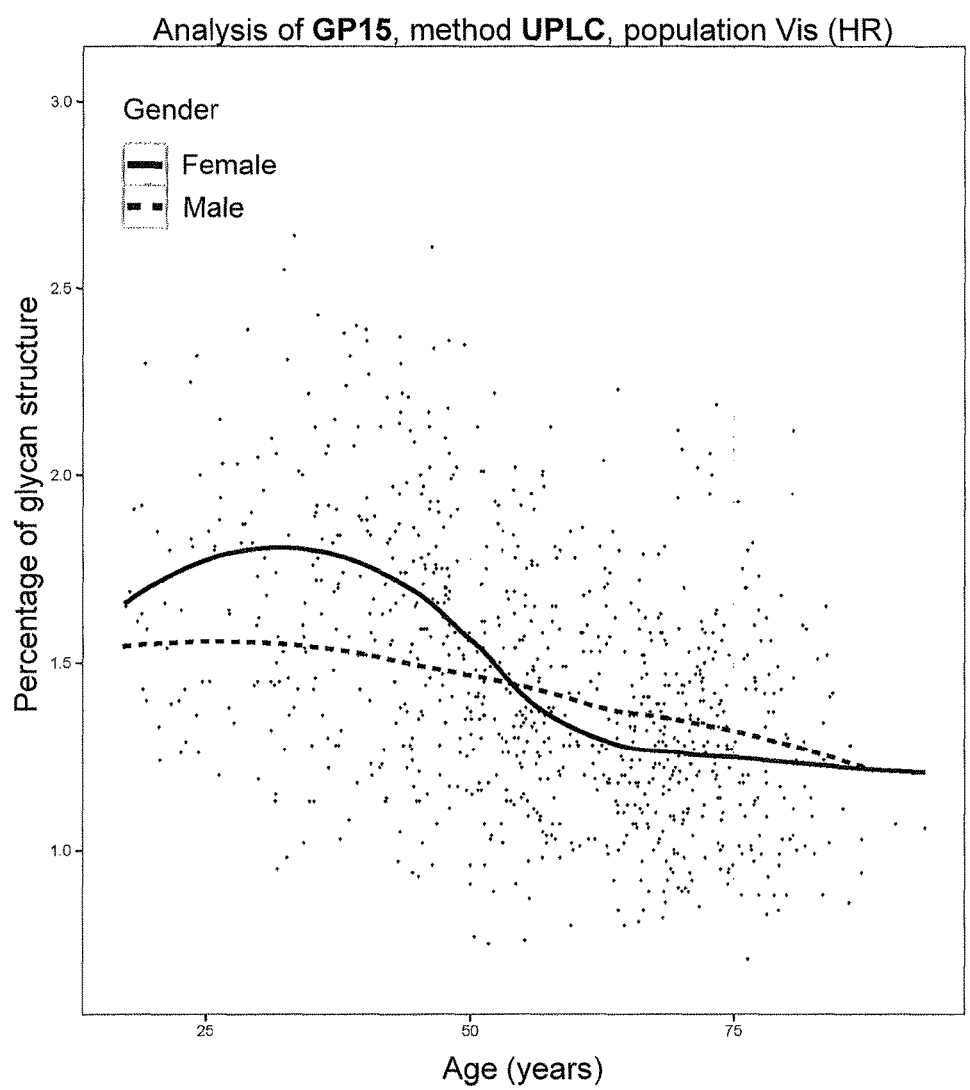
FIG. 6A. Change in the abundance of glycan F(6)A2BG2 (GP15) with age among women (continuous line) and men (dashed line) in the population of Vis island (HR), determined by ultra performance liquid chromatography (UPLC).
Figure 6B:
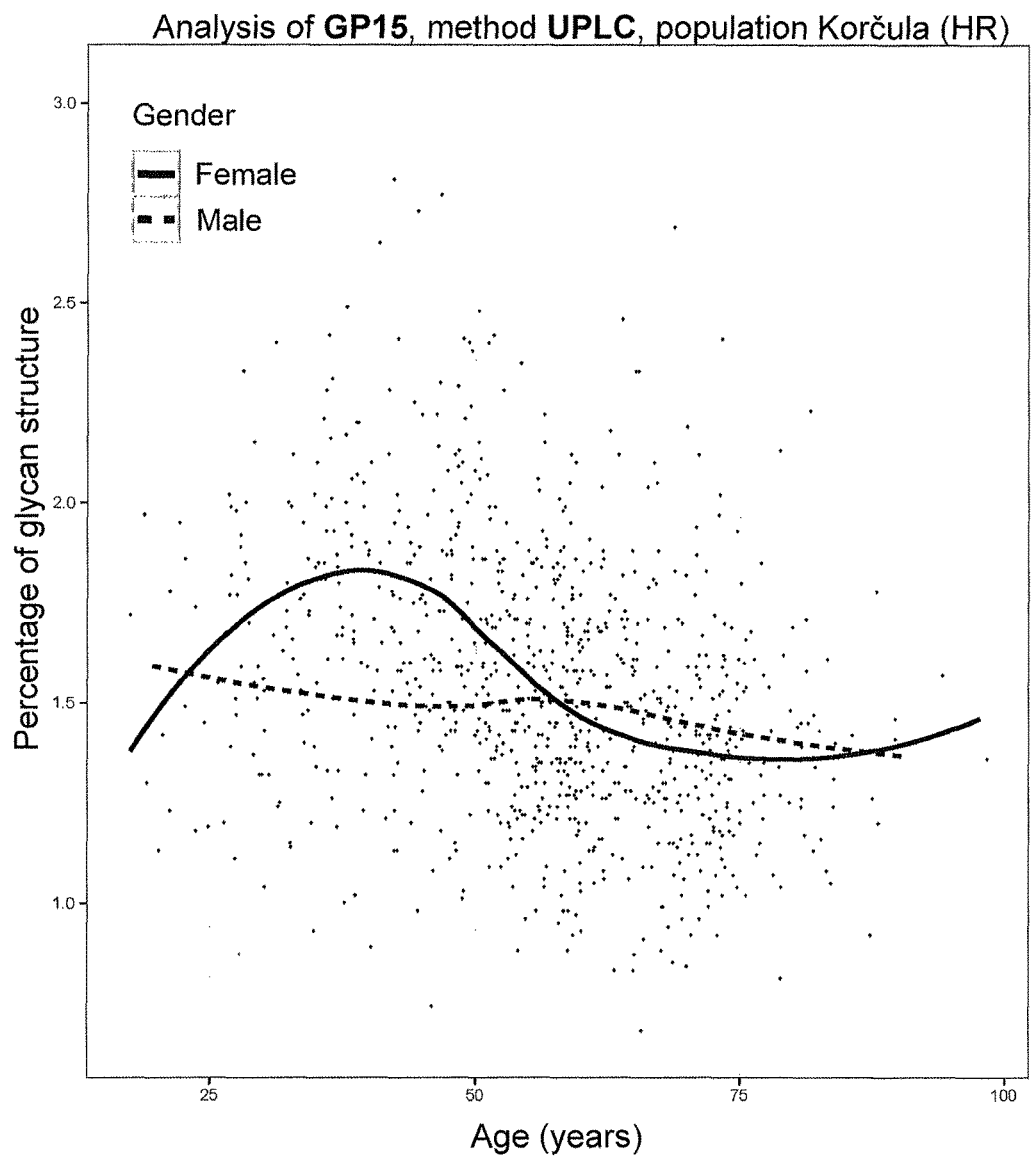
FIG. 6B. Change in the abundance of glycan F(6)A2BG2 (GP15) with age among women (continuous line) and men (dashed line) in the population of Korčula island (HR), determined by ultra performance liquid chromatography (UPLC).
Figure 6C:
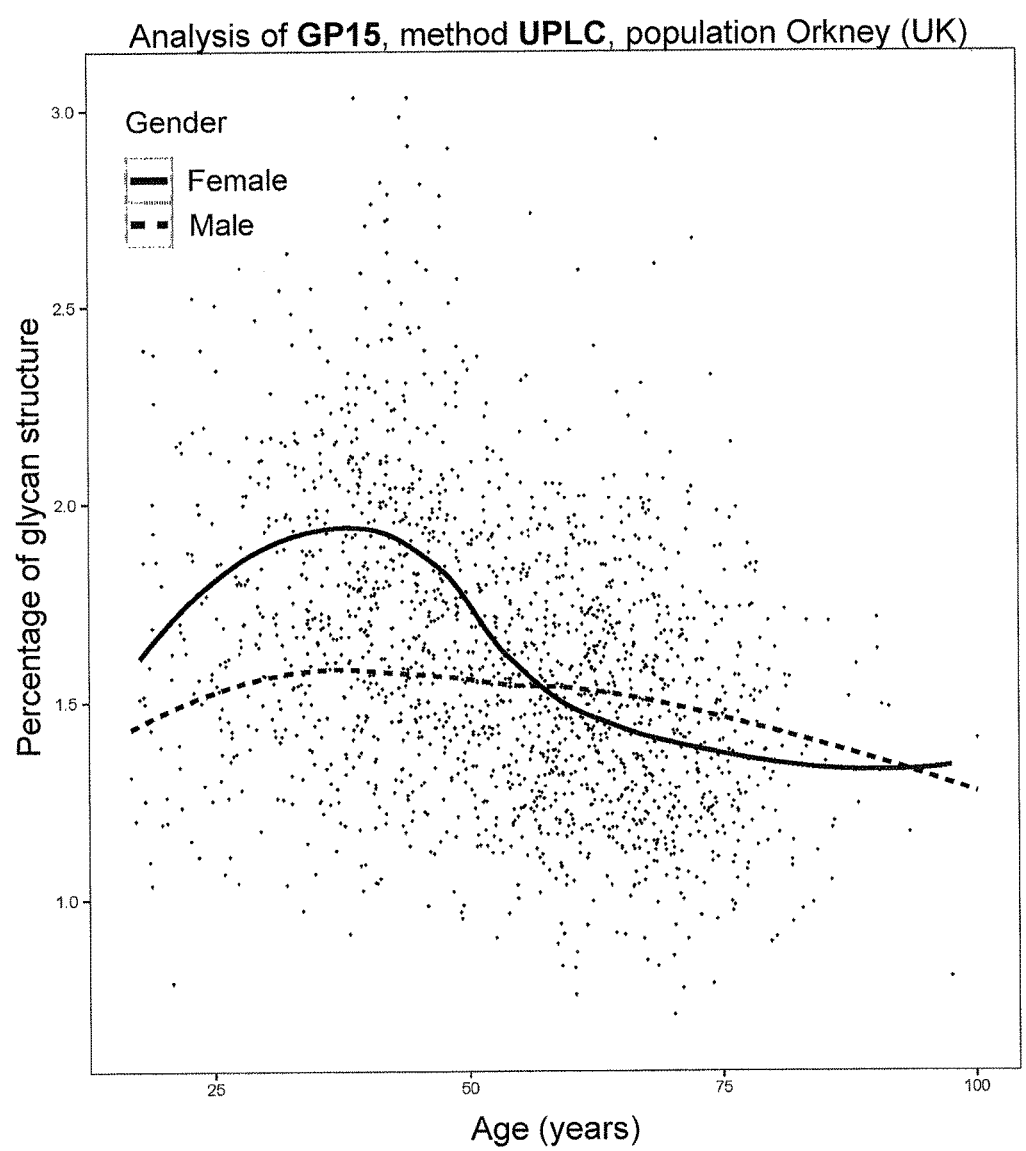
FIG. 6C. Change in the abundance of glycan F(6)A2BG2 (GP15) with age among women (continuous line) and men (dashed line) in the population of Orkney Isles (UK), determined by ultra performance liquid chromatography (UPLC).
Figure 7A:
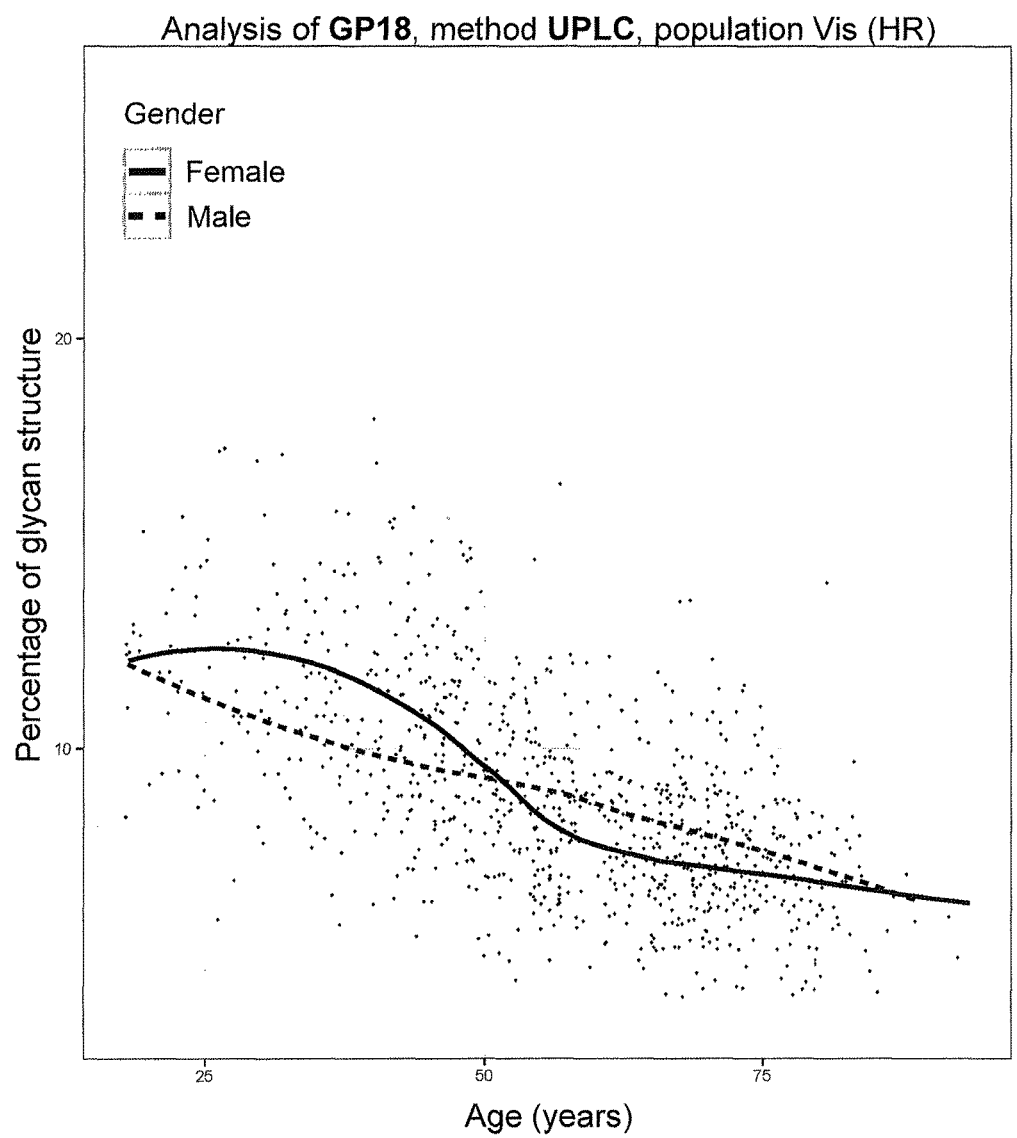
FIG. 7A. Change in the abundance of glycan F(6)A2G2S1 (GP18) with age among women (continuous line) and men (dashed line) in the population of Vis island (HR), determined by ultra performance liquid chromatography (UPLC).
Figure 7B:
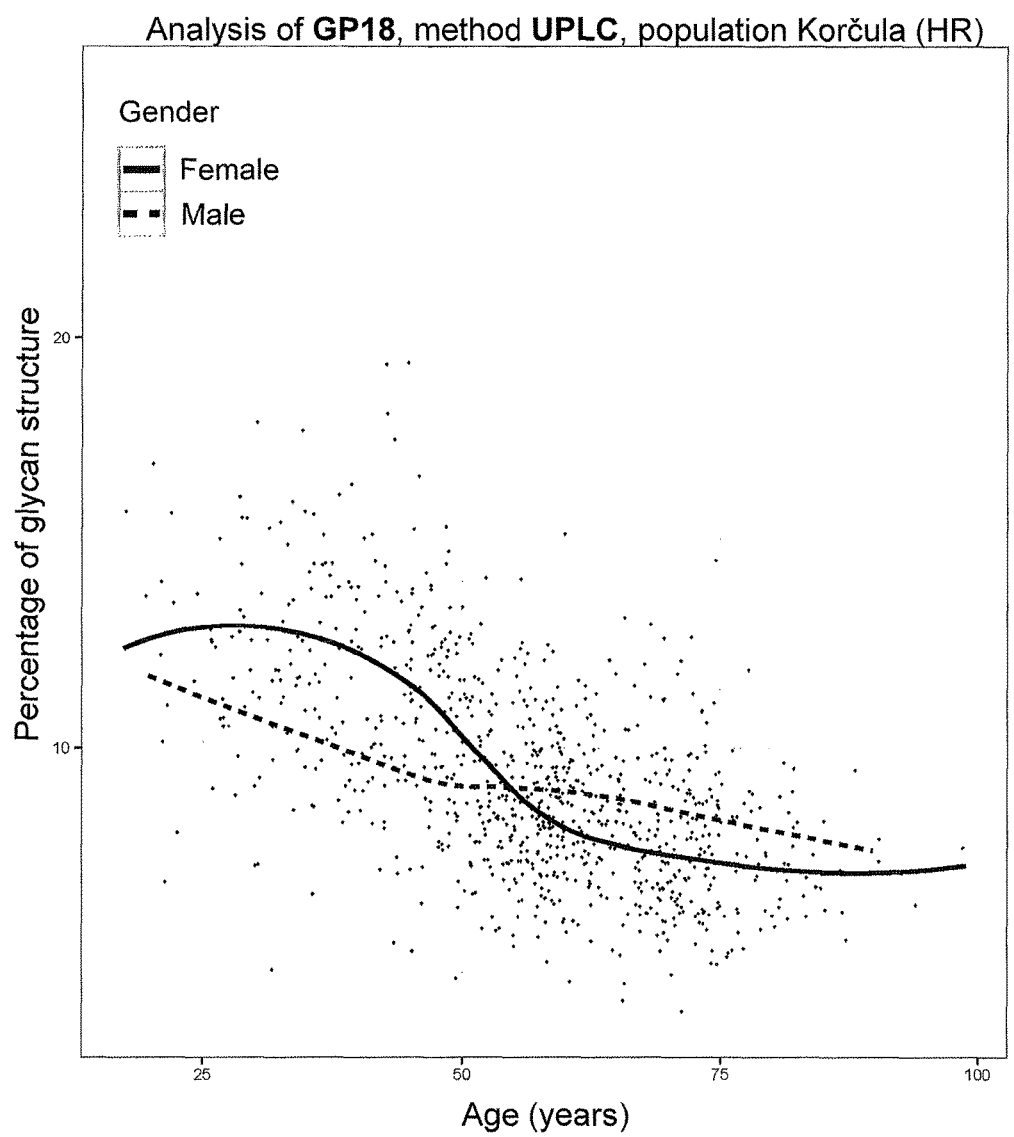
FIG. 7B. Change in the abundance of glycan F(6)A2G2S1 (GP18) with age among women (continuous line) and men (dashed line) in the population of Korčula island (HR), determined by ultra performance liquid chromatography (UPLC).
Figure 7C:
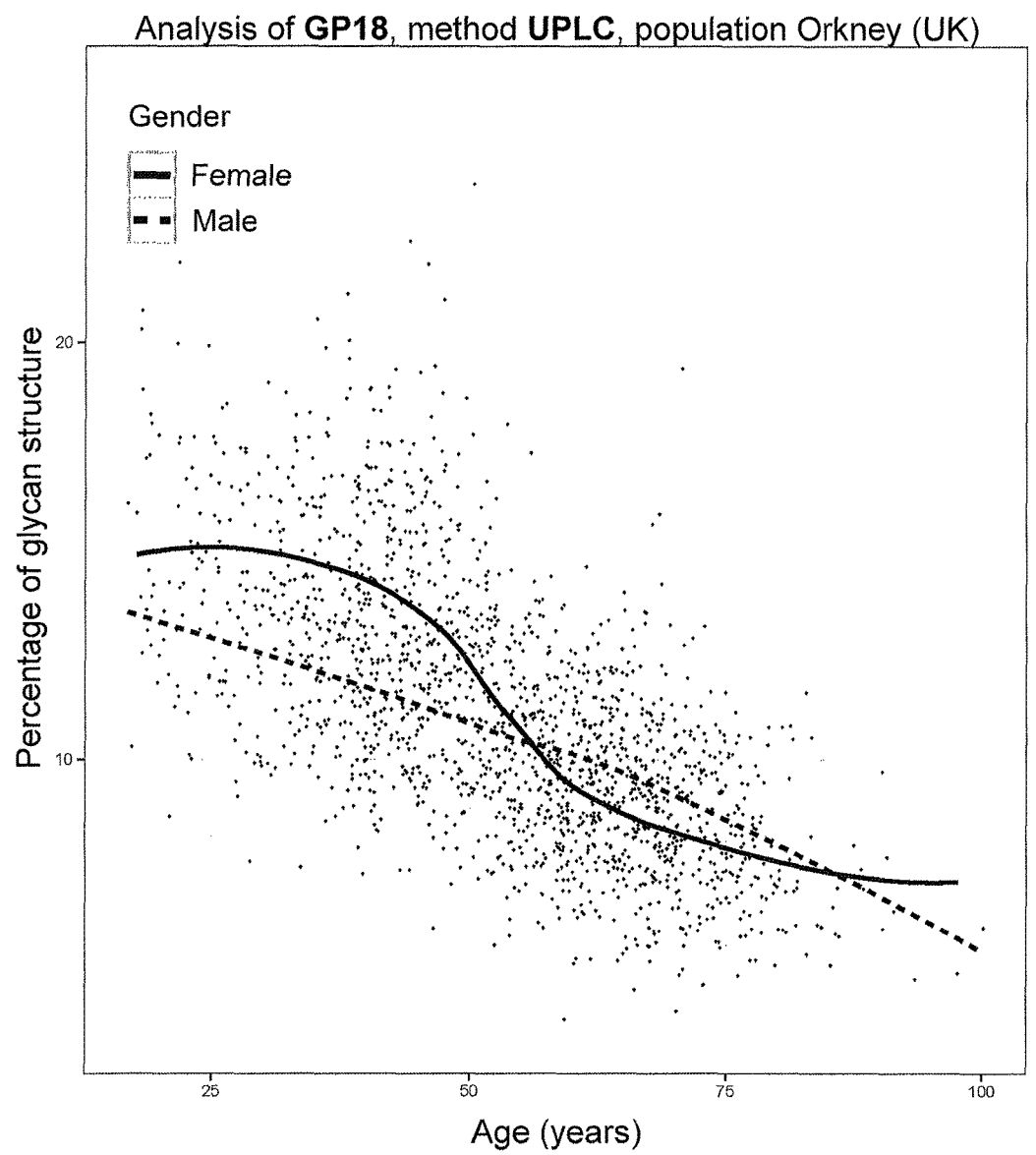
FIG. 7C. Change in the abundance of glycan F(6)A2G2S1 (GP18) with age among women (continuous line) and men (dashed line) in the population of Orkney Isles (UK), determined by ultra performance liquid chromatography (UPLC).

The Invention discloses a new method for the quantitative analysis of N-glycans attached to immunoglobulin G (IgG) from blood plasma of an individual in which:
(a) relative abundance of two or more IgG glycans is determined, out of six characteristic ones: F(6)A2 (GP4), F(6)A2B (GP6), F(6)A2[6]G1 (GP8), F(6)A2G2 (GP14), F(6)A2BG2 (GP15), and F(6)A2G2S1 (GP18), which are most strongly correlated to age; or matching N-glycopeptides (glycoforms) obtained by digesting IgG with help of trypsine enzyme;
(b) results of a study on the relation of the mentioned six characteristic IgG glycans and chronologic (calendar) age and sex, previously carried out on large isolated human populations, are applied;
and comparing (a) and (b) the following informations are obtained:
I) precise prediction of biological age;
II) possibility to monitor efficacy of methods that slow down the ageing process;
III) possibility to monitor progression of diseases that are developed as a result of the ageing process advancement, like: inflammatory diseases (including atherosclerosis), autoimmune diseases, tumours, diabetes, arthritis, osteoporosis, and Alzheimer disease; and
IV) evaluation of the overall condition/health of a body, related to ageing.

IgG N-glycans analysis among respondents from three different populations

IgG N-glycans analysis has been carried out among respondents from three different isolated populations: the island of Vis (Croatia/HR), the island of Korčula (Croatia/HR), and Orkney Isles (United Kingdom/UK). The population of Vis island included 890 respondents (521 women and 369 men), ranging in age from 18 to 93 (average age 56). The population of Korčula island included 915 respondents (595 women and 320 men), ranging in age from 18 to 98 (average age 56). The population of Orkney Isles included 1786 respondents (1082 women and 704 men), ranging in age from 16 to 100 (average age 54).

The Procedure of Carrying Out the Study

The study of N-glycans attached to immunoglobulin (IgG) in human blood plasma from isolated populations and the procedure for IgG glycans analysis in accordance with the invention include the following steps:
(i) taking blood sample of an individual in question and making record of that individual's sex;
(ii) isolation of blood plasma from blood;
(iii) purification of immunoglobulin G (IgG) with attached N-glycans by affinity chromatography with help of protein G attached to monolithic chromatography columns;
(iv) releasing glycans from the attachment to immunoglobulin G (IgG);
(v) treating the obtained sample with a mixture of favourable amine with ultraviolet absorbing group (so-called "fluorescent colour") and favourable reducing agent to fluorescently label released glycans by reductive amination;
(vi) quantitative analysis of such a prepared sample, which contains fluorescently-derivatized IgG glycans by means of a favourable analytical method; and
(vii) processing and interpretation of the results.

Alternatively, steps (iv) and (v) can be replaced with the procedure of treating the purified immunoglobulin G (IgG) with trypsin enzyme. Subsequently, released N-glycopeptides are purified by reverse phase solid-phase extraction (RP-SPE), with quantitative analysis of purified N-glycopeptides, i.e. glycoforms filtered in such a manner, which correspond to glycans characteristic for age.

Blood samples are taken in accordance to good clinical practice, by collecting blood in test tubes with anticoagulant, and it is instantly being processed by centrifugation in order to isolate blood plasma. Blood plasma is stored at −70° C., see previously mentioned reference (5). The purification of immunoglobulin G (IgG) that contains various attached glycans is described in Example 1.

Releasing glycans from their attachment to immunoglobulin G (IgG) is executed by a favourable method known from the background of the Invention: hidrazinolysis or enzyme reaction catalysed by peptide-N4-(N-acetyl-beta-glucosaminyl)asparagine amidase (PNGase F), see references (3) and (6). The procedure of releasing glycans from purified immunoglobulin G (gG) is described in Example 2.

Fluorescent labelling (derivatization) of glycans by reductive amination is executed with favourable amines which, in their structure, contain aromatic or other ultraviolet absorbing group. Aromatic amine that is used for fluorescent derivatization of glycans according to the invention has been chosen from a group that consists of: 2-aminobenzamide (2AB), 9-aminopyrene-1 3 6-trisulfonic acid (APTS), ethyl 4-aminobenzoate, 2-aminopyridine, anthranillic acid, and other amines as it is noted in the reference:
(9) A. Ceroni, K. Maass, H. Geyer, R. Geyer, A. Dell, S. M. Haslam: GlycoWorkbench: A Tool for the Computer-Assisted Annotation of Mass Spectra of Glycans, *J. Proteome Res.* 7 (2008) 1650-1659.

The reducing agent, used in the procedure of glycan derivatization with ultraviolet absorbing amines by reductive amination, is chosen from a group that consists of: 2-picoline borane (2-$CH_3C_5H_4N.BH_3$), sodium cyanoborohydride (NaBH$_3$CN), sodium triacetoxyborohydride [NaBH(CH$_3$COO)$_3$], or some other appropriate selective reducing agent.

The procedure of glycan derivatization by reductive amination is described in Example 3.

Quantitative analysis of derivatized glycans or glycopeptides has been executed by one of analytical techniques, chosen from a group that consists of: ultra performance liquid chromatography (UPLC), MALDI-TOF (matrix-assisted laser desorption/ionization time-of-flight) mass spectrometry, liquid chromatography-mass spectrometry (LC-MS), capillary electrophoresis (CE), or some other appropriate quantitative analytical technique.

The procedures of quantitative analysis of derivatized glycans or their glycopeptides are described in Example 4 (UPLC), Example 6 (MALDI-TOF), Example 7 (LC-MS), and Example 8 (CE).

As the result of quantitative analysis a chromatogram is obtained, or electropherogram with a series of peaks (signals) that represent fluorescently active derivates of one or more related glycans. Typical UPLC chromatogram of IgG glycans, derivatized by reductive amination reaction with 2-aminobenzamide (2AB) is shown in FIG. 1. Structures of all relevant IgG glycans are described in reference (5).

In case of MALDI-TOF analysis (Example 6) and LC-MS (Example 7), quantitative analysis includes analysis of glycopeptides, in other words glycoforms, which correspond to glycans characteristic for age and which are obtained by digesting IgG with help of trypsin enzyme with subsequent purification by reverse phase solid-phase extraction (RP-SPE). The procedure of enzyme digestion of IgG with trypsin and purification of the obtained glycopeptides, or glycoforms, that correspond to glycans GP4, GP6, GP8, GP14, GP15, and GP18 is described in Example 5.

Processing and Interpretation of the Results of Quantitative Analysis

Relative abundance of individual glycans attached to immunoglobulin G (IgG) (in the study on different isolated human populations, as well as in testing blood plasma of any human in accordance with the invention) is determined by normalization of the area underneath the signal (chromatographic peak) of a certain fluorescently derivatized glycan with total area underneath all signals (peaks) of fluorescently derivatized glycans. In case of mass spectrometry, abundance of individual glycoforms is determined by normalization of the sum of the intensity of isotopic peaks of a certain glycoform with total intensity of all glycoforms.

Obtained values of IgG glycan structures are also normalized with regard to individual characteristics of the experiment for which it is known that they bring errors into the experiment, like for example: the plate on which the experiment has been carried out, instrument on which chromatographic analysis has been carried out, etc. For this purpose, a linear mixed model has been used, in which experimental variables are described as random effects.

By investigating correlations of individual glycan structures from samples taken from isolated populations of Vis island, Korčula island, and Orkney Isles, it has been established that individual glycans are significantly correlated to age. Especially high level of correlation of age and mass share of characteristic glycans in total mixture of IgG glycans has been established for the following glycans, called "glycans characteristic for age": F(6)A2 (GP4), F(6)A2B (GP6), F(6)A2[6]G1 (GP8), F(6)A2G2 (GP14), F(6)A2BG2 (GP15), and F(6)A2G2S1 (GP18) of the following chemical structures:

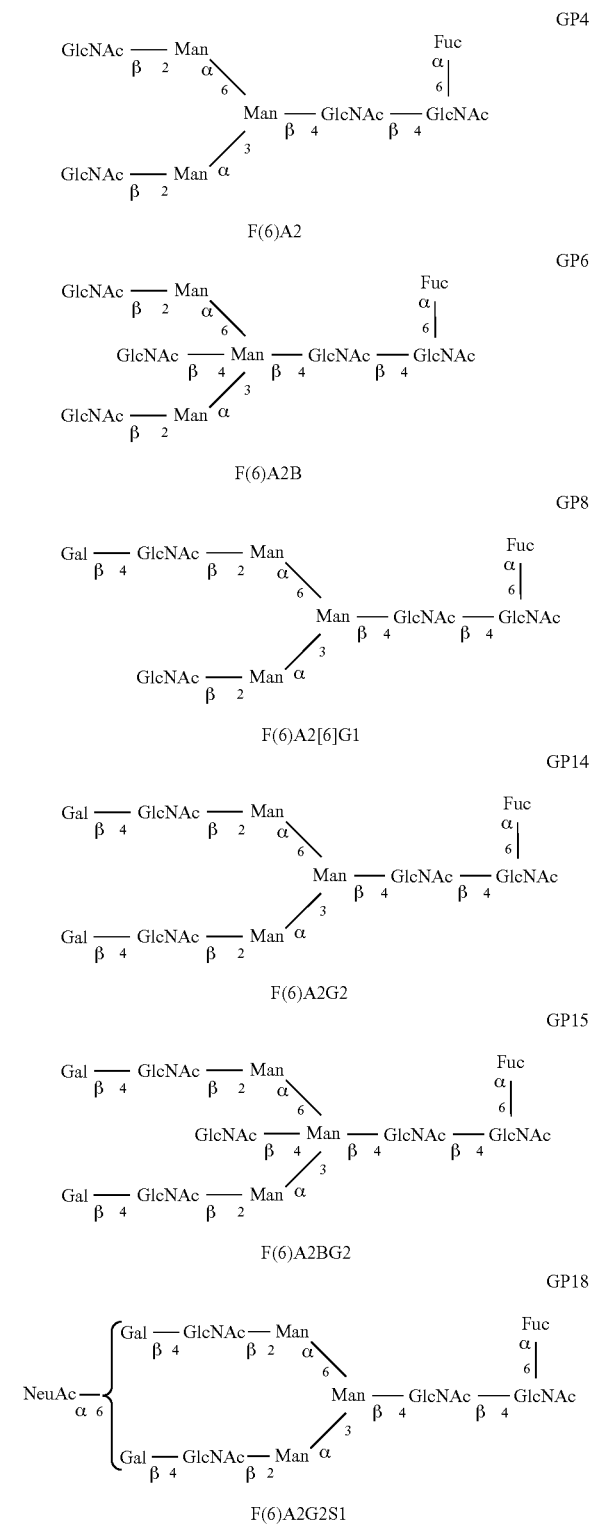

GlcNAc=N-acetylglucosamine
Fuc=fucose
Man=mannose
NeuAc=N-acetylneuraminic acid
Gal=galactose Changes in the abundance of all six characteristic glycans with (chronological) age obtained on the basis of UPLC analysis, for both women and men, are shown on FIGS. 2-7. Correlation of the abundance of characteristic glycans with sex and age of the respondents from Vis island is shown in FIGS. 2A-7A, from Korčula island in FIGS. 2B-7B, and from Orkney Isles in FIGS. 2C-7C.

Figure 8:
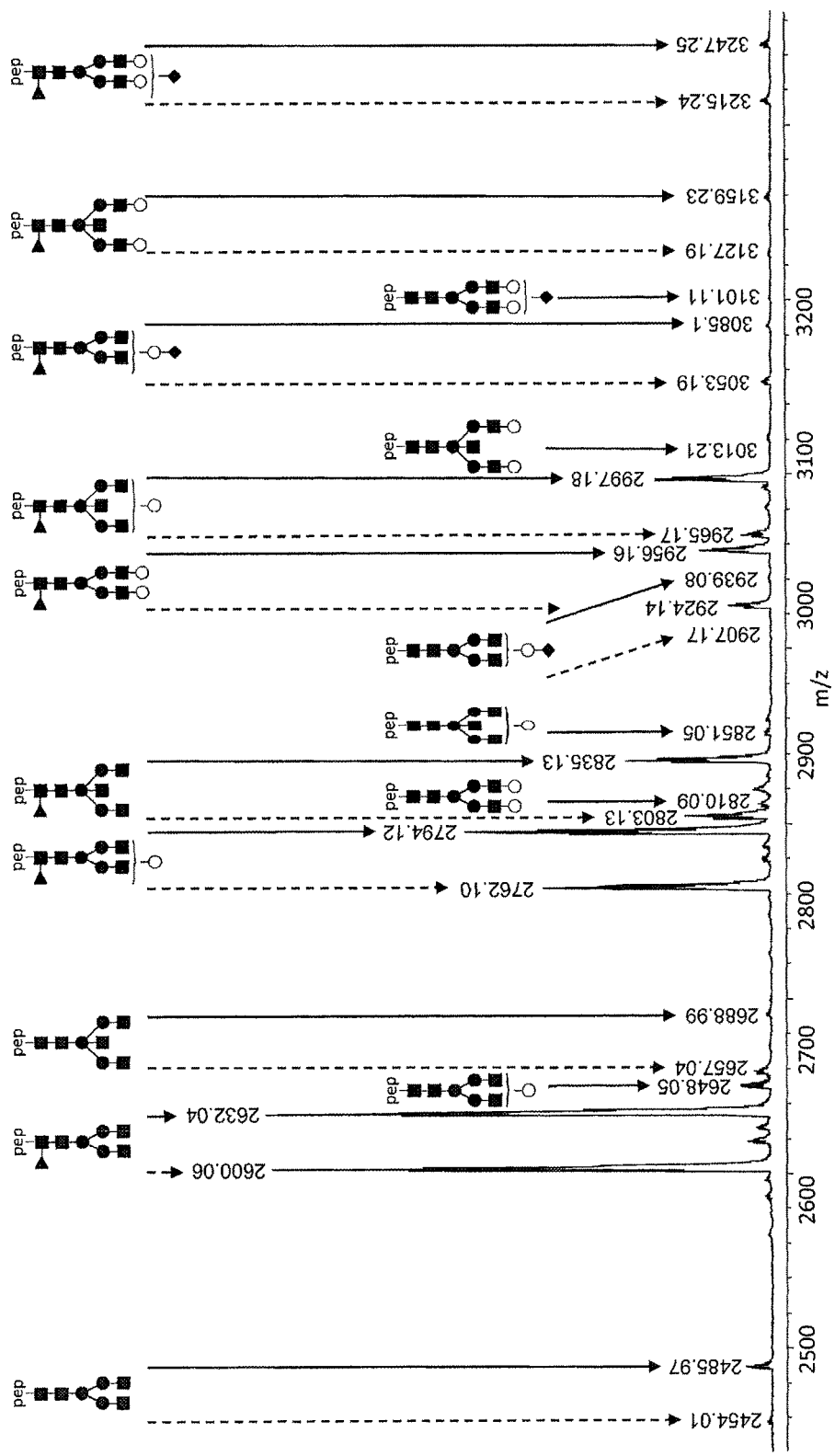
FIG. 8. Typical mass spectra obtained by the quantitative analysis of IgG N-glycopeptides (N-glycoforms) by MALDI-TOF mass spectrometry.
Figure 9A:
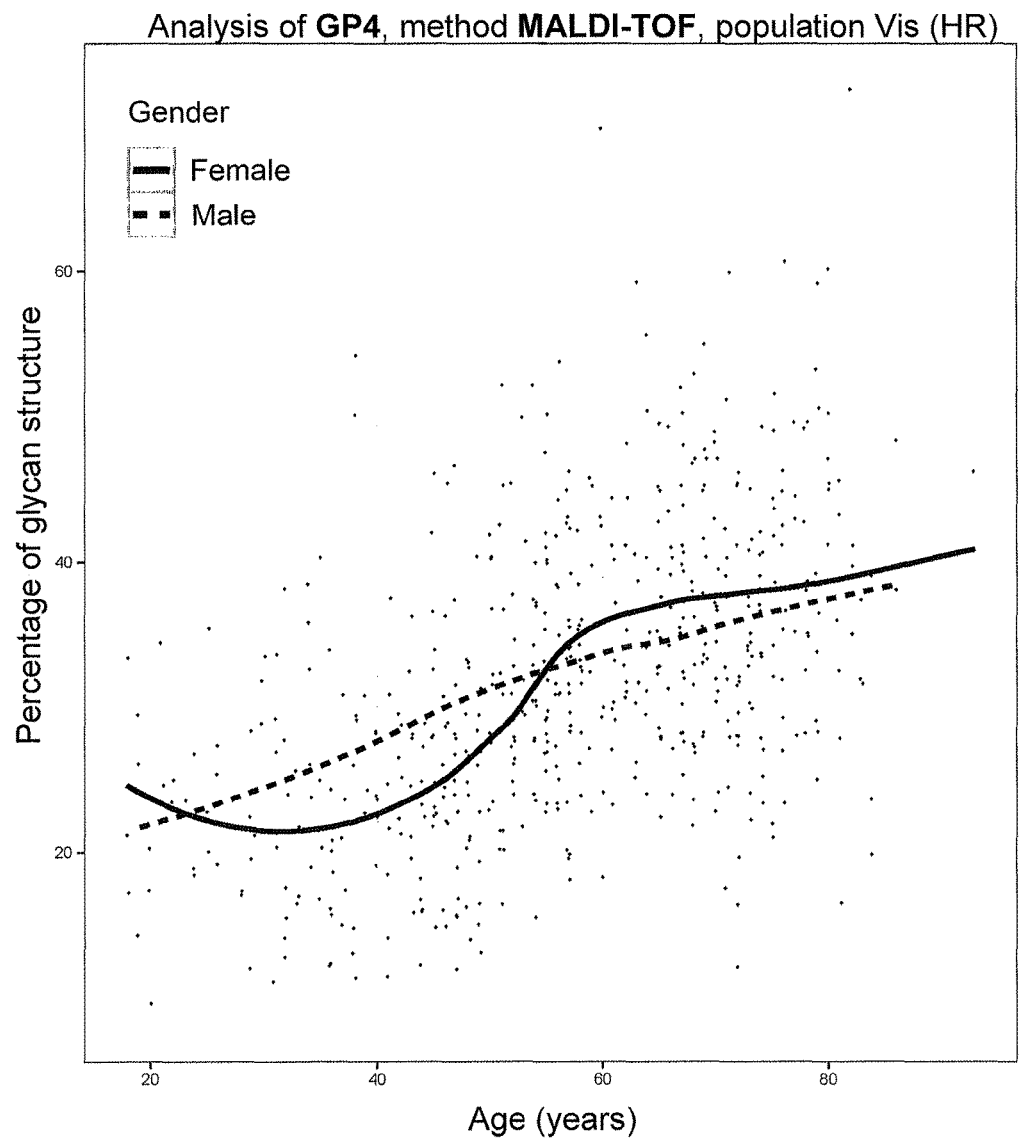
FIG. 9A. Change in the abundance of glycoform F(6)A2 (GP4) with age among women (continuous line) and men (dashed line) in the population of Vis island (HR), determined by MALDI-TOF mass spectrometry.
Figure 9B:
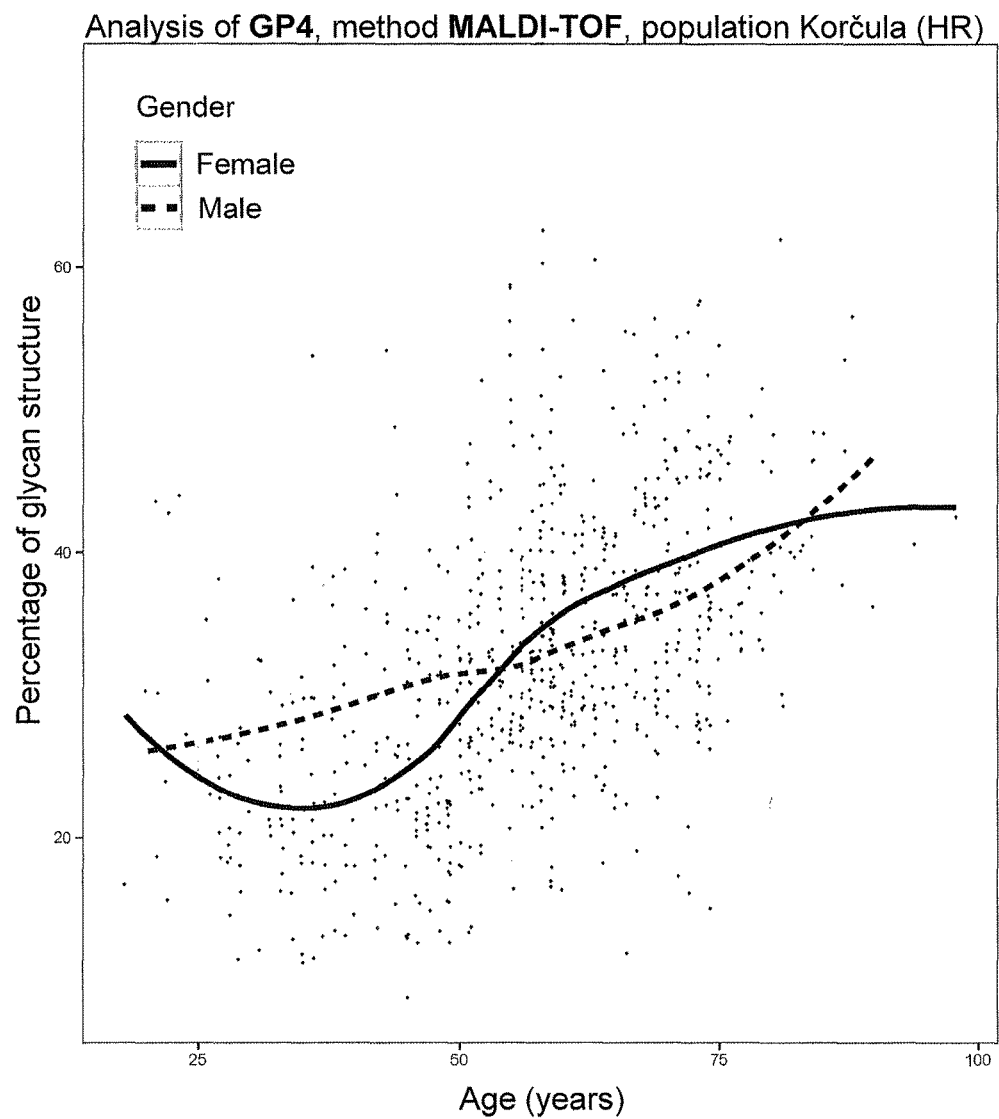
FIG. 9B. Change in the abundance of glycoform F(6)A2 (GP4) with age among women (continuous line) and men (dashed line) in the population of Korčula island (HR), determined by MALDI-TOF mass spectrometry.
Figure 10A:
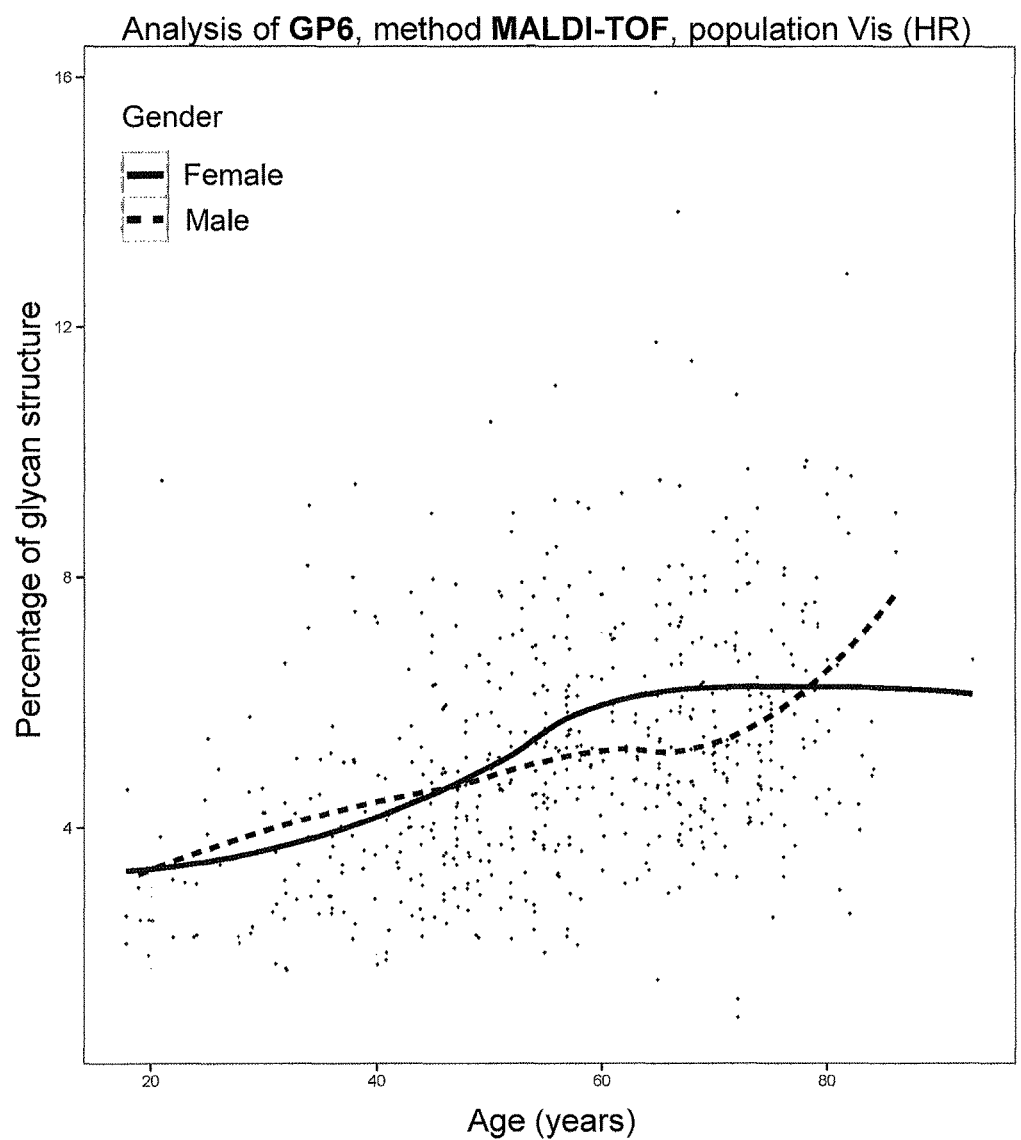
FIG. 10A. Change in the abundance of glycoform F(6)A2B (GP6) with age among women (continuous line) and men (dashed line) in the population of Vis island (HR), determined by MALDI-TOF mass spectrometry.
Figure 10B:
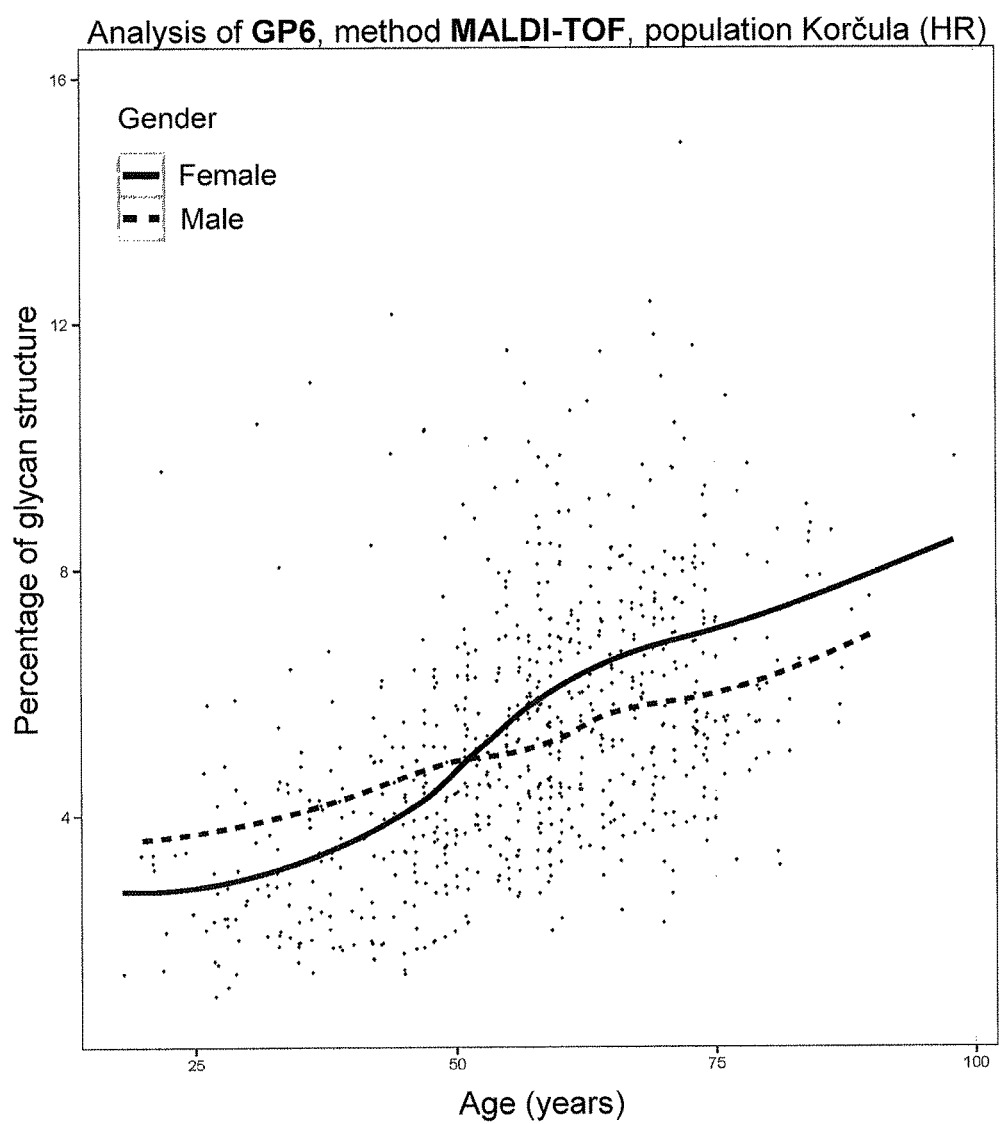
FIG. 10B. Change in the abundance of glycoform F(6)A2B (GP6) with age among women (continuous line) and men (dashed line) in the population of Korčula island (HR), determined by MALDI-TOF mass spectrometry.
Figure 11A:
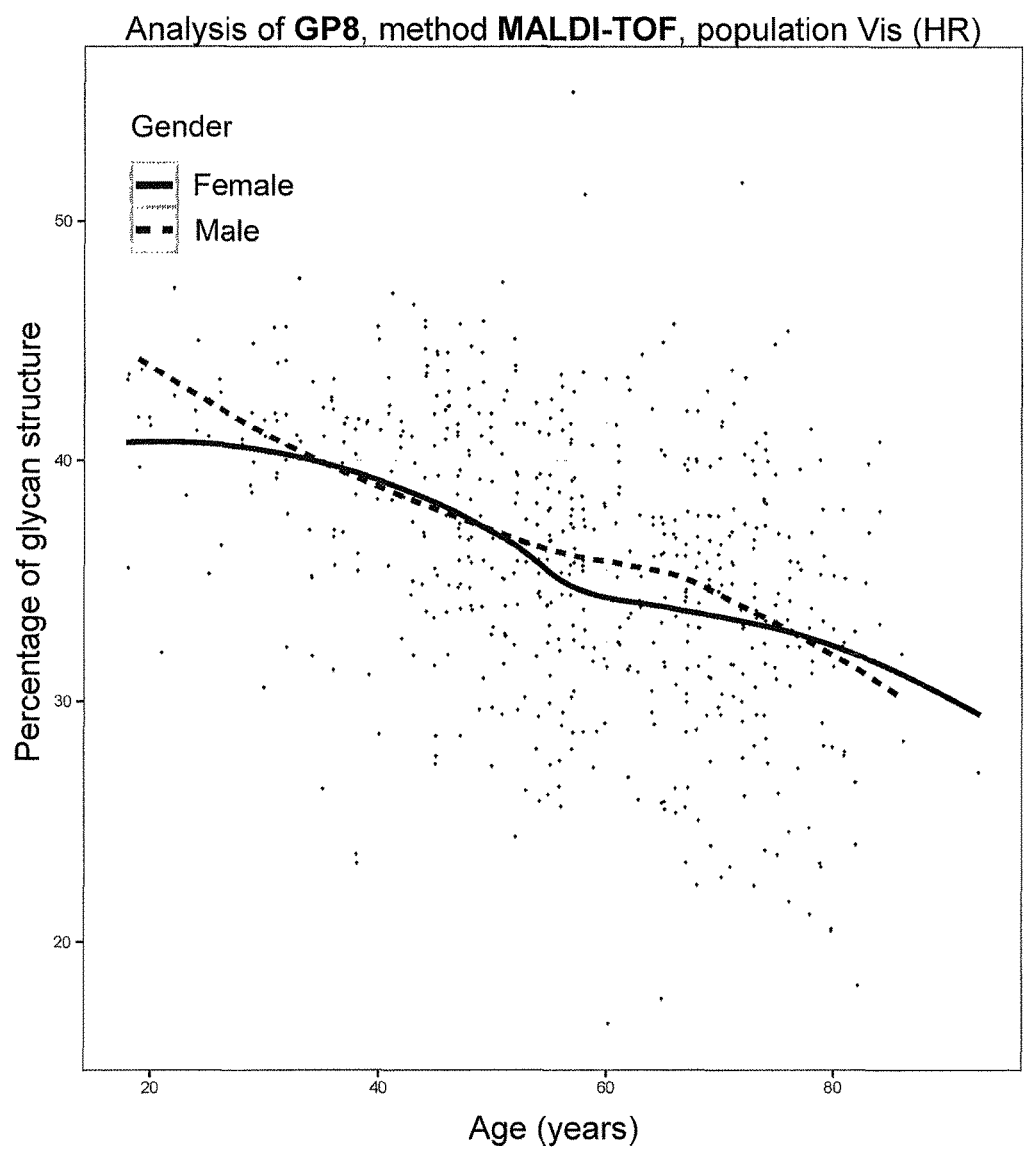
FIG. 11A. Change in the abundance of glycoform F(6)A2[6]G1 (GP8) with age among women (continuous line) and men (dashed line) in the population of Vis island (HR), determined by MALDI-TOF mass spectrometry.
Figure 11B:
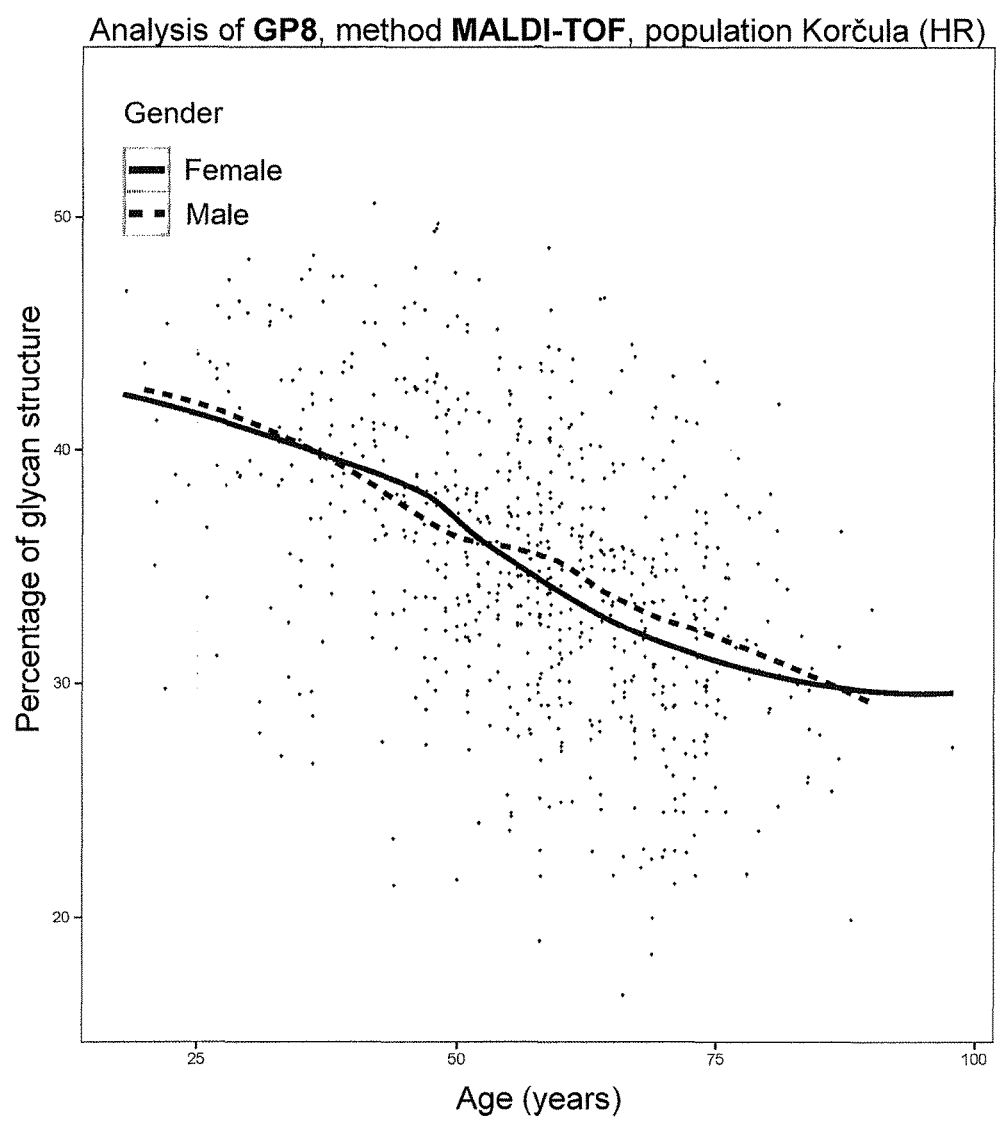
FIG. 11B. Change in the abundance of glycoform F(6)A2[6]G1 (GP8) with age among women (continuous line) and men (dashed line) in the population of Korčula island (HR), determined by MALDI-TOF mass spectrometry.
Figure 12A:
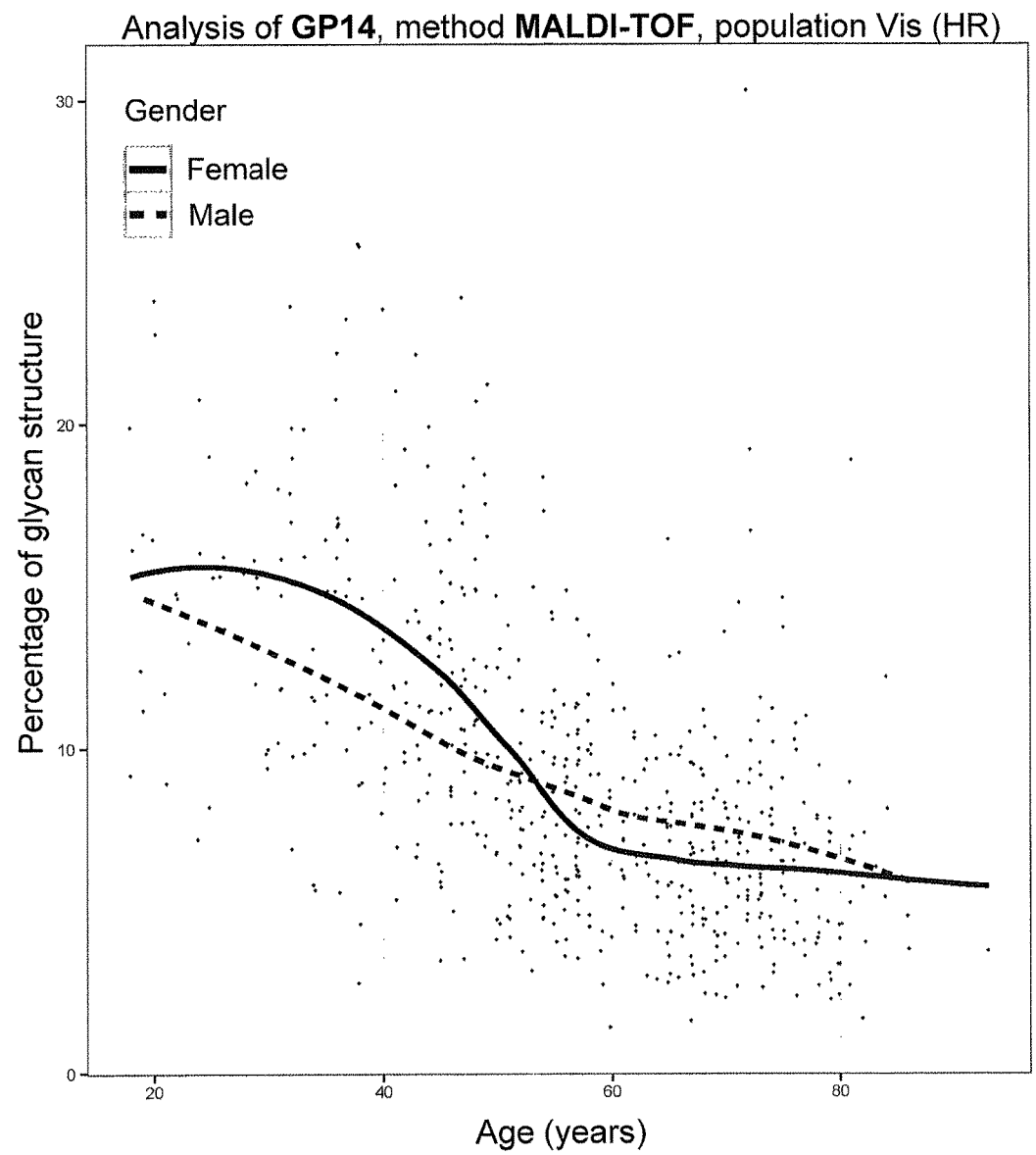
FIG. 12A. Change in the abundance of glycoform F(6)A2G2 (GP14) with age among women (continuous line) and men (dashed line) in the population of Vis island (HR), determined by MALDI-TOF mass spectrometry.
Figure 12B:
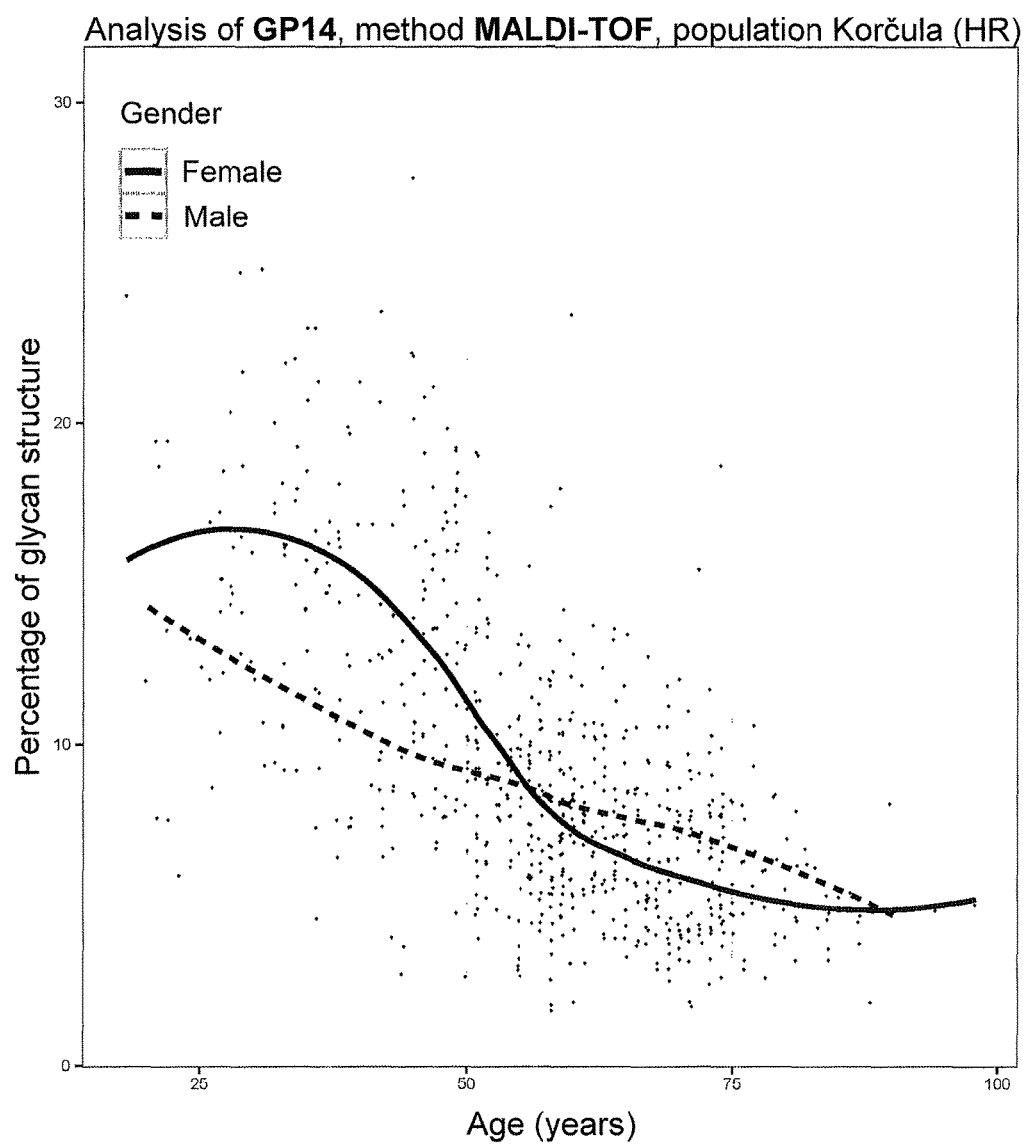
FIG. 12B. Change in the abundance of glycoform F(6)A2G2 (GP14) with age among women (continuous line) and men (dashed line) in the population of Korčula island (HR), determined by MALDI-TOF mass spectrometry.
Figure 13A:
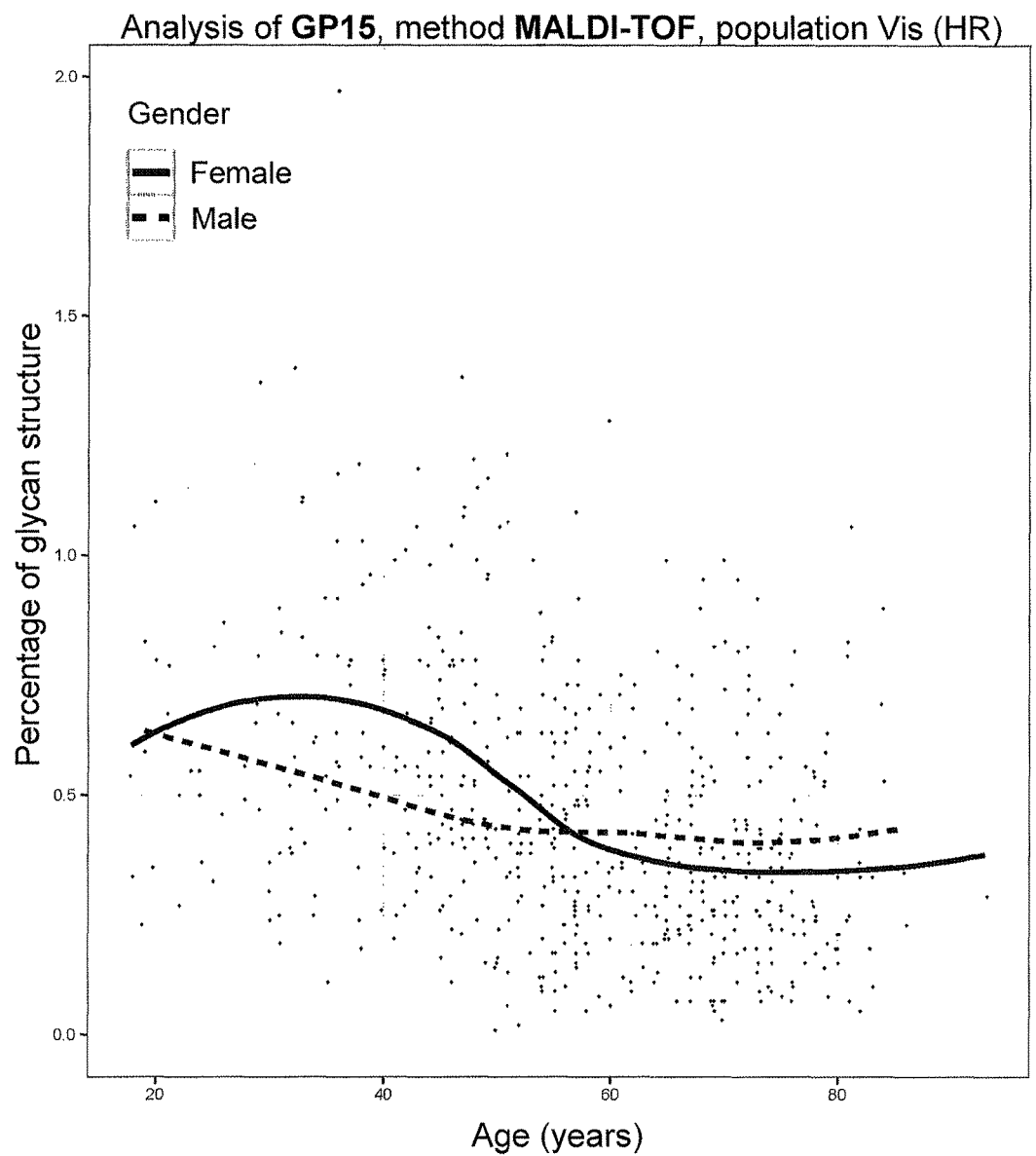
FIG. 13A. Change in the abundance of glycoform F(6)A2BG2 (GP15) with age among women (continuous line) and men (dashed line) in the population of Vis island (HR), determined by MALDI-TOF mass spectrometry.
Figure 13B:
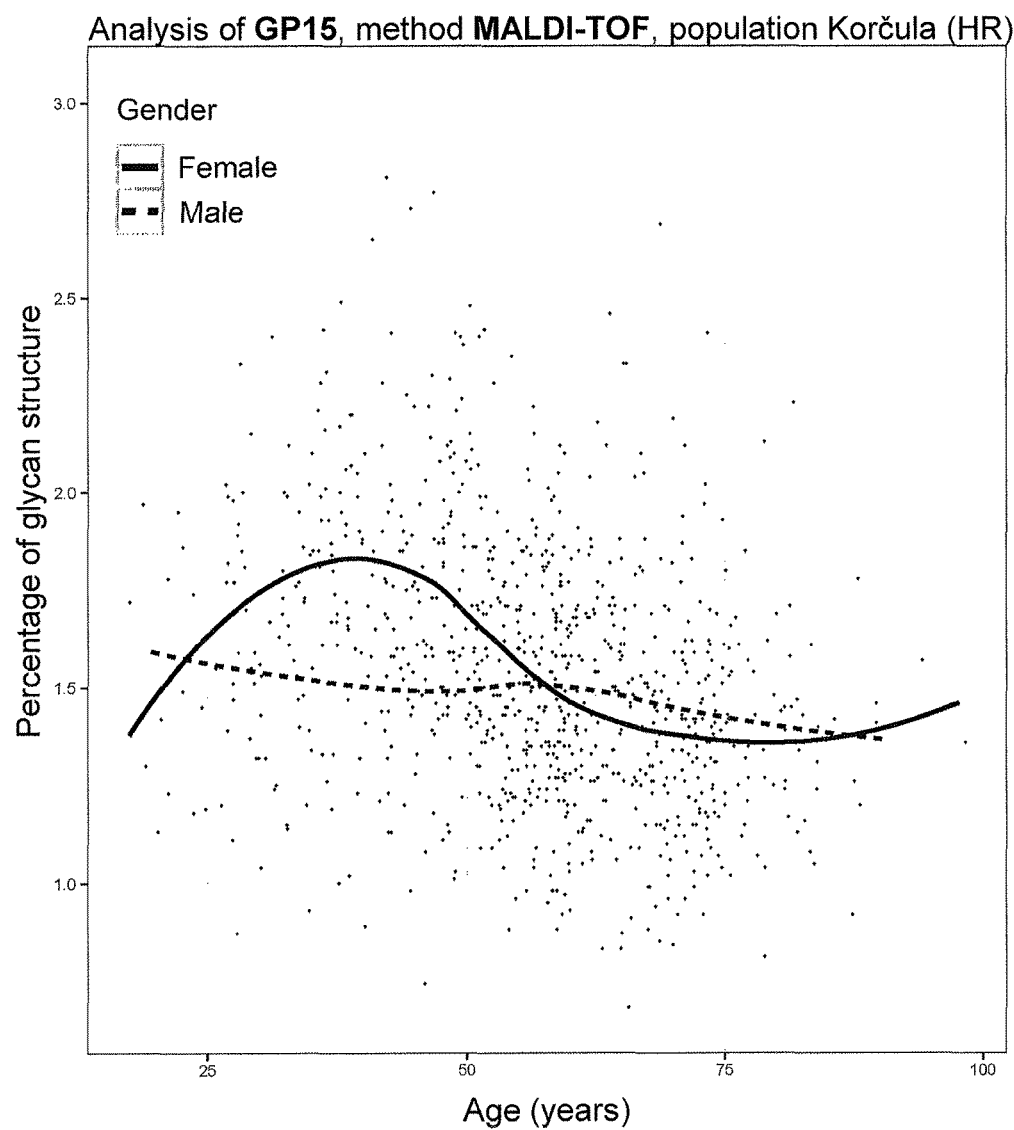
FIG. 13B. Change in the abundance of glycoform F(6)A2BG2 (GP15) with age among women (continuous line) and men (dashed line) in the population of Korčula island (HR), determined by MALDI-TOF mass spectrometry.
Figure 14A:
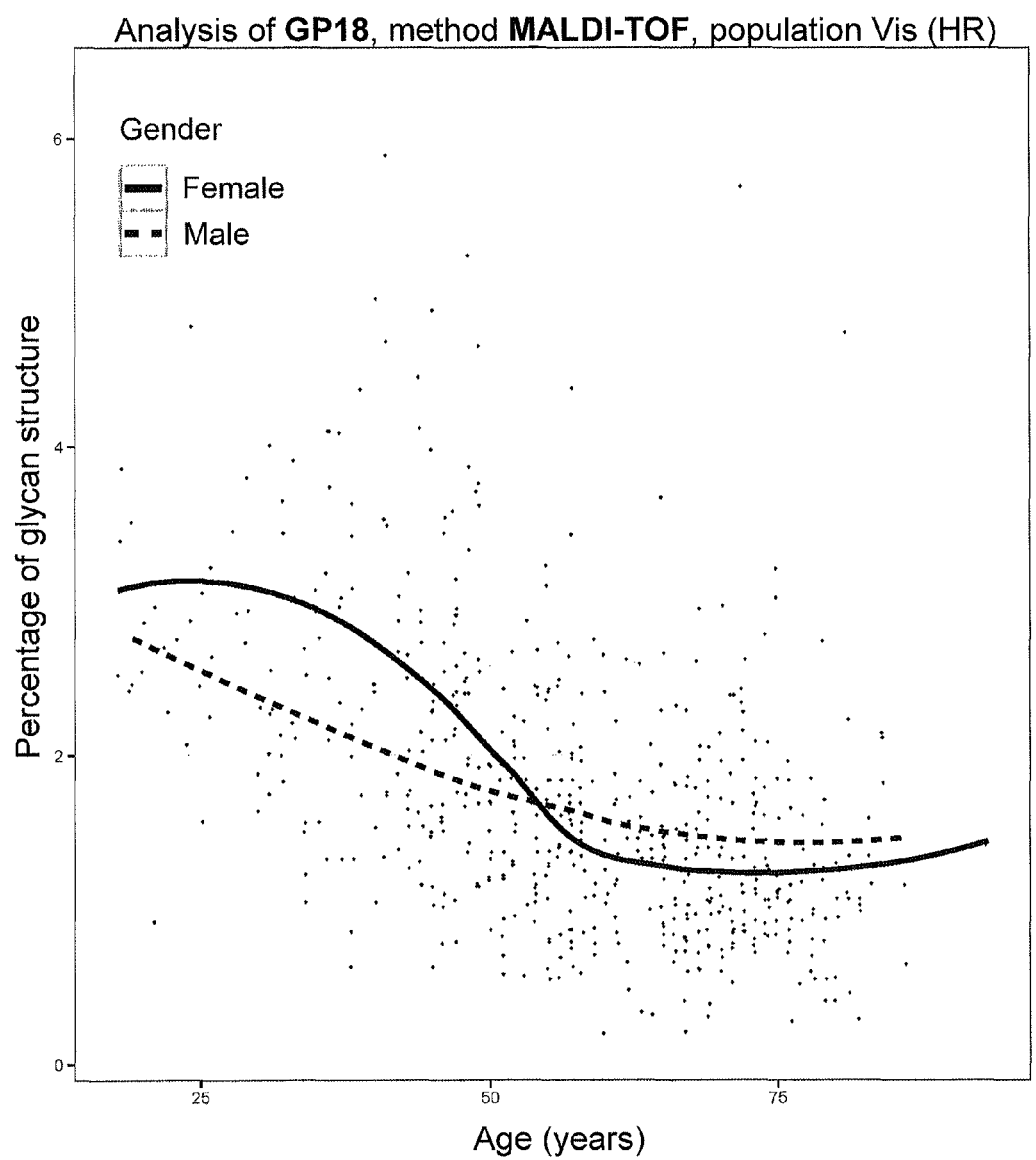
FIG. 14A. Change in the abundance of glycoform F(6)A2G2S1 (GP18) with age among women (continuous line) and men (dashed line) in the population of Vis island (HR), determined by MALDI-TOF mass spectrometry.
Figure 14B:
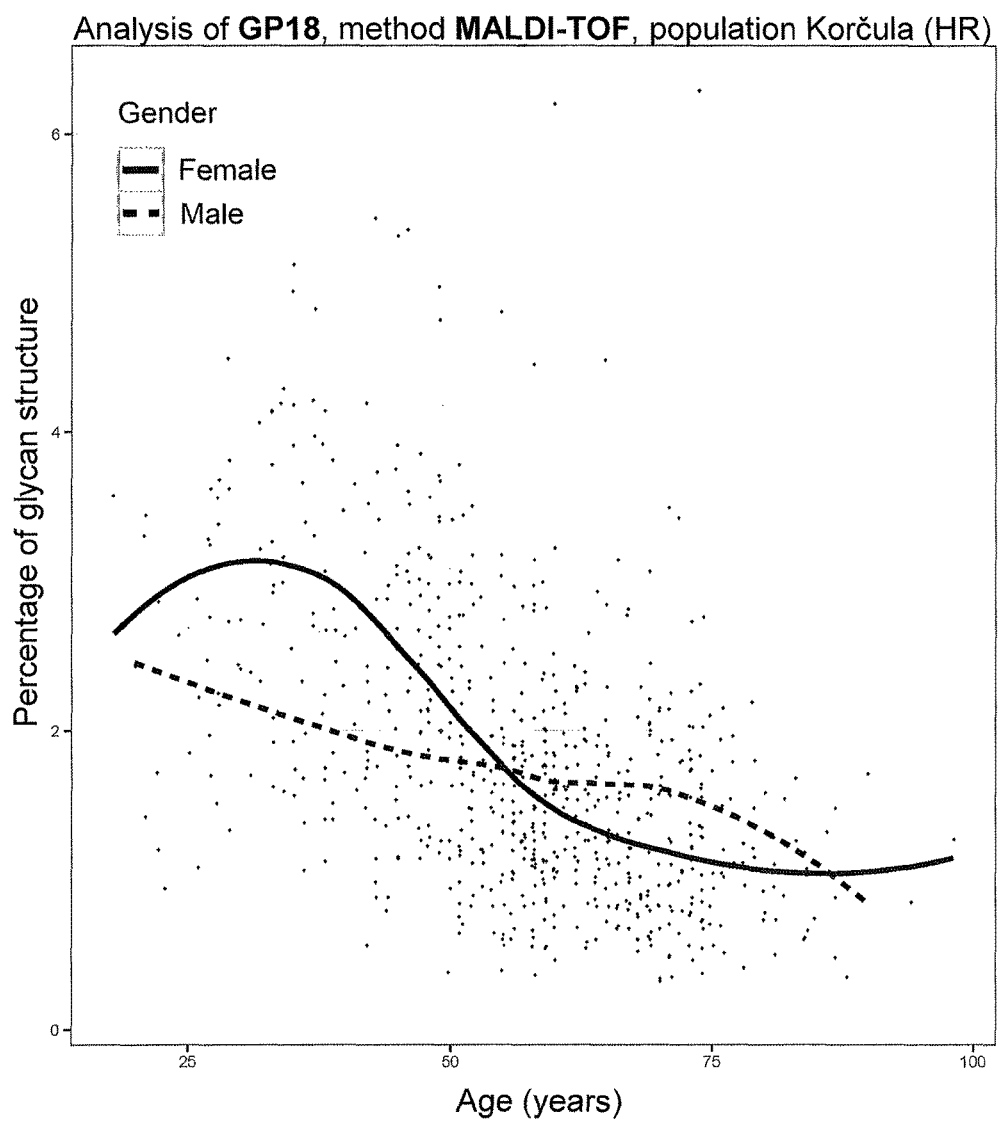
FIG. 14B. Change in the abundance of glycoform F(6)A2G2S1 (GP18) with age among women (continuous line) and men (dashed line) in the population of Korčula island (HR), determined by MALDI-TOF mass spectrometry.

In analogue manner, samples of immunoglobulin G (IgG) have been analysed by MALDI-TOF mass spectrometry as well, and during this process all glycopeptides, or glycoforms, that correspond to IgG glycans characteristic for age were separated. A typical MS-spectrum is shown in FIG. 8 and it presents signals (isotopic peaks) of corresponding glycoforms, in other words their molecular ions, described via mass-to-charge ratio (m/z). Above each signal, there is a corresponding glycan structure and here, peptide remnant is schematically marked by abbreviation "pep".

Correlation of the abundance of characteristic glycoforms with sex and age of the respondents, obtained by alternative analytical technique MALDI-TOF from the population of Vis island is shown in FIGS. 9A-14A, and from Korčula island in FIGS. 9B-14B.

Figure 15:
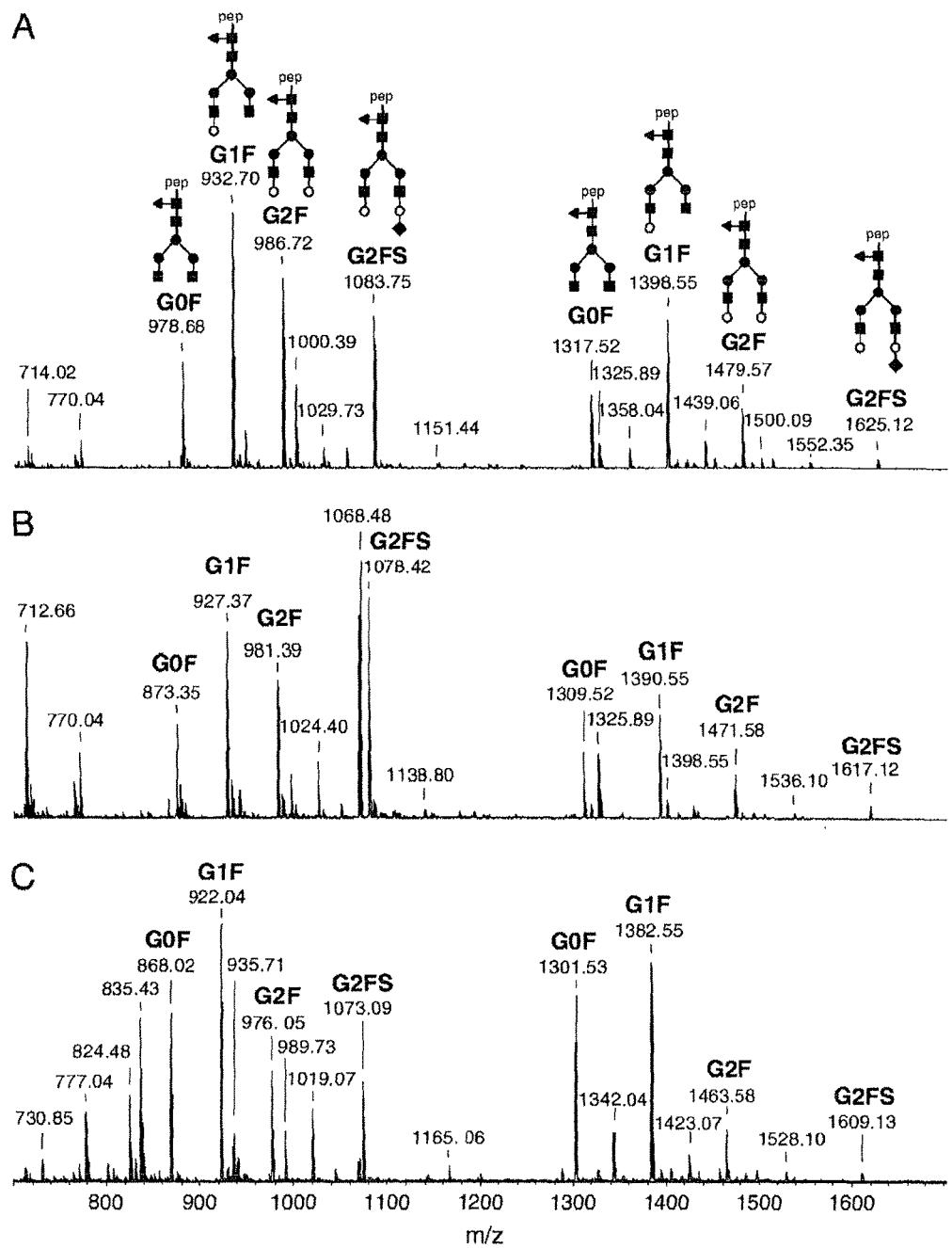
FIG. 15. Typical chromatogram obtained by the quantitative analysis of IgG N-glycoforms by liquid chromatography-mass spectrometry (LC-MS).
Figure 16A:
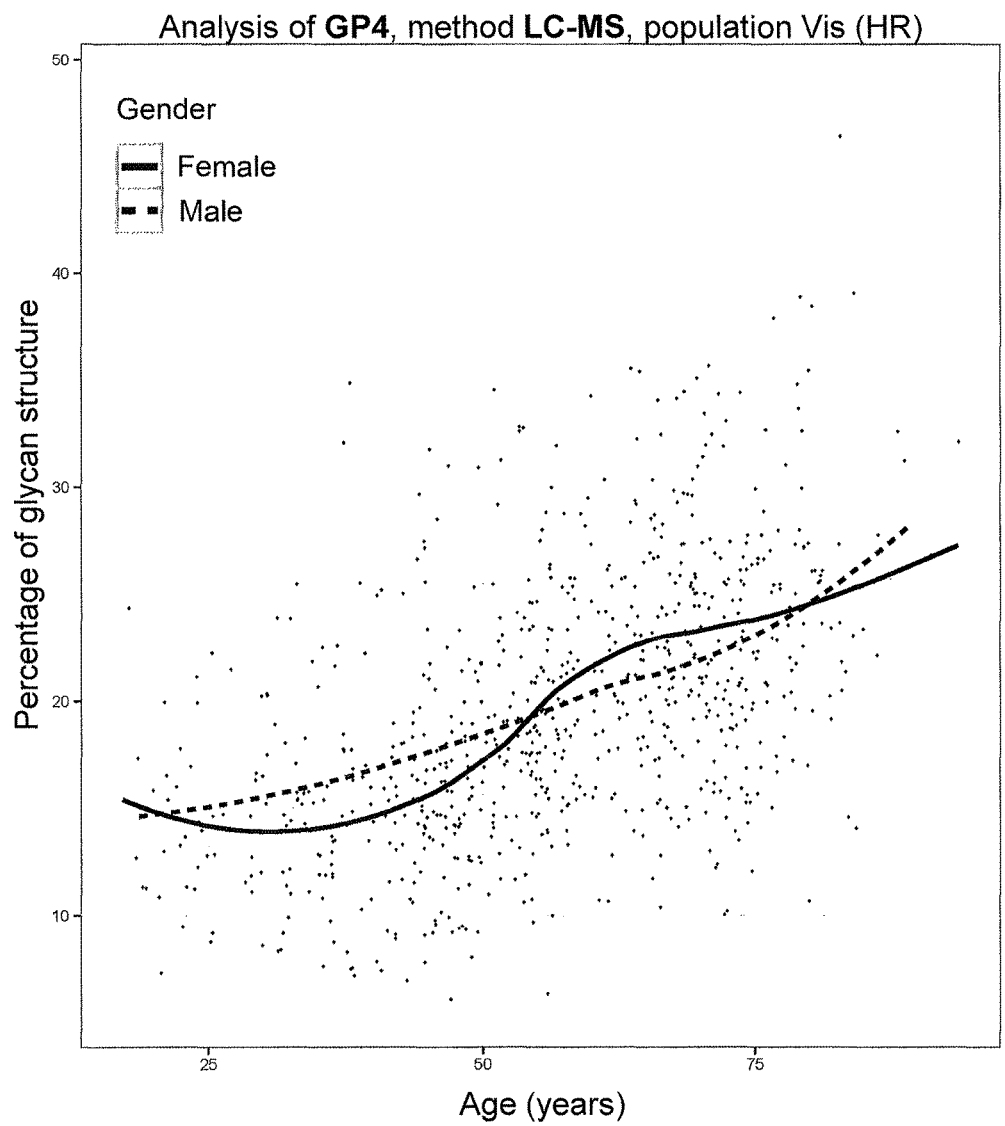
FIG. 16A. Change in the abundance of glycoform F(6)A2 (GP4) with age among women (continuous line) and men (dashed line) in the population of Vis island (HR), determined by liquid chromatography-mass spectrometry (LC-MS).
Figure 16B:
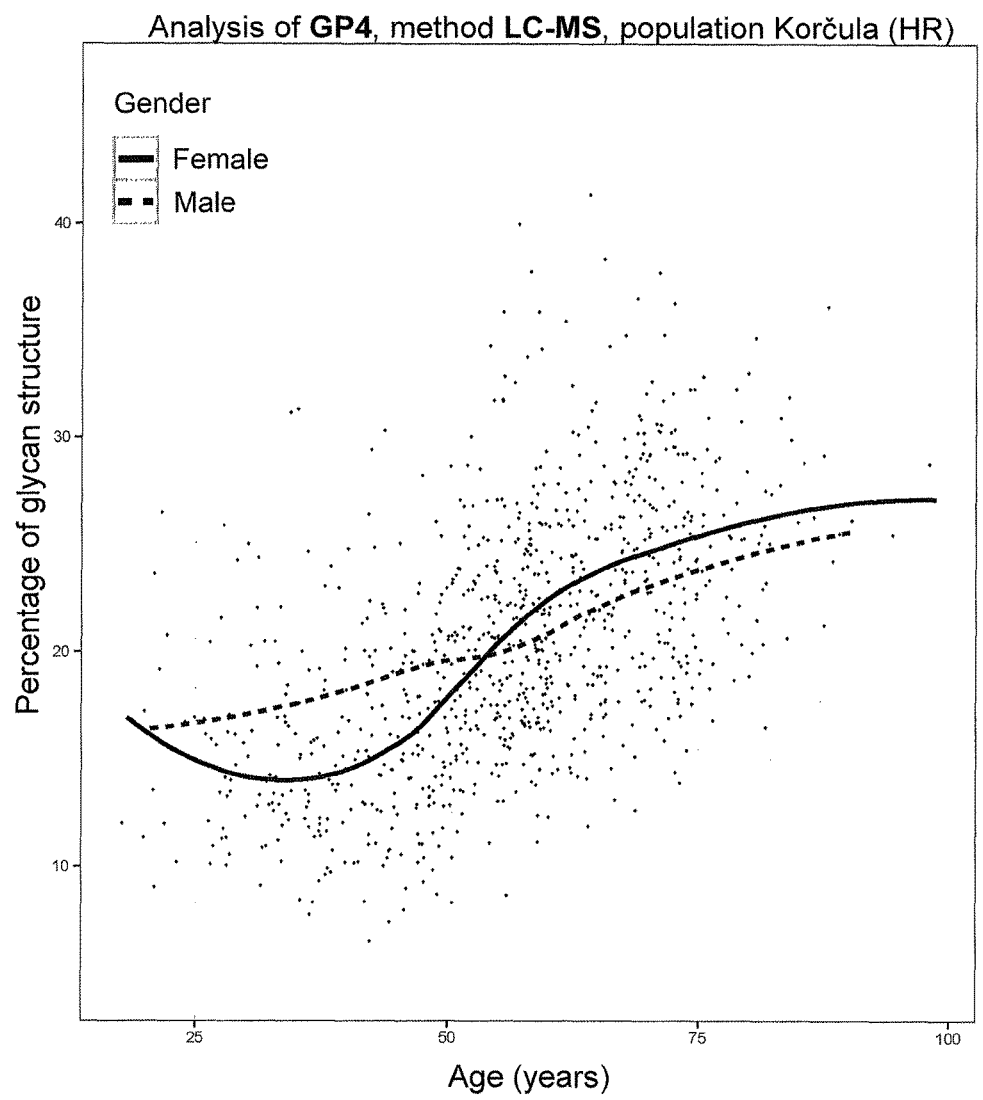
FIG. 16B. Change in the abundance of glycoform F(6)A2 (GP4) with age among women (continuous line) and men (dashed line) in the population of Korčula island (HR), determined by liquid chromatography-mass spectrometry (LC-MS).
Figure 17A:
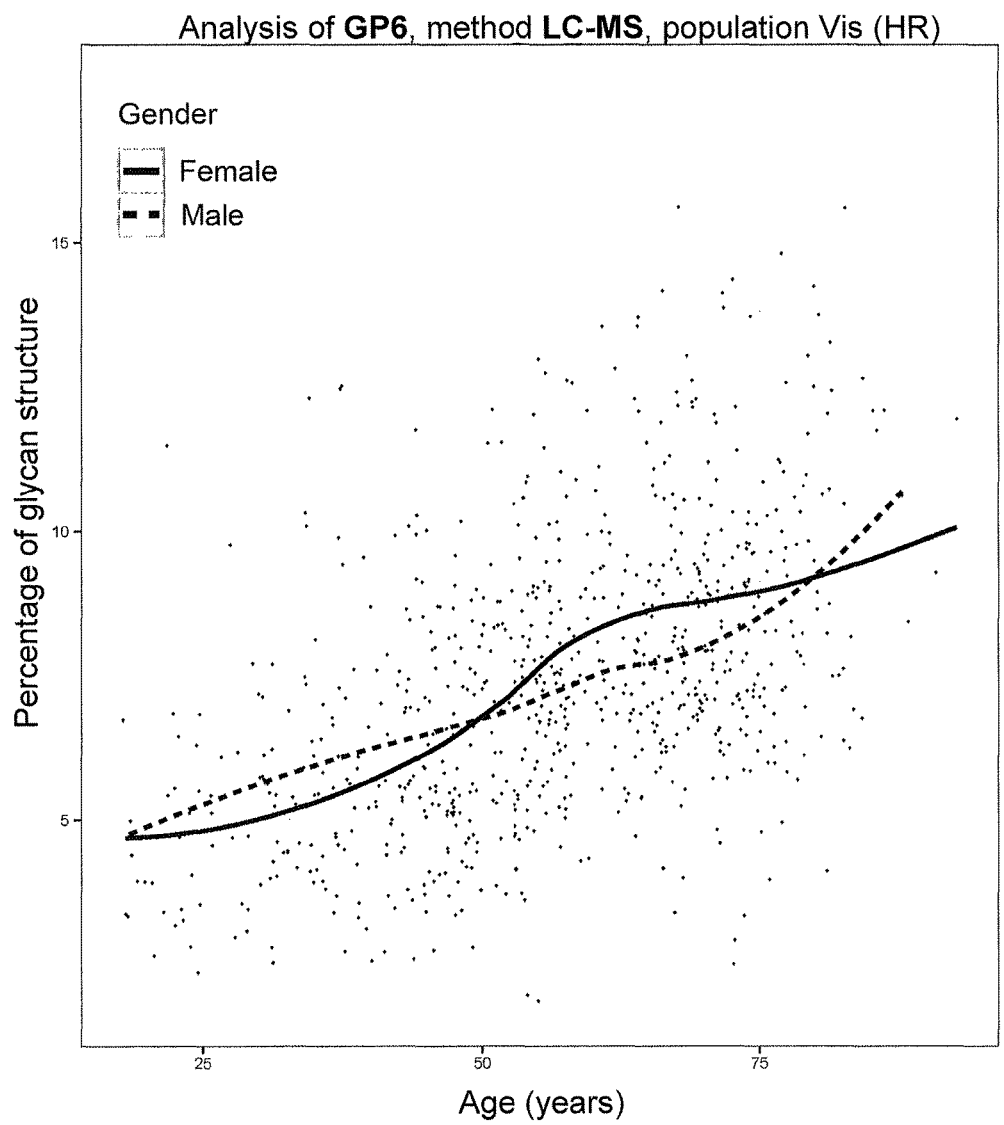
FIG. 17A. Change in the abundance of glycoform F(6)A2B (GP6) with age among women (continuous line) and men (dashed line) in the population of Vis island (HR), determined by liquid chromatography-mass spectrometry (LC-MS).
Figure 17B:
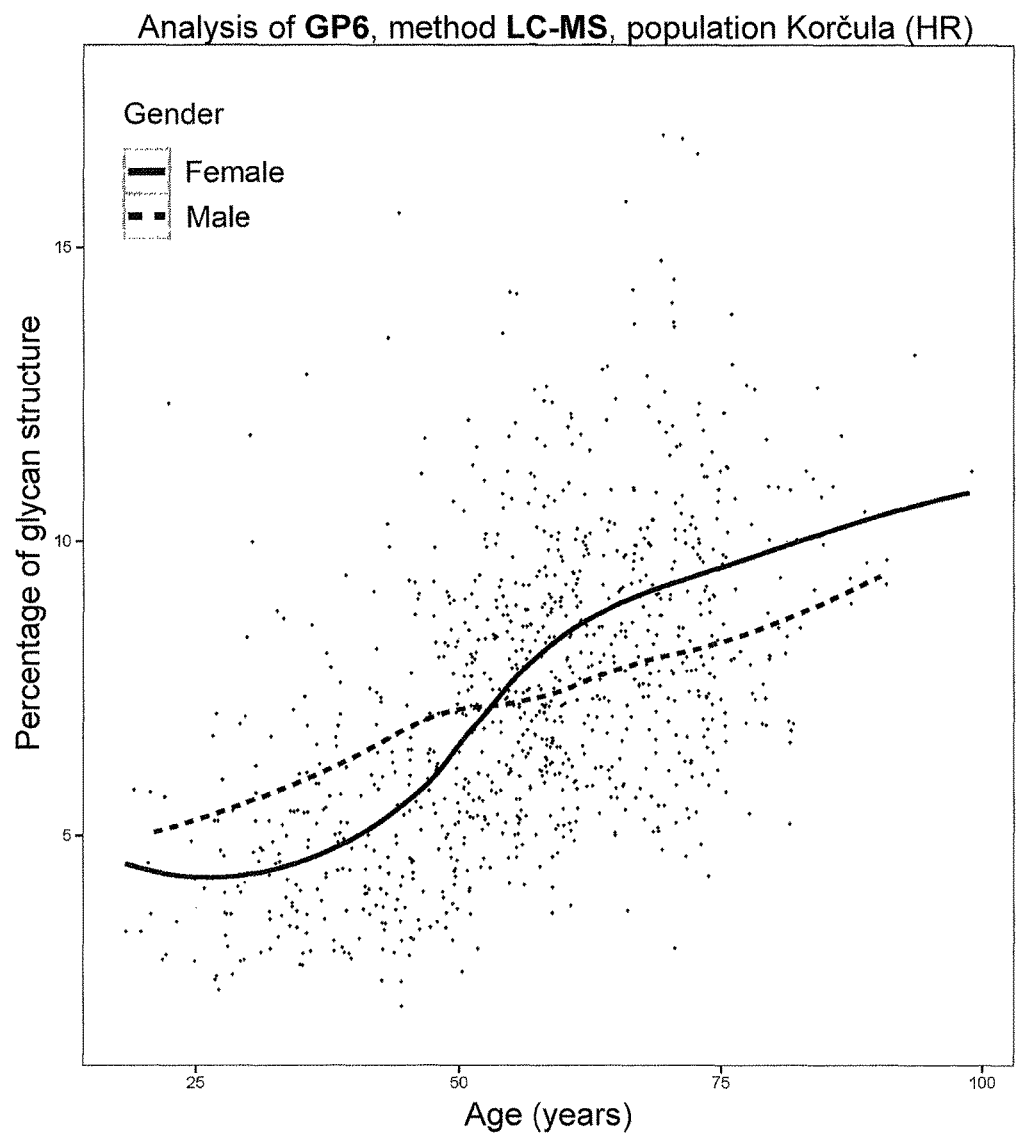
FIG. 17B. Change in the abundance of glycoform F(6)A2B (GP6) with age among women (continuous line) and men (dashed line) in the population of Korčula island (HR), determined by liquid chromatography-mass spectrometry (LC-MS).
Figure 18A:
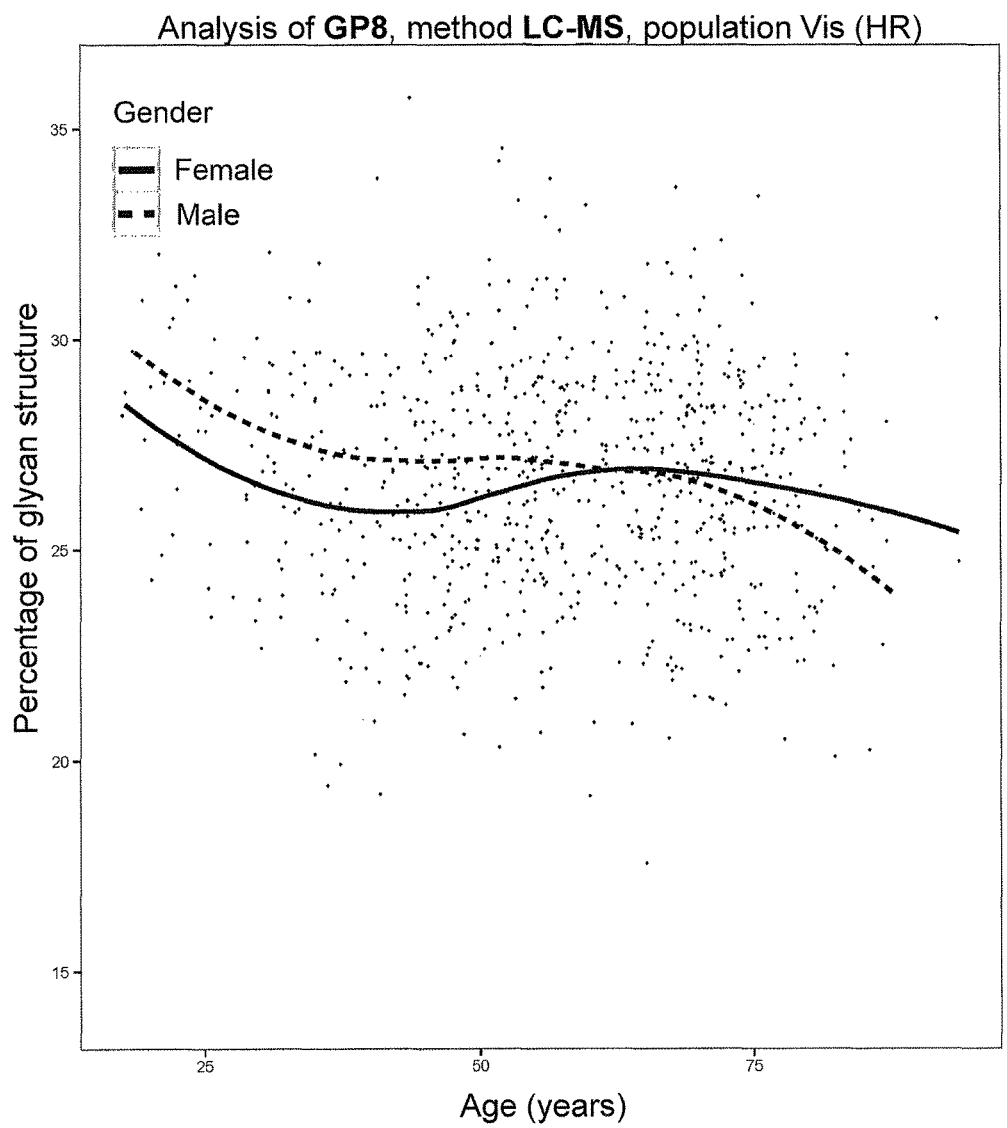
FIG. 18A. Change in the abundance of glycoform F(6)A2[6]G1 (GP8) with age among women (continuous line) and men (dashed line) in the population of Vis island (HR), determined by liquid chromatography-mass spectrometry (LC-MS).
Figure 18B:
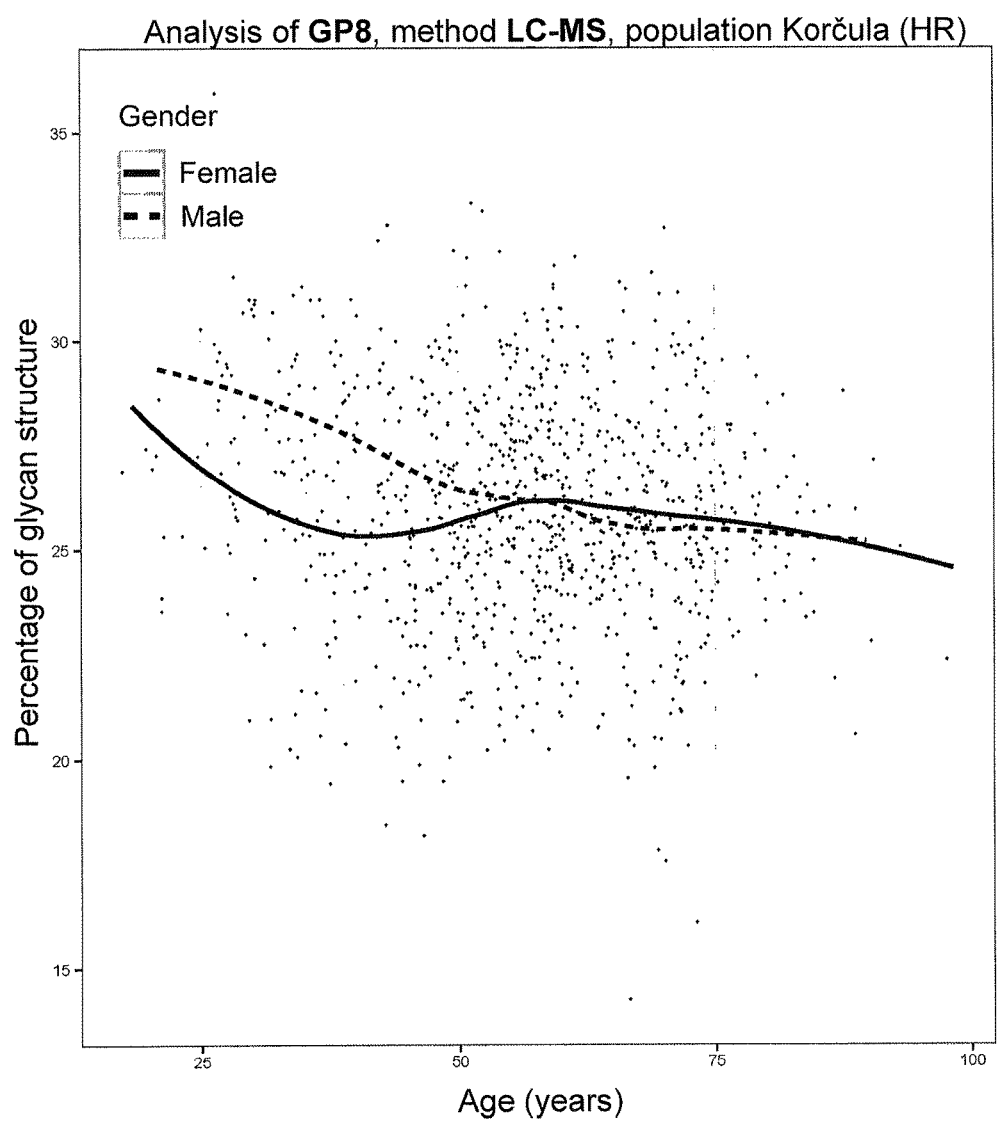
FIG. 18B. Change in the abundance of glycoform F(6)A2[6]G1 (GP8) with age among women (continuous line) and men (dashed line) in the population of Korčula island (HR), determined by liquid chromatography-mass spectrometry (LC-MS).
Figure 19A:
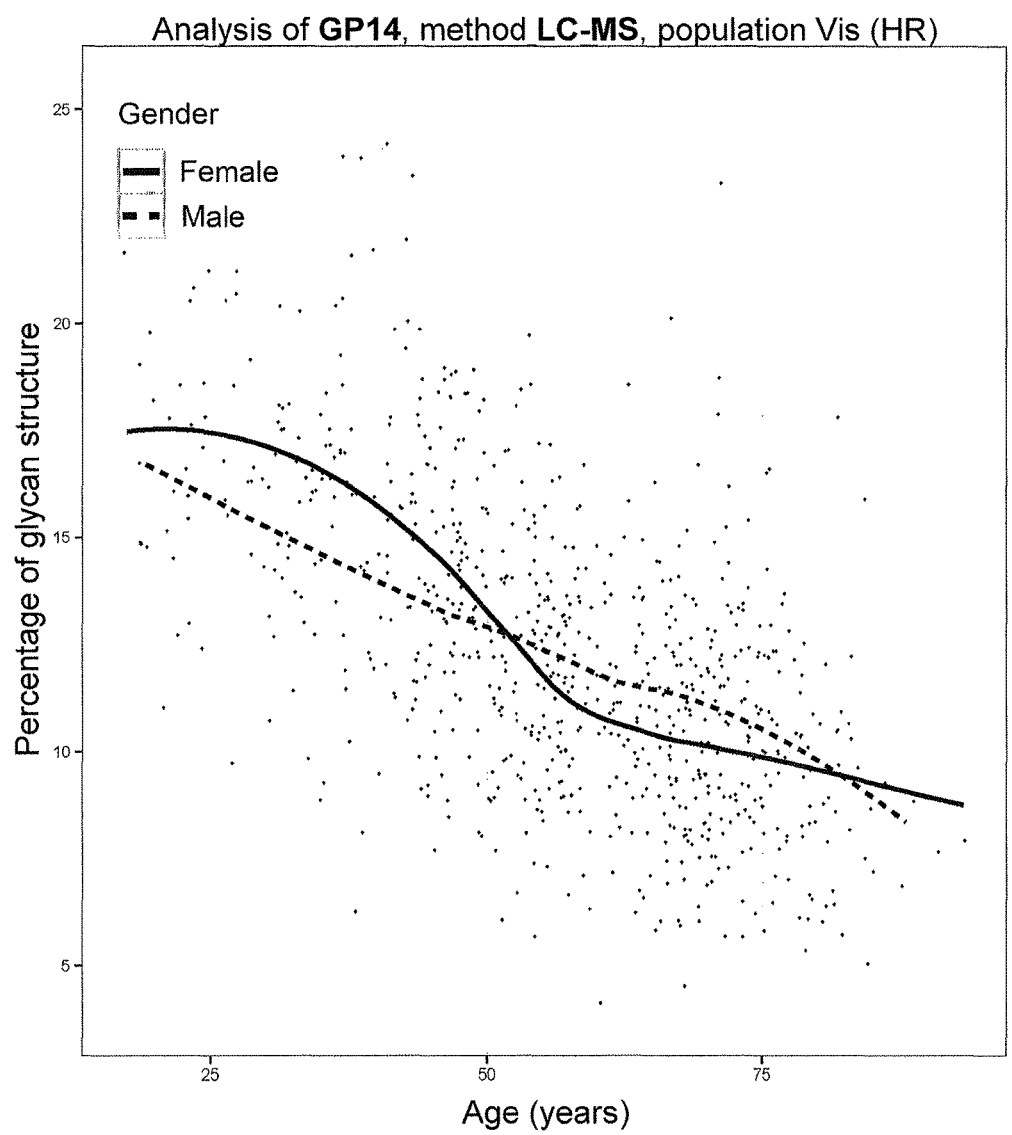
FIG. 19A. Change in the abundance of glycoform F(6)A2G2 (GP14) with age among women (continuous line) and men (dashed line) in the population of Vis island (HR), determined by liquid chromatography-mass spectrometry (LC-MS).
Figure 19B:
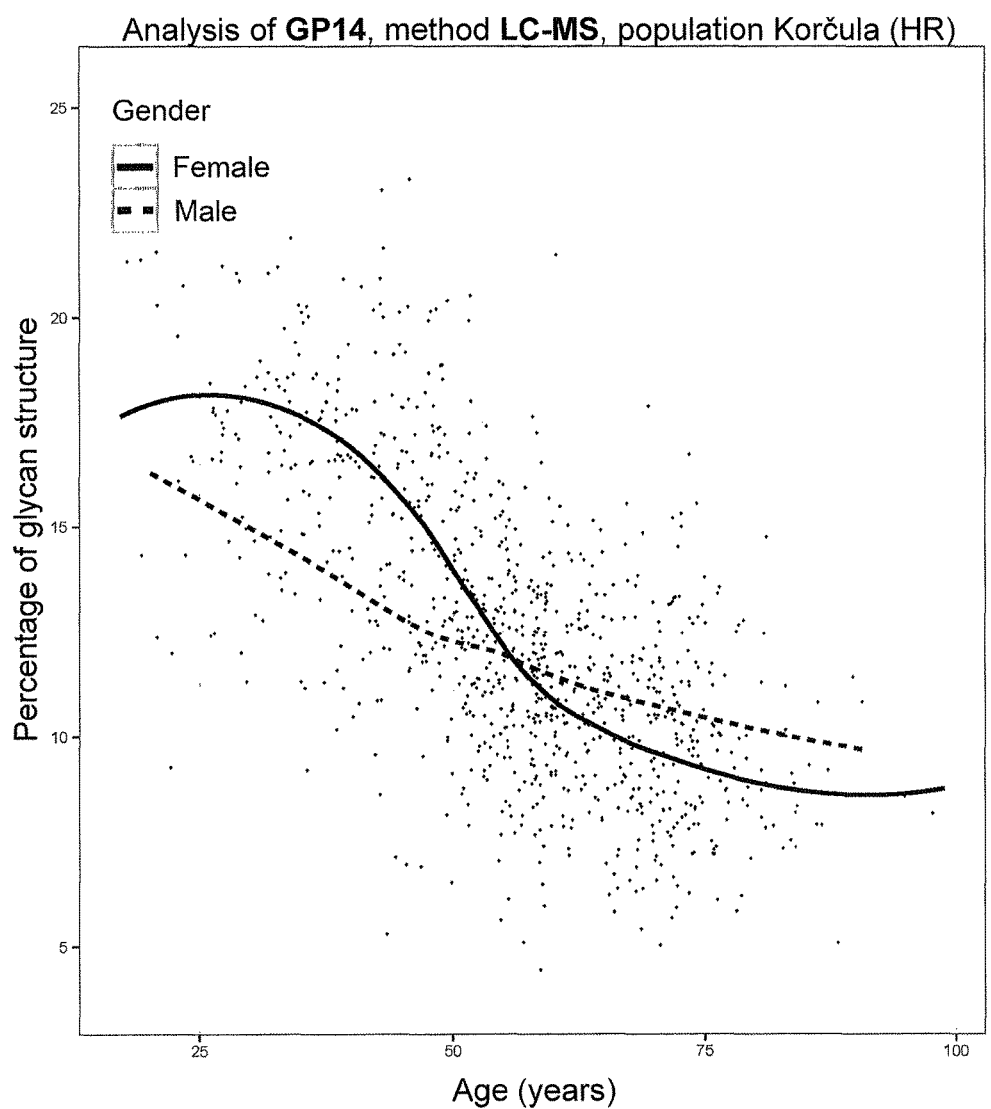
FIG. 19B. Change in the abundance of glycoform F(6)A2G2 (GP14) with age among women (continuous line) and men (dashed line) in the population of Korčula island (HR), determined by liquid chromatography-mass spectrometry (LC-MS).
Figure 20A:
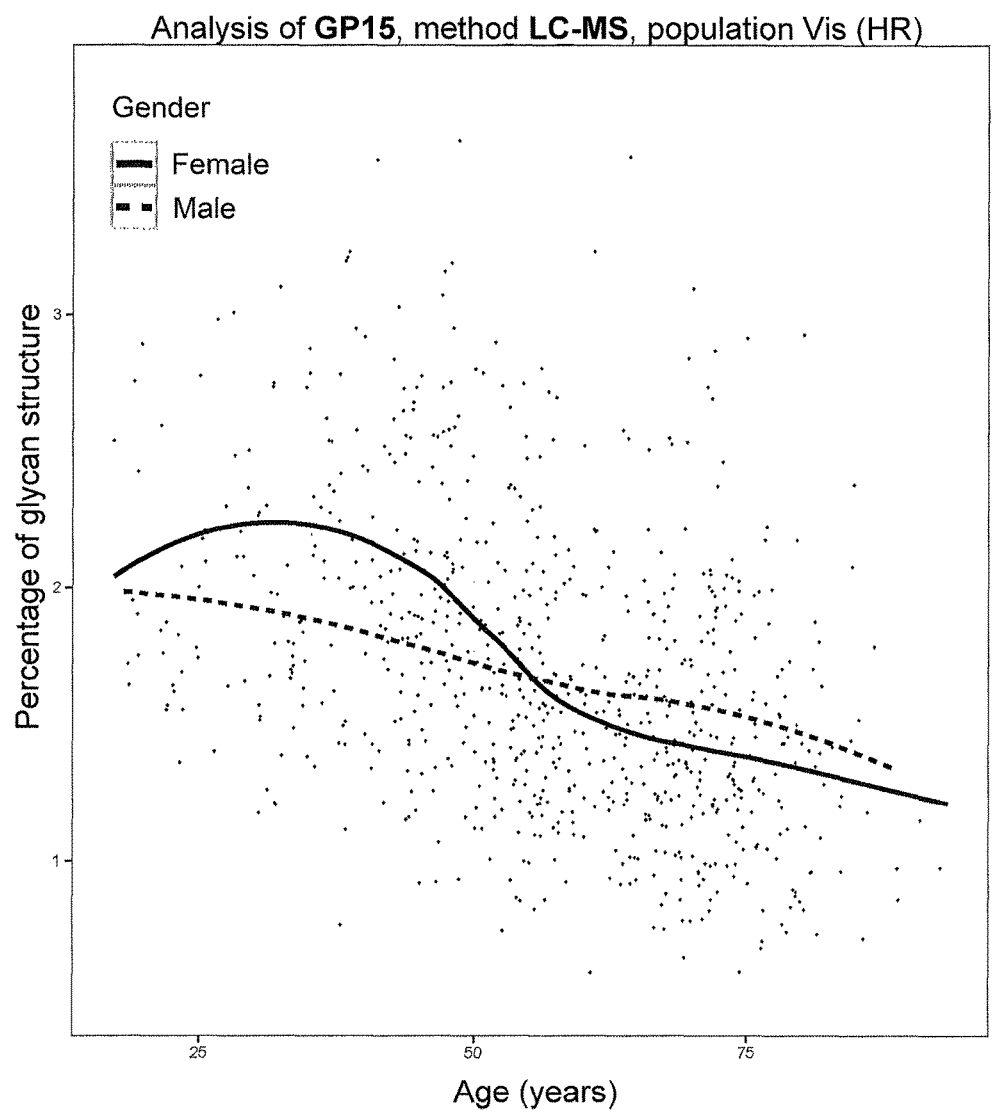
FIG. 20A. Change in the abundance of glycoform F(6)A2BG2 (GP15) with age among women (continuous line) and men (dashed line) in the population of Vis island (HR), determined by liquid chromatography-mass spectrometry (LC-MS).
Figure 20B:
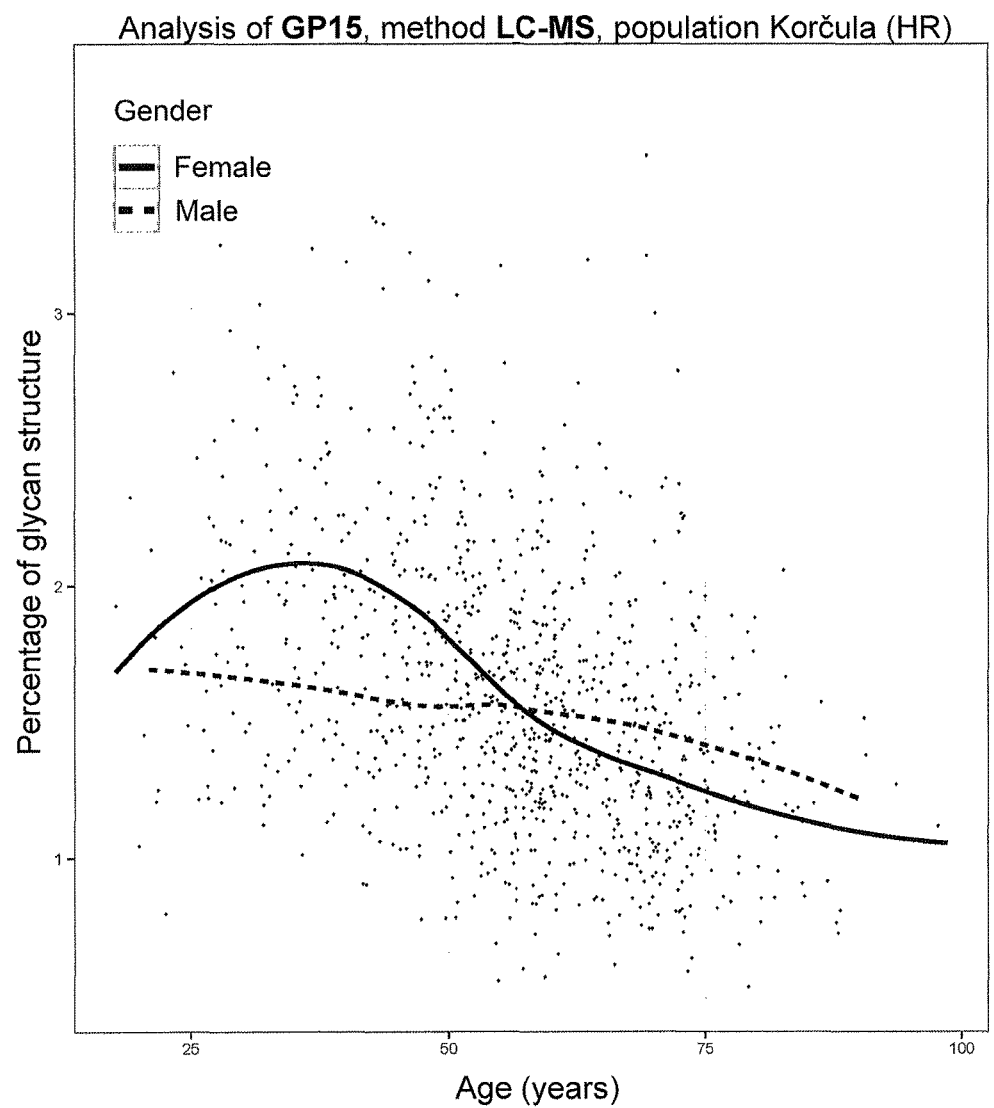
FIG. 20B. Change in the abundance of glycoform F(6)A2BG2 (GP15) with age among women (continuous line) and men (dashed line) in the population of Korčula island (HR), determined by liquid chromatography-mass spectrometry (LC-MS).
Figure 21A:
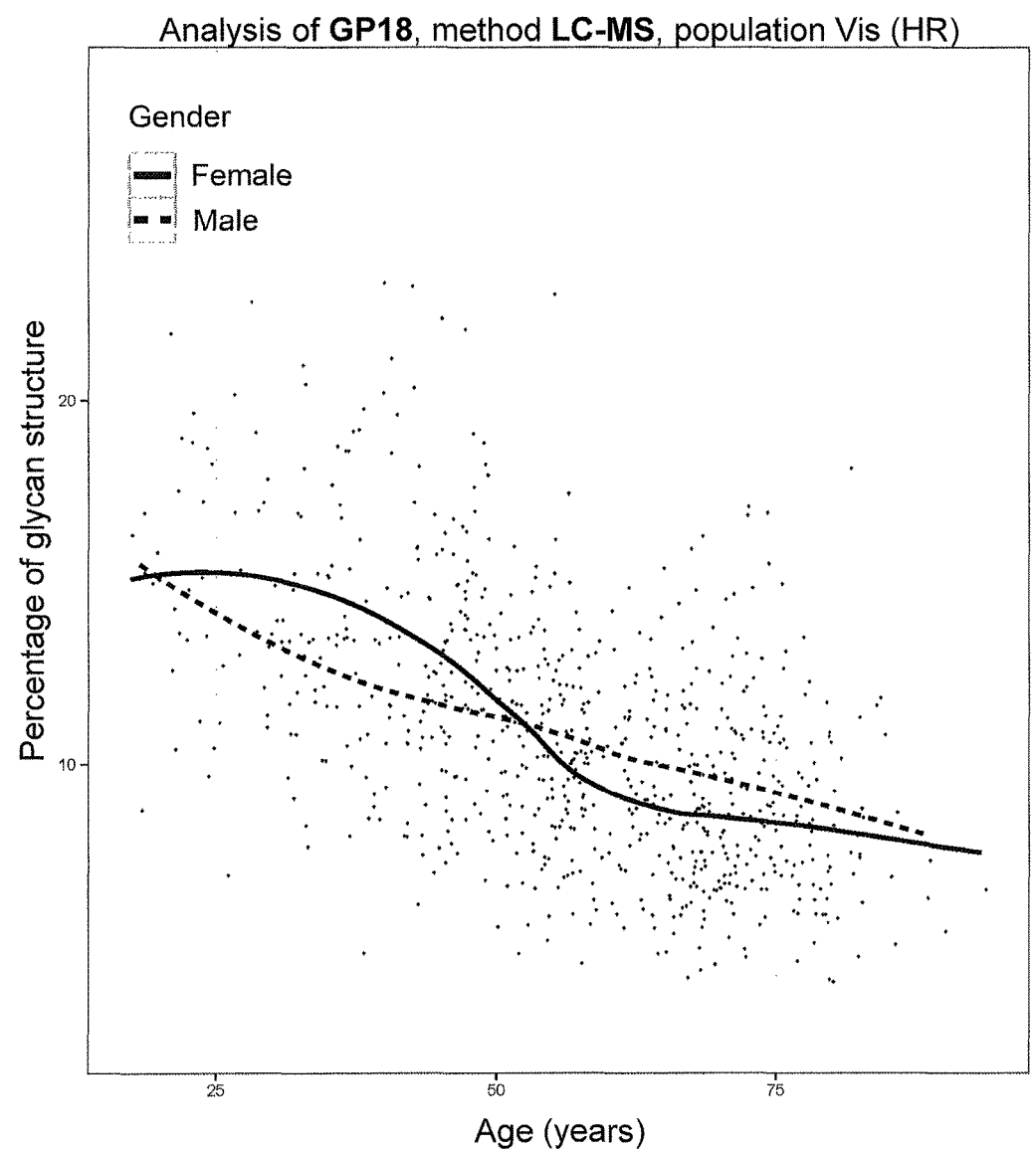
FIG. 21A. Change in the abundance of glycoform F(6)A2G2S1 (GP18) with age among women (continuous line) and men (dashed line) in the population of Vis island (HR), determined by liquid chromatography-mass spectrometry (LC-MS).
Figure 21B:
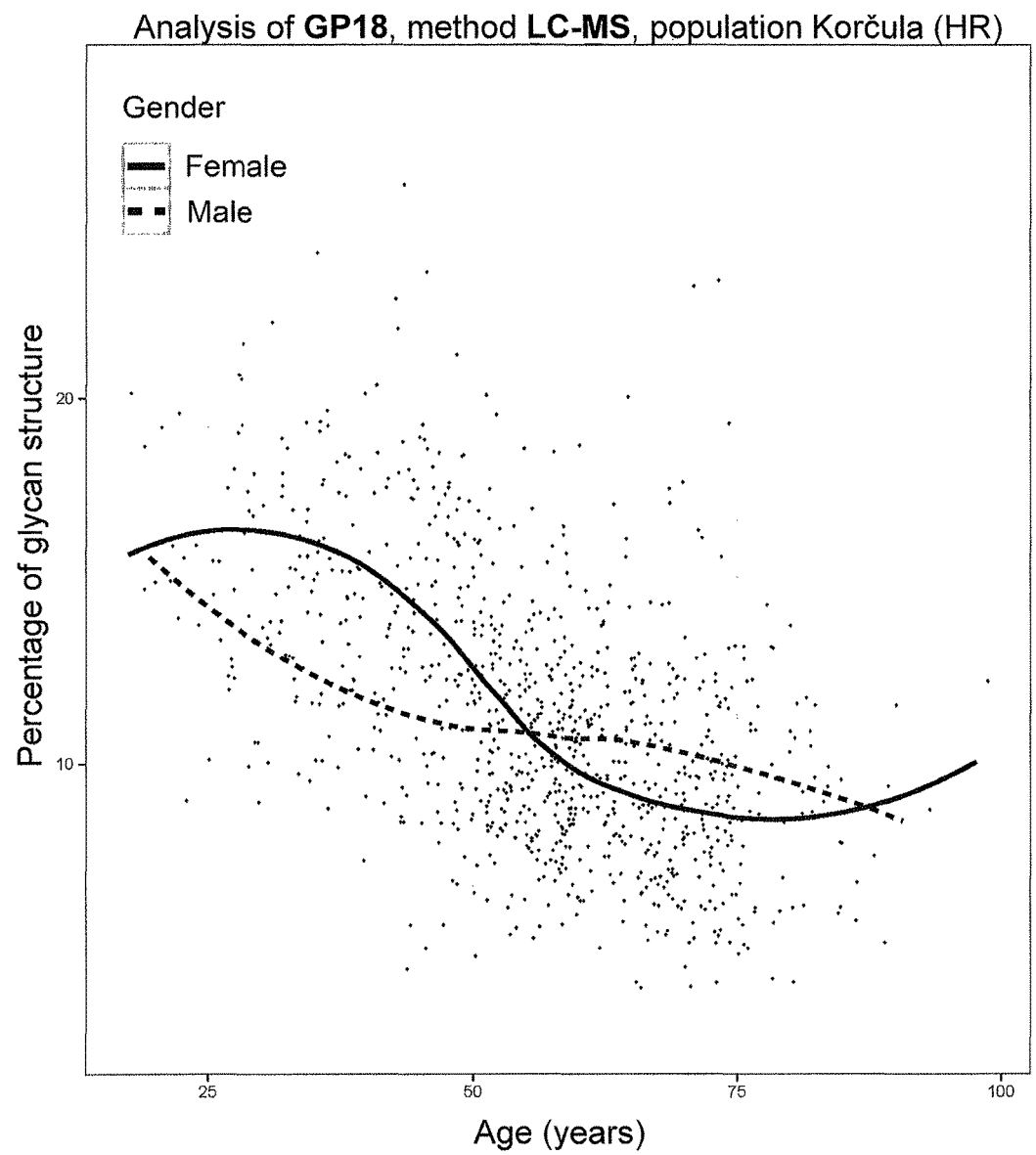
FIG. 21B. Change in the abundance of glycoform F(6)A2G2S1 (GP18) with age among women (continuous line) and men (dashed line) in the population of Korčula island (HR), determined by liquid chromatography-mass spectrometry (LC-MS).

Alternatively, with application of LC-MS analytical technique, liquid chromatography-mass spectrometry of the nanoLC-ESI-MS (nano liquid chromatography-electrospray ionization-mass spectrometry) type, it is possible to determine abundance of individual glycoforms in analogue manner, which correspond to IgG glycans characteristic for age in processed samples that are isolated from blood plasma according to previously described steps. A typical MS-spectrum is shown in FIG. 15 and it shows signals (isotopic peaks) of IgG glycoforms, visible with help of this analytical technique, in other words signals of their molecular ions, described through mass-to-charge ratio (m/z). Above each signal, there is a corresponding glycan structure and here, peptide remnant is also schematically marked by abbreviation "pep".

FIG. 15 shows mass spectrums that show glycopeptides of individual IgG subclasses: IgG1 (spectrum A), IgG2, and IgG3 (spectrum B), as well as subclasses IgG4 (spectrum C).

Name of glycan structures: G0, G1, and G2 denote number of galactoses (G) or other monosaccharides in a glycan molecule: fucose (F), bisecting N-acetylglucosamine (N), N-acetylneuraminic acid (S). Such a manner of marking glycan structures is an alternative to the Oxford manner, in this case: G0F (FA2), G1F (FA2G1), G2F (FA2G2), G2FS (FA2G2S1). The listed structures are shown in spectrums A, B, and C two times because they have lower m/z, $[M+3H]^{3+}$ ions on the left side and higher m/z, $[M+2H]^{2+}$ ions on the right side.

Correlation of the abundance of characteristic glycoforms with sex and age of the respondents from the population of Vis island, obtained by LC-MS, is shown in FIGS. 16A-21A, and from Korčula island in FIGS. 16B-21B.

Moreover, it is also possible to carry out quantitative analysis of IgG glycans characteristic for age by analytical technique of capillary electrophoresis (CE). To illustrate successfulness of releasing IgG glycans from blood plasma, we present a typical electropherogram of their fluorescently active derivates, obtained by reductive amination with 9-aminopyrene-1 3 6-trisulfonic acid (APTS) and with 2-picoline borane as reducing agent, see FIG. 22.

Figure 22:
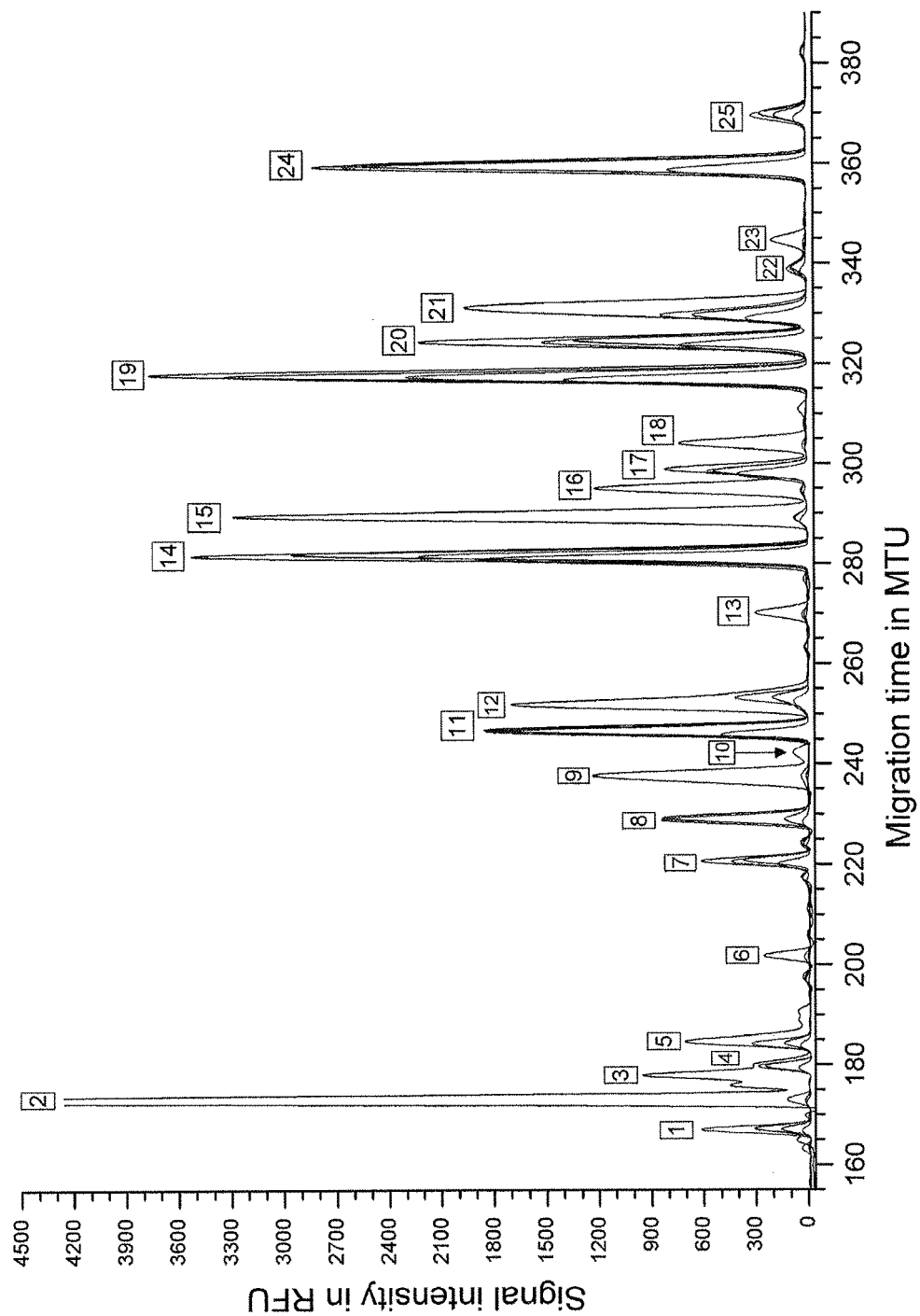
FIG. 22. Typical electropherogram obtained by the quantitative analysis of IgG N-glycans by capillary electrophoresis (CE).

Electropherogram in FIG. 22 shows 25 signals (peaks) of APTS-derivatized IgG glycans that are described by different migration, in other words, retention times (maximum trans-mission unit; MTU), as well as intensities (relative fluorescence unit; RFU).

Figure 24A:
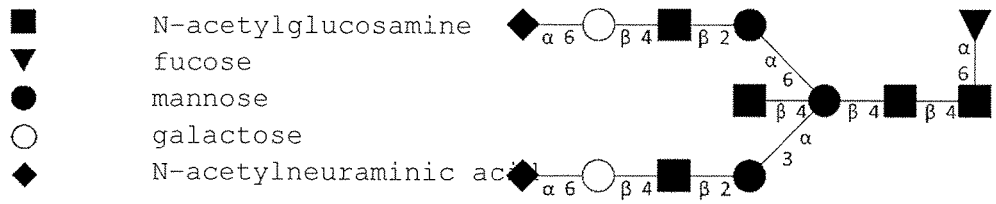
Figure 24C:
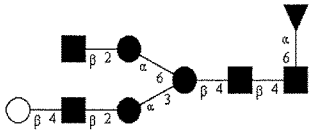
Figure 24C:
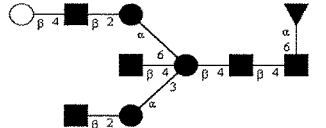
Figure 24C:
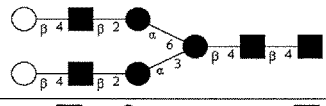
Figure 24C:
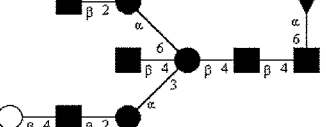
Figure 24C:
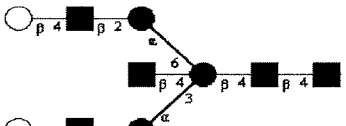
Figure 24C:
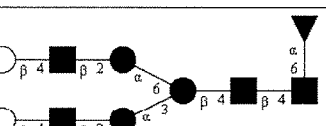
Figure 24C:
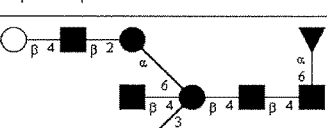

Structures of IgG glycans that are visible by capillary electrophoresis (CE) technique, carried out under the conditions as described in Example 8, are illustrated in FIGS. 24A-24C.

The inventors hold that all carried out and described quantitative analyses (Examples 4, 6, 7, and 8), obtained by very different analytical techniques, clearly indicate that there is possibility to, in general, apply any other appropriate analytical technique that is able to release IgG N-glycans or their corresponding glycopeptides (glycoforms) from processed samples of human blood plasma in sufficiently efficacious manner. In other words, applying some other, alternative, analytical technique or method does not in essence represent a deviation from the contents and scope of the invention in question because its crucial contribution is understanding that exactly characteristic glycans: F(6)A2 (GP4), F(6)A2B (GP6), F(6)A2[6]G1 (GP8), F(6)A2G2 (GP14), F(6)A2BG2 (GP15), and F(6)A2G2S1 (GP18) most strongly correlate with age of a tested individual, while the very manner of their quantitative analysis is irrelevant.

From study of IgG glycans in large populations of isolated groups of people, it has been concluded that glycan structures F(6)A2 (GP4), F(6)A2B (GP6), F(6)A2[6]G1 (GP8), F(6)A2G2 (GP14), F(6)A2BG2 (GP15), F(6)A2G2S1 (GP18) show strongest correlation with age, and as such, they contain most information on chronological age (FIGS. 2-7, 9-14, and 16-21).

Based on the results, a linear model has been determined that enables calculation of Glycan Age Index (GAI) as a separate parameter, obtained by computation on the basis of the results of quantitative analysis of two or more glycans, characteristic for age (GP4, GP6, GP8, GP14, GP15, GP18).

As an example, we present calculation of Glycan Age Index for women and men with application of three characteristic IgG glycans (GP6, GP14, GP15), out of six, according to the following relations:

$$GIA(F)=75.4+135.3 \cdot \langle GP6 \rangle -63.3 \cdot \langle GP6 \rangle^2 -1.1 \cdot \langle GP14 \rangle +3.7 \cdot \langle GP15 \rangle \text{ for female sex};  \quad\quad A.$$

$$GIA(M)=80.2+79.8 \cdot \langle GP6 \rangle -25.1 \cdot \langle GP6 \rangle^2 -2.6 \cdot \langle GP14 \rangle +6.7 \cdot \langle GP15 \rangle \text{ for male sex } (M); \text{ and} \quad B.$$

where $\langle GP6 \rangle$, $\langle GP14 \rangle$ and $\langle GP15 \rangle$ represent quantitative portions of characteristic glycans GP6, GP14, and GP15, determined by quantitative analysis from a respondents' blood plasma. In this process, total sum of all N-glycans or related N-glycopeptides for one chromatogram is 100.

Figure 23:
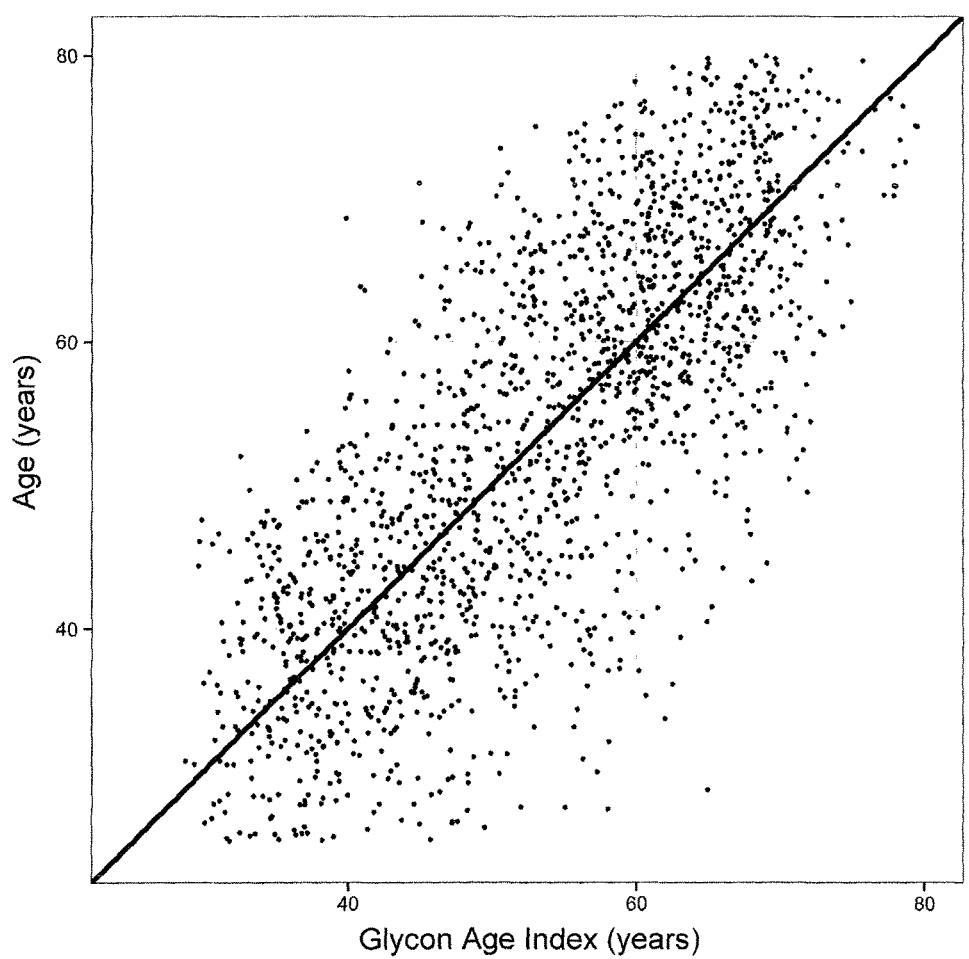
FIG. 23. Illustrates comparison of chronological age and Glycan Age Index (GAI) for the population of Orkney Isles: women (continuous line), men (dashed line).

The mentioned combination of glycans has proved to be optimal in terms of accuracy and avoiding excessive specialization of the model. However, it is possible to calculate Glycan Age Index (GAI) by an analogue manner also from any other combination of two or more mentioned characteristic IgG glycans, out of total six, for which a clear correlation with age and sex has been established. As an example, FIG. 23 shows comparison of chronological age and Glycan Age Index (GAI) in the population of Orkney Isles.

Except for chronological age, Glycan Age Index (GAI) also correlates well with different phenotype markings related to biological age which introduces possibility to use Glycan Age Index (GAI) in analysis of biological age, see Table 1.

TABLE 1

Review of the influence of phenotype markings on Glycan Age Index (GAI) after correction for chronological age.

| No | Parameter | R | $R^2$ | p. val | p. corrected |
|---|---|---|---|---|---|
| 1 | Uric acid | 0.1619 | 0.0282 | 7.271E−12 | 2.908E−10 |
| 2 | Waist measurement | 0.1369 | 0.0208 | 1.290E−08 | 5.032E−07 |
| 3 | Insulin | 0.1234 | 0.0184 | 2.653E−07 | 1.008E−05 |
| 4 | Body mass | 0.1278 | 0.0197 | 1.052E−06 | 3.891E−05 |
| 5 | Glycosylated haemoglobin (HbA1clFCC) | 0.1216 | 0.0140 | 6.693E−06 | 2.409E−04 |
| 6 | High density particles (HDL) | −0.1140 | 0.0157 | 9.307E−06 | 3.164E−04 |
| 7 | Triglycerides | 0.0640 | 0.0088 | 4.308E−05 | 1.422E−03 |
| 8 | Fibrinogen | 0.1326 | 0.0156 | 7.232E−05 | 2.314E−03 |
| 9 | Creatinine | 0.0846 | 0.0076 | 1.369E−04 | 4.242E−03 |
| 10 | Glucose | 0.0874 | 0.0101 | 1.995E−04 | 5.986E−03 |
| 11 | Body mass index (BMI) | 0.1059 | 0.0119 | 3.783E−04 | 1.097E−02 |
| 12 | Alanine aminotransferase (GPT_Regnb) | 0.0787 | 0.0253 | 8.510E−04 | 2.298E−02 |
| 13 | Tissue plasminogen activator (tPA) | 0.1339 | 0.0140 | 1.745E−03 | 4.537E−02 |
| 14 | D dimer | 0.1068 | 0.0121 | 1.760E−03 | 4.537E−02 |

R = coefficient of correlation;
$R^2$ = coefficient of determination;
p. val = nominal p value of phenotype marking association and Glycan Age Index (GAI);
p. corrected = value after correction for multiple testing.

In the above described manner, it is possible to determine biological age of any other human from the analysis of the listed characteristic IgG glycans, as well as it is possible to come to certain conclusions from the results of the analysis, as it is described in the chapter that follows.

Usage of the Method for IgG Glycan Analysis in Accordance with the Invention

The method for the analysis of N-glycans from blood plasma of an individual according to the invention, as well as derived Glycan Age Index (GAI) have a significant diagnostic potential. The method may be used for:

A. precise prediction of biological and/or chronological age of an individual in question;
B. evaluation of progression of diseases related to the ageing process;
C. monitoring efficiency of methods that attempt to slow down the ageing process; as well as for
D. evaluation of general (health) condition of an individual's organism, related to ageing.

Concerning the evaluation of progression of diseases that are related to the ageing process, such diseases are typically chosen from a group that consists of: inflammatory diseases (including atherosclerosis), autoimmune diseases, tumours, diabetes, arthritis, osteoporosis, and Alzheimer disease, which is well known from the previous art; see references:

(10) R. Saldova et al.: Ovarian cancer is associated with changes in glycosylation in both acute-phase proteins and IgG, *Glycobiology* 17 (2007) 1344-1356;
(11) G. Thanabalasingham et al.: Mutations in HNF1A result in marked alterations of plasma glycan profile, *Diabetes* 62 (2013) 1329-1337; and
(12) O. Gornik, G. Lauc: Glycosylation of serum proteins in inflammatory diseases, *Dis. Markers* 25 (2008) 267-278.

EXAMPLES

General Notes

Names of IgG N-glycans that are crucial for the Invention: F(6)A2 (GP4), F(6)A2B (GP6), F(6)A2[6]G1 (GP8), F(6)A2G2 (GP14), F(6)A2BG2 (GP15), F(6)A2G2S1 (GP18), as well as of other glycans, have been derived according to the rules of Oxford nomenclature.

Abbreviations for used reagents and utensils: PBS=phosphate buffered saline (with phosphate buffer at pH=7.4); PES=polyethersulfone; PNGaza F=enzyme peptide-N4-(N-acetyl-beta-glucosamine)asparagine amidase; GHP filter=filter on the basis of hydrophilic polypropylene; SDS=sodium dodecyl sulfate (anionic detergent); APTS=9-aminopyrene-1,3,6-trisulfonic acid; DMSO=dimethyl sulfoxide; NP-40=octylphenyl-polyethyleneglycol (nonionic detergent).

Example 1

Purification of Immunoglobulin G (IgG) from Blood Plasma

Immunoglobulin G (IgG) is purified from blood plasma by affinity chromatography with help of protein G, bonded to monolithic chromatography columns in 96-wells microtiter plates (Bia Separations, Ljubljana, Slovenia). All solutions used during purification are prepared with ultra-pure water and filtered through 0.2 μm PES filters. All washing steps through monolithic columns are executed with the help of vacuum pump (Pall Corporation, MI, USA). Before usage, the columns are washed with 2 mL of water and conditioned with 4 mL of binding buffer (1×PBS; pH=7.4). Before applying on monolithic columns, 100 μL of blood plasma is diluted (1:7, V/V) with binding buffer and filtered through 0.45 μm GHP filter plates. After applying diluted and filtered blood plasma, monolithic plates are washed with 3×2 mL of binding buffer to remove unbound proteins. IgG is eluted from the columns by washing with 1 mL of elution buffer (100 mM formic acid; pH=2.5) and immediately neutralized by adding 1 M ammonium carbonate solution. Purified IgG is stored at −20° C. until usage.

Example 2

Releasing Glycans from Immunoglobulin G (IgG)

Aliquot of purified IgG (app. 100 μg) is dried in vacuum centrifuge, and then resuspended and denatured with 30 μL of 1.33% SDS solution at 65° C. for 10 minutes. After that, 10 μL of 4% NP40, 10 μL of 5×PBS, and 1.25 of mU PNGaze F (N-glycosidase F, ProZyme, CA, USA) is added. The mixture is incubated at 37° C. overnight.

Example 3

Labelling IgG Glycans and Removing Excess of Fluorescent Label

After deglycosylation, 25 μL of mixture for fluorescent labelling is added into the reaction mixture: 0.48 mg of 2-aminobenzamide (2AB) and 1.12 mg of 2-picoline borane in the mixture of acetic acid and DMSO (30%:70%, V/V). The mixture is incubated at 65° C. for 2 hours. Excess of the label is removed with the help of microcrystalline cellulose added to 0.45 μm GHP filter plate. 200 μL of 0.1 g/mL cellulose suspension in the water is placed in each individual well of the filter plate. Cellulose is washed with 5×200 μL of water and conditioned by washing 3 times with 80% acetonitrile. After labelling, the reaction mixture, diluted with 400 μL of acetonitrile, is applied to cellulose. Excess of label is removed by washing cellulose 7 times with 200 μL of 80% acetonitrile. The labelled IgG glycans are eluted by washing cellulose 2 times with 100 μL of water. Eluates of IgG glycans derivatized with 2-aminobenzamide (2AB) are stored at −20° C. until usage.

Example 4

The Analysis of IgG Glycans Labelled with 2-Aminobenzamide (2AB) by Ultra Performance Liquid Chromatography (UPLC) in HILIC Conditions UPLC analysis has been carried out in HILIC (hydrophilic interaction liquid chromatography) conditions: 2-aminobenzamide (2AB)-labelled IgG glycans are analysed on Waters Acquity UPLC instrument (Waters, Mass., USA), equipped with fluorescence detector with excitation and emission wavelengths of 330 and 420 nm, respectively. Glycans are separated on a Waters BEH Glycan chromatography column (100×2.1 mm i.d.; 1.7 μm BEH). As a mobile phase, the following mixture is used:
(1) Solvent A: 100 mM ammonium formate solution, pH=4.4; and
(2) Solvent B: acetonitrile;
with gradient from 75 to 62% V/V acetonitrile; and with the following conditions: flow 0.4 mL/min; time of analysis 25 minutes; samples are stored at 5° C. before injection, while the temperature of the column was 60° C. For each sample a chromatogram is obtained, consisting of 24 chromatographic peaks (GP1-24) which represent individual glycan structures, see FIG. 1. Retention times ($t_R$) of all glycans are listed in Table 2.

TABLE 2

Retention times of 2AB-derivatized IgG glycans, obtained by the described UPLC-HILIC method (see FIG. 1).

| No | Glycan | $t_R$ [min] |
|---|---|---|
| 1 | GP1 | 5.3 |
| 2 | GP2 | 5.5 |
| 3 | GP3 | 5.7 |
| 4 | GP4 | 5.9 |
| 5 | GP5 | 6.1 |
| 6 | GP6 | 6.2 |
| 7 | GP7 | 6.4 |
| 8 | GP8 | 6.6 |
| 9 | GP9 | 6.8 |
| 10 | GP10 | 6.9 |
| 11 | GP11 | 7.0 |
| 12 | GP12 | 7.1 |
| 13 | GP13 | 7.4 |
| 14 | GP14 | 7.5 |
| 15 | GP15 | 7.7 |
| 16 | GP16 | 8.1 |
| 17 | GP17 | 8.4 |
| 18 | GP18 | 8.8 |
| 19 | GP19 | 9.0 |
| 20 | GP20 | 9.5 |
| 21 | GP21 | 9.6 |
| 22 | GP22 | 9.8 |
| 23 | GP23 | 10.0 |
| 24 | GP24 | 10.2 |

By integration of chromatographic peaks of glycans characteristic for age (GP4, GP6, GP8, GP14, GP15, and GP18) their area is obtained and it is divided with total area of the entire chromatogram for the purpose of normalization and in this manner, their relative abundance is determined.

Example 5

The Procedure of Digesting IgG with Help of Trypsin Enzyme and Purification of Released Glycopeptides (Among which are Glycoforms that Respond to Glycans GP4, GP6, GP8, GP14, GP15, and GP18) with Help of Reverse Phase Solid-Phase Extraction Aliquot of purified immunoglobulin (IgG; approximately 20 μg), obtained by purification from blood plasma (the eluate from Example 1), is digested by treating with trypsin enzyme in concentration of 0.02 μg/μL for 20 hours. After that, the obtained glycoforms, including those that correspond to glycans GP4, GP6, GP8, GP14, GP15, and GP18, are purified by reverse phase solid-phase extraction (Chromabond C18). Eluates are dried in vacuum centrifuge until reaching constant mass and then they are resuspended in known volume of ultra-pure water, and stored at −20° C. until usage.

Example 6

Analysis of IgG Glycans by Analysing the Corresponding Glycopeptides i.e. Glycoforms that Correspond to Glycans GP4, GP6, GP8, GP14, GP15, and GP18 with Help of MALDI-TOF Mass Spectrometry Aliquot of purified IgG glycopeptides (the product from Example 5) is spotted to MALDI plate made of stainless steel, then is covered with 1 μL of solution (matrix) 3-(4-chlorophenyl)-2-cyano-2-propyl acid (5 mg/mL) in 50% acetonitrile, and is left to air dry. Glycopeptides from the sample are analysed by UltrafleX II MALDI-TOF/TOF mass spectrometer (Bruker Daltonics) in reflectron mode, with detection of negative ions m/z with values from 1000 to 3800. Data are analysed with help of FlexAnalysis software (Bruker Daltonics). With this method, it is possible to detect 16 IgG glycopeptides of subclass 1 (IgG1), and 11 IgG glycopeptides of subclass 2 (IgG2) and subclass 3 (IgG3). It is not possible to differentiate glycopeptides of subclass 2 (IgG2) and subclass 3 (IgG3) due to identical peptide sequence. By integration and summing intensity of four isotopic peaks of an individual glycopeptide, its area is obtained and it is divided with total area of all glycopeptides of a certain IgG subclass with purpose of normalization. In this manner, abundances of individual glycopeptides i.e. glycoforms that correspond to glycans GP4, GP6, GP8, GP14, GP15, and GP18 from a certain IgG subclass are determined.

Typical MALDI TOF MS-spectrum is shown in FIG. 8.

Example 7

Analysis of IgG Glycans by Analysis of the Corresponding Glycopeptides i.e. Glycoforms that Correspond to Glycans GP4, GP6, GP8, GP14, GP15, and GP18, with Help of Liquid Chromatography-Mass Spectrometry (LC-MS)

Aliquot of purified IgG glycopeptides (the product from Example 5) is subjected to the analysis by liquid chromatography-mass spectrometry of the nanoLC-ESI-MS type on Ultimate 3000 HPLC (micrOTOF-Q, Bruker Daltonics)

instrument, equipped with electrospray ionization source in accordance with the method described in the following reference:

(13) M. H. Selman, R. J. Derks, A. Bondt, M. Palmblad, B. Schoenmaker, C. A. Koeleman, F. E. van de Geijn, R. J. Dolhain, A. M. Deelder, M. Wuhrer: Fc specific IgG glycosylation profiling by robust nano-reverse phase HPLC-MS using a sheath-flow ESI sprayer interface, *J. Proteomics* 75 (2011) 1318-1329.

18 IgG glycopeptides of subclass 1, 18 IgG glycopeptides of subclass 2, and 10 IgG glycopeptides of subclass 4 are detected. By integration and summing intensity of three isotopic peaks of an individual gylcopeptide, its area is obtained and it is divided with total area of all glycopeptides of a certain subclass of IgG for the purpose of normalization. In this manner, relative abundance of glycopeptides i.e. glycoforms that correspond to glycans GP4, GP6, GP8, GP14, GP15, and GP18 are determined.

Typical spectrum obtained by LC-ESI-MS technique is shown in FIG. 15.

Example 8

Analysis of IgG Glycans Labelled with APTS with Help of Capillary Electrophoresis (CE)

Releasing glycans from immunoglobulin G (IgG): aliquot of purified IgG (approximately 100 μg; the product from Example 5) is dried in vacuum centrifuge until reaching constant mass. The dried eluate is resuspended and denatured with 30 μL of 1.33% SDS solution at 65° C. for 10 minutes. After that, 10 μL of 4% NP-40 solution, 10 μL of 5×PBS, and 1.25 mU of enzyme PNGaze F (N-glycosidase F; ProZyme, CA, USA) ars added. The mixture is incubated at 37° C. overnight.

Labelling IgG glycans by reductive amination with APTS, removal of excess of fluorescent label and capillary electrophoresis: released N-glycans (2 μL) are labelled by adding 2 μL 20 mM of 9-aminopyrene-1,3,6-trisulfonic acid (APTS) solution as fluorescent label in 3,6 M of citric acid solution with addition of 2 μL of 2-picoline borane solution in DMSO. The obtained reaction mixture is incubated at 37° C. overnight. Excess of fluorescent label is removed by solid-phase extraction with help of microcrystalline cellulose, Sepharose, or Biogel P-10, in accordance with the procedure from the following reference:

(14) L. R. Ruhaak, R. Hennig, C. Huhn, M. Borowiak, R. J. Dolhain, A. M. Deelder, E. Rapp, M. Wuhrer: Optimized workflow for preparation of APTS-labelled N-glycans allowing high-throughput analysis of human plasma glycomes using 48-channel multiplexed CGE-LIF, *J. Proteome Res.* 9 (2010) 6655-6664.

For the analysis of purified and fluorescently labelled IgG N-glycans, ABI 3130xL genetic analyser, equipped with 16 capillary filled with POP-7 Polymer (Life Technologies), is used. Electrophoresis is carried out at the potential of 15 kV, and the collection of data takes 45 minutes. Data analysis is carried out by glyXtool and glyXalign software packages. An electropherogram is obtained for every sample and it consists of 25 peaks which represent individual glycan structures. By integration of peaks, their area is obtained and it is divided with total area of the entire integrated electropherogram for the purpose of normalization. In this manner, abundance of an individual glycan is determined.

Typical electropherogram of IgG glycan obtained by the described method is shown in FIG. 22.

Example 9

Carrying Out the Study of Investigating IgG N-Glycans Depending on Age and Sex in Three Different Isolated Populations: Vis Island, Korčula Island and Orkney Isles For the purpose of defining Glycan Age Index (GAI), results of IgG glycan analysis of respondents from three populations are used: the island of Vis (CRO), the island of Korčula (CRO) and Orkney Isles (UK). The population of Vis island included 890 respondents (521 women and 369 men), ranging in age from 18 to 93 (average age 56). The population of Korčula island included 915 respondents (595 women and 320 men), ranging in age from 18 to 98 (average age 56). The population of Orkney Isles included 1786 respondents (1082 women and 704 men), ranging in age from 16 to 100 (average age 54).

Blood samples are taken by collecting blood in test tubes with anticoagulant, and instantly being processed by centrifugation in order to isolate blood plasma. Blood plasma is stored at −70° C. The procedure of purification of immunoglobulin G (IgG) that contains various attached glycans from blood plasma is described in Example 1.

Releasing glycans from their attachment to immunoglobulin G (IgG) is executed by a favourable method known from the background of the Invention: hidrazinolysis or enzyme reaction catalysed by peptide-N4-(N-acetyl-beta-glucosaminyl)asparagine amidase (PNGaza F), as described in Example 2.

Fluorescent labelling of glycans by reductive amination is executed with 2-aminobenzamide (2AB) or with 9-aminopyrene-1 3 6-trisulfonic acid (APTS), using 2-picoline borane (2-$CH_3C_5H_4N \cdot BH_3$) as reducing agent, in accordance with the procedures described in Examples 3 and 8.

Alternatively, purified immunoglobulin G (IgG) is treated with trypsine enzyme and released glycopeptides are subsequently purified by reverse phase solid-phase extraction with quantitative analysis by MALDI-TOF mass spectrometry and LC-MS, in accordance with the procedures described in Examples 6 and 7.

The procedures of quantitative analysis of fluorescently derivatized glycans or their glycoproteins are described in Example 4 (UPLC), Example 6 MALDI-TOF), Example 7 (LC-MS), and Example 8 (CE).

As a result of quantitative analysis, a chromatogram, electropherogram, or mass spectrum are obtained with a series of peaks (signals) that represent one or more related glycan structures, i.e. glycopeptides (FIGS. 1, 8, 15, and 22).

Relative abundance of individual IgG glycans (in the study on different isolated human populations, as well as in testing blood plasma of any human in accordance with the Invention) is determined by normalization of the area underneath the signal (peak) with total area underneath all signals (peaks) of glycans. In case of mass spectrometry, abundance of individual glycopeptides, i.e. glycoforms is determined by normalization of the sum of the intensity of isotopic peaks of a certain glycoform with total intensity of all glycoforms.

Obtained values of IgG glycan structures are also normalized with regard to individual characteristics of the experiment for which it is known to bring errors into the experiment: the plate on which the experiment has been carried out, instrument on which chromatographic analysis has been carried out, etc. For this purpose, a linear mixed model has been used, in which experimental variables are described as random effects.

The entire statistic data processing is executed with help of R programming language, designed for statistical computing and graphics. GUI version of the program R 3.0.0. for 64-bit Windows is used. All the functions used in statistical data processing are part of R basic package for statistical computing "stats," and R packaging for linear mixed models "lme4". Visualisation of data and results of statistical analysis is carried out by using R graphic package "ggplot2".

The results of data processing from the study on abundance of individual IgG glycans in isolated human populations are described in the chapter "Detailed Description" and are shown in FIGS. 1-23.

CONCLUSION (i) The Invention reveals a new method for the analysis of N-glycans attached to immunoglobulin G (IgG) from human blood plasma which includes quantitative analysis of two or more IgG glycans chosen from the group that consists of: F(6)A2 (GP4), F(6)A2B (GP6), F(6)A2[6]G1 (GP8), F(6)A2G2 (GP14), F(6)A2BG2 (GP15), and F(6)A2G2S1 (GP18). For these glycans, strong correlation with age and sex has been determined earlier on the basis of a completed study on IgG glycan composition.

(ii) The method of IgG glycan analysis in accordance with the Invention enables the following: precise prediction of biological and/or chronological age of a certain individual; evaluation of progression of diseases related to the ageing process; monitoring efficacy of methods that attempt to slow down the ageing process; and evaluation of the overall health of an individual, related to ageing.

(iii) The method of the analysis includes known methods of purification and isolation of IgG glycans from blood plasma, known methods of releasing glycans from their attachment to immunoglobulin G (IgG), known methods of fluorescent labelling of glycans by reductive amination, and known analytical techniques of quantitative analysis: UPLC, MALDI-TOF mass spectrometry, LC-MS, CE, or other favourable analytical techniques. However, the procedure is based on a statistically determined correlation between:

A. frequency of the mentioned six specific IgG glycans, characteristic for age and sex; and
B. determining biological age of a certain individual and prediction of other mentioned states and diseases related to the ageing process;

nevertheless, it is not known from the prior art and could not have been derived from it.

The invention claimed is:

1. A method for calculating a Glycan Age Index (GAI) of an individual, comprising the following steps:
   (i) digesting immunoglobulin G (IgG) from a blood plasma sample from the individual with N-glycanase F to obtain IgG N-glycans or digesting IgG from the sample with trypsin to obtain IgG N-glycopeptides;
   (ii) determining relative abundances of F(6)A2B (GP6), F(6)A2G2 (GP14), and F(6)A2BG2 (GP15) glycans or their corresponding IgG N-glycopeptides in the sample using a method selected from the group consisting of ultra-performance liquid chromatography, MALDI-TOF mass spectrometry, liquid chromatography-mass spectrometry and capillary electrophoresis to obtain a chromatogram, electropherogram, or mass spectrum, wherein the F(6)A2B (GP6), F(6)A2G2 (GP14), and F(6)A2BG2 (GP15) glycans have the following chemical structures:

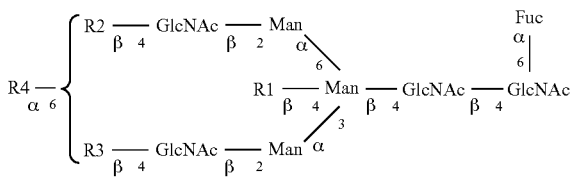

wherein:
F(6)A2B (GP6): R1=GlcNAc; R2, R3, R4=H
F(6)A2G2 (GP14): R1=H; R2, R3=Gal; R4=H
F(6)A2BG2 (GP15): R1=GlcNAc; R2, R3=Gal; R4=H
and
GlcNAc =N-acetylglucosamine
Fuc =fucose
Man =mannose
NeuAc =N-acetylneuraminic acid
Gal =galactose
wherein the relative abundance of each of the F(6)A2B (GP6), F(6)A2G2 (GP14), and F(6)A2BG2 (GP15) glycans or its corresponding IgG N-glycopeptides is obtained by normalization performed by dividing an area underneath a signal of the F(6)A2B (GP6), F(6)A2G2 (GP14), and F(6)A2BG2 (GP15) glycan or its corresponding IgG N-glycopeptides in the chromatogram, electropherogram, or mass spectrum, with a total area underneath all signals of IgG N-glycans or IgG N-glycopeptides in the sample, wherein values (GP6), (GP14), and (GP15) represent the relative abundances of the glycans F(6)A2B (GP6) or its corresponding IgG N-glycopeptides, F(6)A2G2 (GP14) or its corresponding IgG N-glycopeptides, and F(6)A2BG2 (GP15) or its corresponding IgG N-glycopeptides for the individual, respectively; and
(iii) calculating the Glycan Age Index (GAI), wherein the GAI is expressed in years and determined according to the following formulas in relation to the individual's sex:

$$GAI(F)=75.4+135.3\cdot\langle GP6\rangle-63.3\cdot\langle GP6\rangle^2-1.1\cdot\langle GP14\rangle+3.7\cdot\langle GP15\rangle \text{ for female sex}(F);$$

$$GAI(M)=80.2+79.6\cdot\langle GP6\rangle-25.1\cdot\langle GP6\rangle^2-2.6\cdot\langle GP14\rangle+6.7\cdot\langle GP15\rangle \text{ for male sex }(M).$$

2. The method of claim 1, further comprising predicting the biological and chronological age of the individual.

3. The method of claim 1, further comprising monitoring efficacy of a method for slowing down the aging process of the individual.

4. The method of claim 1, further comprising monitoring progression of a disease developed as a result of the aging process of the individual.

5. The method of claim 4, wherein the disease is selected from the group consisting of inflammatory diseases including atherosclerosis, autoimmune diseases, tumours, diabetes, arthritis, osteoporosis, and Alzheimer disease.

* * * * *